US012751784B2

(12) United States Patent
Rodriguez-Navarro et al.

(10) Patent No.: US 12,751,784 B2
(45) Date of Patent: Oct. 6, 2026

(54) RETRACTOR SYSTEMS, DEVICES, AND METHODS FOR USE

(71) Applicant: Levita Magnetics International Corp., Menlo Park, CA (US)

(72) Inventors: Alberto Rodriguez-Navarro, San Francisco, CA (US); Mariel Fabro, San Francisco, CA (US); Archana Nair, Eden Prairie, MN (US); Olgy Datto, Baton Rouge, LA (US); Ruth Beeby, Mountain View, CA (US); Bryan Loomas, Los Gatos, CA (US)

(73) Assignee: LEVITA MAGNETICS INTERNATIONAL CORP., Mountain View, CA (US)

( * ) Notice: Subject to any disclaimer, the term of this patent is extended or adjusted under 35 U.S.C. 154(b) by 623 days.

(21) Appl. No.: 18/110,755

(22) Filed: Feb. 16, 2023

(65) Prior Publication Data

US 2023/0277266 A1 Sep. 7, 2023

Related U.S. Application Data

(63) Continuation of application No. 15/728,297, filed on Oct. 9, 2017, now Pat. No. 11,583,354, which is a
(Continued)

(51) Int. Cl.

| | |
|---|---|
| ***A61B 17/02*** | (2006.01) |
| ***A61B 34/00*** | (2016.01) |
| *A61B 17/00* | (2006.01) |

(52) U.S. Cl.

CPC .......... *A61B 34/73* (2016.02); *A61B 17/0218* (2013.01); *A61B 2017/00283* (2013.01);
(Continued)

(58) Field of Classification Search

CPC .......... A61B 2017/00283; A61B 34/73; A61B 2017/00876; A61B 17/0218; A61B 34/70; A61B 17/0281; A61B 17/00234

See application file for complete search history.

(56) References Cited

U.S. PATENT DOCUMENTS

| | | | |
|---|---|---|---|
| 2,678,228 | A | 5/1954 | Gerhardt |
| 2,863,444 | A | 12/1958 | Winsten |

(Continued)

FOREIGN PATENT DOCUMENTS

| | | | |
|---|---|---|---|
| AU | 2016204942 | A1 | 2/2017 |
| CA | 2 748 471 | A1 | 7/2010 |

(Continued)

OTHER PUBLICATIONS

Aesculap, "Endoscopic Vascular surgery in the pelvic region," B/Braun, Aesculap AG & CO.KG, Catalog, 48 pages, 2006, Copy Unavailable, document can be accessed at https://docplayer.net/22042174-Aesculap-endoscopic-technology-endoscopic-vascular-surgery-in-the-pelvic-region.html.

(Continued)

*Primary Examiner* — Lynnsy M Summitt
(74) *Attorney, Agent, or Firm* — Cooley LLP

(57) ABSTRACT

Described here are devices, systems, and methods for moving and/or supporting an internal organ or other tissue, such as during minimally-invasive surgery. Generally, a system for moving and/or supporting tissue may comprise a magnetic control component and a retractor having at least one magnetic portion. The retractor may have a first low-profile configuration for passing through an incision into a surgical site within a patient and a second expansive configuration for engaging tissue. The magnetic control component may
(Continued)

be placed over the surgical site external to the patient and generate a magnetic field to manipulate the retractor and engaged tissue.

18 Claims, 33 Drawing Sheets

Related U.S. Application Data continuation of application No. PCT/US2016/027385, filed on Apr. 13, 2016.

(60) Provisional application No. 62/146,924, filed on Apr. 13, 2015.

(52) U.S. Cl.
CPC ............... *A61B 2017/00876* (2013.01); *A61B 2017/0212* (2013.01); *A61B 2017/0225* (2013.01); *A61B 2034/733* (2016.02)

(56) References Cited

U.S. PATENT DOCUMENTS 3,146,381 A 8/1964 Louis
3,674,014 A 7/1972 Tillander
3,789,285 A 1/1974 Nishizawa
3,794,091 A 2/1974 Ersek et al.
4,364,377 A 12/1982 Smith
4,380,999 A 4/1983 Healy
4,706,668 A 11/1987 Backer
4,756,312 A 7/1988 Epley
4,901,405 A 2/1990 Grover et al.
4,915,435 A 4/1990 Levine
4,968,136 A 11/1990 Lim et al.
4,971,067 A 11/1990 Bolduc et al.
4,976,723 A 12/1990 Schad
4,997,436 A 3/1991 Oberlander
5,002,557 A 3/1991 Hasson
5,154,189 A 10/1992 Oberlander
5,156,608 A 10/1992 Troidl et al.
5,156,609 A 10/1992 Nakao et al.
5,282,806 A 2/1994 Haber et al.
5,300,081 A 4/1994 Young et al.
5,304,183 A 4/1994 Gourlay et al.
5,304,185 A 4/1994 Taylor
5,307,805 A 5/1994 Byrne
5,340,360 A 8/1994 Stefanchik
5,397,325 A 3/1995 Della Badia
5,411,535 A 5/1995 Fujii et al.
5,415,160 A 5/1995 Ortiz et al.
5,417,701 A 5/1995 Holmes
5,449,361 A 9/1995 Preissman
5,449,365 A 9/1995 Green et al.
5,450,842 A 9/1995 Tovey et al.
5,458,603 A 10/1995 Futch, Sr.
5,458,693 A 10/1995 Codorniu
5,465,711 A 11/1995 Moll et al.
5,496,317 A 3/1996 Goble et al.
5,499,986 A 3/1996 Dimarco
5,529,568 A 6/1996 Rayman
5,538,098 A 7/1996 Sparhawk
5,567,274 A 10/1996 Funk et al.
5,569,274 A 10/1996 Rapacki et al.
5,593,379 A 1/1997 Rayman
5,595,562 A 1/1997 Grier
5,654,864 A 8/1997 Ritter et al.
5,665,100 A 9/1997 Yoon
5,681,260 A 10/1997 Ueda et al.
5,728,121 A 3/1998 Bimbo et al.
5,733,292 A 3/1998 Gustilo et al.
5,749,881 A 5/1998 Sackier et al.
5,766,189 A 6/1998 Matsuno
5,782,748 A 7/1998 Palmer et al.
5,797,911 A 8/1998 Sherman et al.
5,797,939 A 8/1998 Yoon
5,824,041 A 10/1998 Lenker et al.
5,848,969 A 12/1998 Panescu et al.
5,849,015 A 12/1998 Haywood et al.
5,888,196 A 3/1999 Bonutti
5,893,873 A 4/1999 Rader et al.
5,933,926 A 8/1999 Reiter
6,015,414 A 1/2000 Werp et al.
6,017,358 A 1/2000 Yoon et al.
6,096,038 A 8/2000 Michelson
6,099,537 A 8/2000 Sugai et al.
6,099,550 A 8/2000 Yoon
6,123,657 A 9/2000 Ishikawa et al.
6,126,647 A 10/2000 Posey et al.
6,127,757 A 10/2000 Swinbanks
6,165,180 A 12/2000 Cigaina et al.
6,173,715 B1 1/2001 Sinanan et al.
6,212,419 B1 4/2001 Blume et al.
6,216,028 B1 4/2001 Haynor et al.
6,241,671 B1 6/2001 Ritter et al.
6,311,082 B1 10/2001 Creighton, IV et al.
6,315,709 B1 11/2001 Garibaldi et al.
6,330,467 B1 12/2001 Creighton, IV et al.
6,340,365 B2 1/2002 Dittrich et al.
6,358,196 B1 3/2002 Rayman
6,371,973 B1 4/2002 Tepper
6,398,791 B1 6/2002 Que et al.
6,399,146 B1 6/2002 Harris et al.
6,401,723 B1 6/2002 Garibaldi et al.
6,440,133 B1 8/2002 Beale et al.
6,458,146 B1 10/2002 Kramer
6,459,924 B1 10/2002 Creighton, IV et al.
6,464,710 B1 10/2002 Foster
6,488,615 B1 12/2002 Mitchiner et al.
6,523,919 B1 2/2003 Israelsen et al.
6,537,196 B1 3/2003 Creighton, IV et al.
6,551,304 B1 4/2003 Whalen et al.
6,594,517 B1 7/2003 Nevo
6,630,879 B1 10/2003 Creighton, IV et al.
6,632,229 B1 10/2003 Yamanouchi
6,641,595 B1 11/2003 Moran et al.
6,656,199 B1 12/2003 Lafontaine
6,677,752 B1 1/2004 Creighton, IV et al.
6,689,119 B1 2/2004 Di Caprio et al.
6,702,804 B1 3/2004 Ritter et al.
6,705,989 B2 3/2004 Cuschieri et al.
6,719,765 B2 4/2004 Bonutti
6,761,681 B2 7/2004 Schmid et al.
6,786,219 B2 9/2004 Garibaldi et al.
6,817,364 B2 11/2004 Garibaldi et al.
6,824,511 B1 11/2004 Bell et al.
6,916,314 B2 7/2005 Schneider et al.
7,017,584 B2 3/2006 Garibaldi et al.
7,094,245 B2 8/2006 Adams et al.
7,169,104 B2 1/2007 Ueda et al.
7,182,089 B2 2/2007 Ries
7,182,775 B2 2/2007 De Guillebon et al.
7,189,198 B2 3/2007 Harburn et al.
7,264,584 B2 9/2007 Ritter et al.
7,300,400 B2 11/2007 Brown
7,311,107 B2 12/2007 Harel et al.
7,313,429 B2 12/2007 Creighton, IV et al.
7,314,063 B2 1/2008 Egli
7,341,063 B2 3/2008 Garbibaldi et al.
7,344,553 B2 3/2008 Opolski et al.
7,390,298 B2 6/2008 Chu
7,416,335 B2 8/2008 Munger
7,429,259 B2 9/2008 Cadeddu et al.
7,431,726 B2 10/2008 Spence et al.
7,566,038 B2 7/2009 Scott et al.
7,618,435 B2 11/2009 Opolski
7,686,827 B2 3/2010 Hushka
7,691,103 B2 4/2010 Fernandez et al.
7,691,731 B2 4/2010 Bet et al.
7,708,756 B2 5/2010 Nobis et al.
7,736,356 B2 6/2010 Cooper et al.
7,766,810 B2 8/2010 Ohdaira
7,769,427 B2 8/2010 Shachar
7,772,950 B2 8/2010 Tunay

(56) References Cited

U.S. PATENT DOCUMENTS

| | | | |
|---|---|---|---|
| 7,774,046 | B2 | 8/2010 | Werp et al. |
| 7,780,054 | B2 | 8/2010 | Wales |
| 7,799,050 | B2 | 9/2010 | Hensley et al. |
| 7,837,612 | B2 | 11/2010 | Gill et al. |
| 7,850,591 | B2 | 12/2010 | Spector |
| 7,942,885 | B2 | 5/2011 | Sixto, Jr. et al. |
| 7,963,903 | B2 | 6/2011 | Ghiron et al. |
| 7,966,059 | B2 | 6/2011 | Creighton, IV et al. |
| 7,967,830 | B2 | 6/2011 | Ayala et al. |
| 8,038,612 | B2 | 10/2011 | Paz |
| 8,043,290 | B2 | 10/2011 | Harrison et al. |
| 8,057,472 | B2 | 11/2011 | Walker et al. |
| 8,060,184 | B2 | 11/2011 | Hastings et al. |
| 8,066,715 | B2 | 11/2011 | Ducharme |
| 8,074,657 | B2 | 12/2011 | Scott et al. |
| 8,082,035 | B2 | 12/2011 | Glukhovsky |
| 8,133,254 | B2 | 3/2012 | Dumbauld et al. |
| 8,136,888 | B2 * | 3/2012 | Suzuki ............... A61B 17/0401 600/562 |
| 8,137,268 | B2 | 3/2012 | Van Lue |
| 8,157,149 | B2 | 4/2012 | Olson et al. |
| 8,187,286 | B2 | 5/2012 | Jugenheimer et al. |
| 8,197,494 | B2 | 6/2012 | Jaggi et al. |
| 8,226,690 | B2 | 7/2012 | Altarac et al. |
| 8,235,272 | B2 | 8/2012 | Nicholas et al. |
| 8,241,322 | B2 | 8/2012 | Whitman et al. |
| 8,246,529 | B2 | 8/2012 | Riehl et al. |
| 8,252,021 | B2 | 8/2012 | Boulnois et al. |
| 8,267,854 | B2 | 9/2012 | Asada et al. |
| 8,301,226 | B2 | 10/2012 | Csavoy et al. |
| 8,303,495 | B2 | 11/2012 | Ducharme |
| 8,313,497 | B2 | 11/2012 | Walberg et al. |
| 8,316,861 | B2 | 11/2012 | Brewer et al. |
| 8,316,862 | B2 | 11/2012 | Shapiro et al. |
| 8,333,695 | B2 | 12/2012 | Cuschieri |
| 8,343,171 | B2 | 1/2013 | Farritor et al. |
| 8,360,972 | B2 | 1/2013 | Paz |
| 8,364,277 | B2 | 1/2013 | Glukhovsky |
| 8,377,044 | B2 | 2/2013 | Coe et al. |
| 8,382,754 | B2 | 2/2013 | Odom et al. |
| 8,403,916 | B2 | 3/2013 | Prescott |
| 8,409,076 | B2 | 4/2013 | Pang et al. |
| 8,480,668 | B2 | 7/2013 | Fernandez et al. |
| 8,491,626 | B2 | 7/2013 | Roy et al. |
| 8,517,931 | B2 | 8/2013 | Minnelli et al. |
| 8,518,057 | B2 | 8/2013 | Walberg et al. |
| 8,556,919 | B2 | 10/2013 | Aguirre et al. |
| 8,579,787 | B2 | 11/2013 | Shapiro et al. |
| 8,585,685 | B2 | 11/2013 | Hagg |
| 8,602,981 | B2 | 12/2013 | Deutch |
| 8,608,773 | B2 | 12/2013 | Tierney et al. |
| 8,623,011 | B2 | 1/2014 | Spivey |
| 8,628,529 | B2 | 1/2014 | Aldridge et al. |
| 8,636,762 | B2 | 1/2014 | Whitman et al. |
| 8,637,818 | B2 | 1/2014 | Balakin |
| 8,685,043 | B2 | 4/2014 | Jugenheimer et al. |
| 8,758,394 | B2 | 6/2014 | Zimmerling et al. |
| 8,764,769 | B1 | 7/2014 | Rodriguez-Navarro et al. |
| 8,790,245 | B2 | 7/2014 | Rodriguez Fernandez et al. |
| 8,820,602 | B2 | 9/2014 | Walberg et al. |
| 8,827,891 | B2 | 9/2014 | Roberts |
| 8,828,024 | B2 | 9/2014 | Farritor et al. |
| 8,894,574 | B2 | 11/2014 | Ellman |
| 8,926,656 | B2 | 1/2015 | Palermo et al. |
| 8,944,997 | B2 | 2/2015 | Fernandez et al. |
| 8,968,332 | B2 | 3/2015 | Farritor et al. |
| 8,968,356 | B2 | 3/2015 | Mueller |
| 9,011,468 | B2 | 4/2015 | Ketai et al. |
| 9,033,957 | B2 | 5/2015 | Cadeddu et al. |
| 9,044,256 | B2 * | 6/2015 | Cadeddu ................ A61B 34/73 |
| 9,339,285 | B2 | 5/2016 | Rodriguez-Navarro et al. |
| 9,386,973 | B2 | 7/2016 | Deutch |
| 9,561,031 | B2 | 2/2017 | Heinrich et al. |
| 9,627,120 | B2 | 4/2017 | Scott et al. |
| 9,743,929 | B2 | 8/2017 | Leimbach et al. |
| 9,844,391 | B2 | 12/2017 | Rodriguez Fernandez et al. |
| 9,962,148 | B2 | 5/2018 | Deutch |
| 9,974,546 | B2 | 5/2018 | Rodriguez Fernandez et al. |
| 10,010,370 | B2 | 7/2018 | Rodriguez-Navarro et al. |
| 10,130,381 | B2 | 11/2018 | Rodriguez-Navarro et al. |
| 10,143,459 | B2 | 12/2018 | Heftman |
| 10,335,134 | B2 | 7/2019 | Deutch |
| 10,537,348 | B2 | 1/2020 | Rodriguez-Navarro et al. |
| 10,779,809 | B2 * | 9/2020 | Suzuki ............... A61B 17/0218 |
| 10,905,511 | B2 * | 2/2021 | Rodriguez-Navarro ..................... A61B 90/361 |
| 11,020,137 | B2 | 6/2021 | Rodriguez-Navarro |
| 11,357,525 | B2 | 6/2022 | Rodriguez-Navarro et al. |
| 11,413,025 | B2 | 8/2022 | Deutch |
| 11,413,026 | B2 | 8/2022 | Deutch |
| 11,583,354 | B2 | 2/2023 | Rodriguez-Navarro et al. |
| 11,730,476 | B2 | 8/2023 | Rodriguez-Navarro et al. |
| 11,751,965 | B2 | 9/2023 | Rodriguez-Navarro et al. |
| 12,171,433 | B2 | 12/2024 | Rodriguez-Navarro et al. |
| 12,185,962 | B2 | 1/2025 | Rodriguez-Navarro |
| 12,262,971 | B2 | 4/2025 | Rodriguez-Navarro et al. |
| 12,329,402 | B2 | 6/2025 | Rodriguez-Navarro et al. |
| 12,357,407 | B2 | 7/2025 | Rodriguez-Navarro et al. |
| 2001/0038683 | A1 | 11/2001 | Ritter et al. |
| 2002/0100486 | A1 | 8/2002 | Creighton, IV et al. |
| 2002/0107533 | A1 | 8/2002 | Solingen |
| 2002/0116043 | A1 | 8/2002 | Garibaldi et al. |
| 2002/0173805 | A1 | 11/2002 | Matsuno et al. |
| 2003/0114731 | A1 | 6/2003 | Cadeddu et al. |
| 2003/0125752 | A1 | 7/2003 | Werp et al. |
| 2003/0181945 | A1 | 9/2003 | Opolski et al. |
| 2003/0208185 | A1 | 11/2003 | Sheffer et al. |
| 2004/0044295 | A1 | 3/2004 | Reinert et al. |
| 2004/0050395 | A1 | 3/2004 | Ueda et al. |
| 2004/0064153 | A1 | 4/2004 | Creighton, IV et al. |
| 2004/0068173 | A1 | 4/2004 | Viswanathan |
| 2004/0158972 | A1 | 8/2004 | Creighton, IV et al. |
| 2004/0172057 | A1 | 9/2004 | Guillebon et al. |
| 2004/0186347 | A1 | 9/2004 | Shose et al. |
| 2004/0199074 | A1 | 10/2004 | Ritter et al. |
| 2004/0230100 | A1 | 11/2004 | Shluzas |
| 2004/0249262 | A1 | 12/2004 | Werp et al. |
| 2005/0080440 | A1 | 4/2005 | Durgin et al. |
| 2005/0085696 | A1 | 4/2005 | Uchiyama et al. |
| 2005/0113628 | A1 | 5/2005 | Creighton et al. |
| 2005/0131390 | A1 | 6/2005 | Heinrich et al. |
| 2005/0165449 | A1 | 7/2005 | Cadeddu et al. |
| 2005/0220583 | A1 | 10/2005 | Lutz |
| 2005/0250988 | A1 | 11/2005 | Ewers et al. |
| 2005/0251183 | A1 | 11/2005 | Buckman et al. |
| 2005/0277975 | A1 | 12/2005 | Saadat et al. |
| 2006/0015178 | A1 | 1/2006 | Moaddeb et al. |
| 2006/0074448 | A1 | 4/2006 | Harrison et al. |
| 2006/0079897 | A1 | 4/2006 | Harrison et al. |
| 2006/0089633 | A1 | 4/2006 | Bleich et al. |
| 2006/0116714 | A1 | 6/2006 | Sepetka et al. |
| 2006/0149135 | A1 | 7/2006 | Paz |
| 2006/0152309 | A1 | 7/2006 | Mintchev et al. |
| 2006/0228421 | A1 | 10/2006 | Seeney et al. |
| 2006/0241691 | A1 | 10/2006 | Wilk |
| 2006/0247522 | A1 | 11/2006 | Mcgee |
| 2006/0276738 | A1 | 12/2006 | Becker |
| 2006/0293566 | A1 | 12/2006 | Brown |
| 2007/0004958 | A1 | 1/2007 | Ohdaira |
| 2007/0016010 | A1 | 1/2007 | Creighton et al. |
| 2007/0027458 | A1 | 2/2007 | Sixto, Jr. et al. |
| 2007/0043359 | A1 | 2/2007 | Altarac et al. |
| 2007/0073102 | A1 | 3/2007 | Matsuno et al. |
| 2007/0135678 | A1 | 6/2007 | Suzuki |
| 2007/0135685 | A1 | 6/2007 | Cuschieri |
| 2007/0135802 | A1 | 6/2007 | Suzuki |
| 2007/0135803 | A1 | 6/2007 | Belson |
| 2007/0156028 | A1 | 7/2007 | Van Lue et al. |
| 2007/0191670 | A1 | 8/2007 | Spector |
| 2007/0221233 | A1 | 9/2007 | Kawano et al. |
| 2007/0255273 | A1 | 11/2007 | Fernandez et al. |
| 2007/0270629 | A1 * | 11/2007 | Charles ................ A61B 17/122 600/12 |
| 2007/0282311 | A1 | 12/2007 | Scott et al. |

(56) References Cited

U.S. PATENT DOCUMENTS

| | | | |
|---|---|---|---|
| 2008/0081883 | A1 | 4/2008 | King et al. |
| 2008/0097496 | A1 | 4/2008 | Chang et al. |
| 2008/0108860 | A1 | 5/2008 | Bell et al. |
| 2008/0134474 | A1 | 6/2008 | Uryasov |
| 2008/0171907 | A1 | 7/2008 | Long et al. |
| 2008/0243106 | A1 | 10/2008 | Coe et al. |
| 2008/0249534 | A1 | 10/2008 | Gruber et al. |
| 2008/0269779 | A1 | 10/2008 | Cadeddu et al. |
| 2008/0300458 | A1 | 12/2008 | Kim et al. |
| 2009/0004324 | A1 | 1/2009 | Viel et al. |
| 2009/0005636 | A1 | 1/2009 | Pang et al. |
| 2009/0026771 | A1 | 1/2009 | Bevington et al. |
| 2009/0043246 | A1 | 2/2009 | Dominguez |
| 2009/0054909 | A1 | 2/2009 | Farritor et al. |
| 2009/0062772 | A1 | 3/2009 | Wakeford et al. |
| 2009/0076536 | A1 | 3/2009 | Rentschler et al. |
| 2009/0137984 | A1 | 5/2009 | Minnelli |
| 2009/0187074 | A1 | 7/2009 | Saadat et al. |
| 2009/0192344 | A1* | 7/2009 | Bakos .................... A61B 34/73 600/12 |
| 2009/0222029 | A1 | 9/2009 | Gordin et al. |
| 2009/0267717 | A1 | 10/2009 | Baskett |
| 2009/0318762 | A1 | 12/2009 | Segawa et al. |
| 2010/0010306 | A1 | 1/2010 | Kawano et al. |
| 2010/0030026 | A1 | 2/2010 | Uchiyama et al. |
| 2010/0036394 | A1 | 2/2010 | Mintz et al. |
| 2010/0036399 | A1 | 2/2010 | Viola |
| 2010/0081876 | A1 | 4/2010 | Linenkugel et al. |
| 2010/0105984 | A1 | 4/2010 | Brewer et al. |
| 2010/0113872 | A1 | 5/2010 | Asada et al. |
| 2010/0114126 | A1 | 5/2010 | Neff |
| 2010/0137845 | A1 | 6/2010 | Ramstein et al. |
| 2010/0145147 | A1 | 6/2010 | Pinsky et al. |
| 2010/0152539 | A1 | 6/2010 | Ghabrial et al. |
| 2010/0160739 | A1 | 6/2010 | Van Lue |
| 2010/0168523 | A1 | 7/2010 | Ducharme |
| 2010/0174234 | A1 | 7/2010 | Werp et al. |
| 2010/0193566 | A1 | 8/2010 | Scheib et al. |
| 2010/0204727 | A1 | 8/2010 | Dominguez |
| 2010/0217245 | A1 | 8/2010 | Prescott |
| 2010/0237206 | A1 | 9/2010 | Barker |
| 2010/0256636 | A1 | 10/2010 | Fernandez et al. |
| 2010/0268254 | A1 | 10/2010 | Golden et al. |
| 2010/0298645 | A1 | 11/2010 | Deutch |
| 2011/0040152 | A1 | 2/2011 | Kim et al. |
| 2011/0054306 | A1 | 3/2011 | Del Nido et al. |
| 2011/0087223 | A1 | 4/2011 | Spivey |
| 2011/0087224 | A1* | 4/2011 | Cadeddu ................ A61B 34/73 606/49 |
| 2011/0087249 | A1 | 4/2011 | Rodriques et al. |
| 2011/0105848 | A1 | 5/2011 | Sadovsky et al. |
| 2011/0121050 | A1 | 5/2011 | Nicholas et al. |
| 2011/0130787 | A1 | 6/2011 | Cinquin et al. |
| 2011/0184440 | A1 | 7/2011 | Saldinger |
| 2011/0215888 | A1 | 9/2011 | Abbott et al. |
| 2011/0230726 | A1 | 9/2011 | Viola |
| 2011/0230869 | A1 | 9/2011 | Altamirano |
| 2011/0276941 | A1 | 11/2011 | Oi |
| 2011/0283822 | A1 | 11/2011 | Cadeddu et al. |
| 2011/0284014 | A1 | 11/2011 | Cadeddu et al. |
| 2011/0285488 | A1 | 11/2011 | Scott et al. |
| 2011/0295067 | A1 | 12/2011 | Rodriguez Fernandez et al. |
| 2011/0306840 | A1 | 12/2011 | Allen et al. |
| 2011/0313415 | A1* | 12/2011 | Fernandez ........ A61M 25/0127 606/41 |
| 2012/0008535 | A1 | 1/2012 | Kuehnel |
| 2012/0016362 | A1 | 1/2012 | Heinrich et al. |
| 2012/0035416 | A1 | 2/2012 | Fernandez et al. |
| 2012/0053402 | A1 | 3/2012 | Conlon et al. |
| 2012/0053406 | A1 | 3/2012 | Conlon et al. |
| 2012/0065627 | A1 | 3/2012 | Ghabrial et al. |
| 2012/0078292 | A1 | 3/2012 | Banju |
| 2012/0085358 | A1 | 4/2012 | Cadeddu et al. |
| 2012/0101488 | A1 | 4/2012 | Aldridge et al. |
| 2012/0116148 | A1 | 5/2012 | Weinberg et al. |
| 2012/0227748 | A1 | 9/2012 | Sanders |
| 2012/0238796 | A1 | 9/2012 | Conlon |
| 2012/0330089 | A1 | 12/2012 | Ritter et al. |
| 2013/0030462 | A1 | 1/2013 | Keating et al. |
| 2013/0066304 | A1 | 3/2013 | Belson et al. |
| 2013/0085341 | A1 | 4/2013 | Nobis et al. |
| 2013/0090666 | A1 | 4/2013 | Hess et al. |
| 2013/0109267 | A1 | 5/2013 | Schweikardt et al. |
| 2013/0110128 | A1 | 5/2013 | Schostek et al. |
| 2013/0123828 | A1 | 5/2013 | Culmer et al. |
| 2013/0158348 | A1 | 6/2013 | Nobis et al. |
| 2013/0158523 | A1 | 6/2013 | Bergs et al. |
| 2013/0158659 | A1 | 6/2013 | Bergs et al. |
| 2013/0158660 | A1 | 6/2013 | Bergs et al. |
| 2013/0172672 | A1 | 7/2013 | Iddan et al. |
| 2013/0172906 | A1 | 7/2013 | Olson et al. |
| 2013/0226226 | A1 | 8/2013 | Garrison et al. |
| 2013/0245356 | A1 | 9/2013 | Fernandez et al. |
| 2013/0253256 | A1 | 9/2013 | Griffith et al. |
| 2013/0253275 | A1 | 9/2013 | Ransden et al. |
| 2013/0253550 | A1 | 9/2013 | Beisel et al. |
| 2013/0267788 | A1 | 10/2013 | Duan et al. |
| 2013/0289579 | A1 | 10/2013 | Yeung et al. |
| 2013/0289617 | A1 | 10/2013 | Suzuki et al. |
| 2013/0289768 | A1 | 10/2013 | Yeung et al. |
| 2013/0303851 | A1 | 11/2013 | Griffith et al. |
| 2014/0066695 | A1 | 3/2014 | Deutch |
| 2014/0084761 | A1 | 3/2014 | Scott et al. |
| 2014/0135616 | A1 | 5/2014 | Stein et al. |
| 2014/0176797 | A1 | 6/2014 | Silva et al. |
| 2014/0187857 | A1 | 7/2014 | Wilson et al. |
| 2014/0243586 | A1 | 8/2014 | Rohaninejad et al. |
| 2014/0243597 | A1 | 8/2014 | Weisenburgh et al. |
| 2014/0257370 | A1 | 9/2014 | Taylor et al. |
| 2014/0276335 | A1 | 9/2014 | Pate |
| 2014/0277104 | A1 | 9/2014 | Rodriguez-Navarro et al. |
| 2014/0350574 | A1 | 11/2014 | Farritor et al. |
| 2014/0358162 | A1 | 12/2014 | Valdastri et al. |
| 2014/0358229 | A1 | 12/2014 | Bergs et al. |
| 2015/0012010 | A1 | 1/2015 | Adler et al. |
| 2015/0018614 | A1 | 1/2015 | Duan et al. |
| 2015/0141750 | A1 | 5/2015 | Iddan et al. |
| 2016/0038135 | A1 | 2/2016 | Deutch |
| 2016/0120613 | A1 | 5/2016 | Cadeddu et al. |
| 2018/0271603 | A1 | 9/2018 | Nir et al. |
| 2018/0296289 | A1 | 10/2018 | Rodriguez-Navarro et al. |
| 2018/0325604 | A1 | 11/2018 | Atarot et al. |
| 2019/0269394 | A1 | 9/2019 | Deutch |
| 2019/0350575 | A1 | 11/2019 | Deutch |
| 2020/0289140 | A1 | 9/2020 | Rodriguez-Navarro et al. |
| 2021/0290330 | A1 | 9/2021 | Rodriguez-Navarro et al. |
| 2022/0015789 | A1 | 1/2022 | Rodriguez-Navarro |
| 2023/0021246 | A1 | 1/2023 | Rodriguez-Navarro et al. |
| 2023/0106676 | A1 | 4/2023 | Deutch |
| 2023/0277266 | A1 | 9/2023 | Rodriguez-Navarro et al. |
| 2025/0176961 | A1 | 6/2025 | Rodriguez-Navarro et al. |
| 2025/0312053 | A1 | 10/2025 | Rodriguez-Navarro |
| 2025/0325339 | A1 | 10/2025 | Rodriguez-Navarro et al. |

FOREIGN PATENT DOCUMENTS

| | | | |
|---|---|---|---|
| CA | 2733465 | A1 | 9/2011 |
| CN | 2244381 | Y | 1/1997 |
| CN | 101090672 | A | 12/2007 |
| CN | 201079412 | Y | 7/2008 |
| CN | 201091596 | Y | 7/2008 |
| CN | 101534725 | A | 9/2009 |
| CN | 102068288 | A | 5/2011 |
| CN | 102355865 | A | 2/2012 |
| CN | 203953720 | U | 11/2014 |
| DE | 42 12 430 | A1 | 10/1993 |
| DE | 19 534 618 | A1 | 3/1997 |
| DE | 10 2005 006 705 | A1 | 8/2006 |
| DE | 10-2010-010417 | A1 | 9/2011 |
| EP | 1 797 823 | A1 | 6/2007 |
| EP | 1 972 284 | A2 | 9/2008 |
| EP | 2 012 697 | A2 | 1/2009 |
| EP | 2 355 699 | A2 | 8/2011 |
| EP | 2 366 357 | A1 | 9/2011 |

(56) References Cited

FOREIGN PATENT DOCUMENTS

| | | | |
|---|---|---|---|
| EP | 2 381 873 | A2 | 11/2011 |
| EP | 2 391 277 | A0 | 12/2011 |
| EP | 1 942 810 | B1 | 8/2012 |
| EP | 2 571 443 | A2 | 3/2013 |
| EP | 2 595 548 | A0 | 5/2013 |
| EP | 2 842 511 | A1 | 3/2015 |
| JP | 09-192137 | A | 7/1997 |
| JP | 2004-357816 | A | 12/2004 |
| JP | 2005-021576 | A | 1/2005 |
| JP | 4320214 | B2 | 8/2009 |
| JP | 2009-538699 | A | 11/2009 |
| WO | WO-00/51500 | A1 | 9/2000 |
| WO | WO-2005/004734 | A1 | 1/2005 |
| WO | WO-2005/032370 | A1 | 4/2005 |
| WO | WO-2006/071120 | A1 | 7/2006 |
| WO | WO-2007/067231 | A1 | 6/2007 |
| WO | WO-2007/130382 | | 11/2007 |
| WO | WO-2007/142977 | | 12/2007 |
| WO | WO-2007/143162 | | 12/2007 |
| WO | WO-2007/143170 | | 12/2007 |
| WO | WO-2008/039237 | A1 | 4/2008 |
| WO | WO-2008/085919 | | 7/2008 |
| WO | WO-2008/131128 | A1 | 10/2008 |
| WO | WO-2009/008865 | A1 | 1/2009 |
| WO | WO-2009/019288 | | 2/2009 |
| WO | WO-2009/070743 | A1 | 6/2009 |
| WO | WO-2010/056716 | | 5/2010 |
| WO | WO-2010/077561 | A1 | 7/2010 |
| WO | WO-2010/083480 | | 7/2010 |
| WO | WO-2010/089635 | A1 | 8/2010 |
| WO | WO-2011/044468 | | 4/2011 |
| WO | WO-2011/044471 | | 4/2011 |
| WO | WO-2011/091483 | A1 | 8/2011 |
| WO | WO-2011/146691 | | 11/2011 |
| WO | WO2011/146698 | | 11/2011 |
| WO | WO-2011/146709 | | 11/2011 |
| WO | WO-2012/010910 | A1 | 1/2012 |
| WO | WO-2012/031114 | | 3/2012 |
| WO | WO-2012/033925 | A1 | 3/2012 |
| WO | WO-2012/048102 | | 4/2012 |
| WO | WO-2013/096470 | A1 | 6/2013 |
| WO | WO-2014/133751 | A1 | 9/2014 |
| WO | WO-2014/159023 | A1 | 10/2014 |
| WO | WO-2014/163872 | A1 | 10/2014 |
| WO | WO-2015/112645 | A1 | 7/2015 |
| WO | WO-2015/142953 | A1 | 9/2015 |
| WO | WO-2016/168380 | A1 | 10/2016 |

OTHER PUBLICATIONS

Best, S.L. et al. (2010). "Development of magnetic anchoring and guidance systems for minimally invasive surgery," Indian J. of Urology 26:418-422.
Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.
Best, S.L. et al. (2010). "MAGS Instrumentation for Less/Notes: Lack of Histologic Damage After Prolonged Magnetic Coupling Across the Abdominal Wall," World Congress of Endourology, PS2-4, Chicago IL, Sep. 2010.
Best, S.L. et al. (2008). "Maximizing Coupling Strength of Magnetically Anchored Notes Instruments: How Thick Can We Go?" Surgical Endoscopy, vol. 22: S241.
Cadeddu, J.A. et al. (2002). "Transabdominal magnetic anchoring system for trocar-less laparoscopic surgery," J. of Urology, vol. 167, No. 4, Supplement, Abstract No. 16, 1 total page.
Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.
Dominguez (2007). "Colecistectomia con un trocar asistida por imanes de neodimio. Reporte de un caso." *Asociacion Mexicana de Cirugia Endo*. vol. 8. No. 4, pp. 172-176 (with English Abstract).
Dominguez, G. et al. (2009). "Retraction and triangulation with neodymium magnetic forceps for single-port laparoscopic cholecystectomy," Surg. Endosc. 23:1660-1666.
Duchene, D.A. et al. (2004). "Magnetic positioning system for trocarless laparoscopic instruments," J. of Endourology 18:693.
Extended European Search Report mailed on Jul. 20, 2016, for EP Application No. 14 778 895.4, filed on Feb. 25, 2014, 7 pages.
Extended European Search Report mailed on Dec. 20, 2016, for EP Application No. 09 839 564.3, filed on Oct. 1, 2009, 11 pages.
Extended European Search Report mailed on Sep. 27, 2017, for EP Application No. 15 741 055.6, filed on Jan. 21, 2015, 9 pages.
Extended European Search Report mailed on Oct. 30, 2018, for EP Application No. 16 780 691.8, filed on Apr. 13, 2016, 6 pages.
Extended European Search Report mailed on Nov. 26, 2018, for EP Application No. 16 780 688.4, filed on Sep. 26, 2017, 9 pages.
Extended European Search Report mailed on Jul. 22, 2019, for EP Application No. 19 151 941.2, filed on Feb. 25, 2014, 6 pages.
Extended European Search Report mailed on Aug. 22, 2019, for EP Application No. 17 736 483.3, filed on Jan. 6, 2017, 8 pages.
Extended European Search Report mailed on May 31, 2013, for EP Application No. 08 853 840.0 filed on Nov. 26, 2008, 11 pages.
Extended European Search Report mailed on Jan. 4, 2022, for EP Application No. 21 189 505.7, filed on Apr. 13, 2016, 10 pages.
Extended European Search Report mailed on Jan. 18, 2022, for EP Application No. 21 187 437.5, filed on Apr. 13, 2016, 6 pages.
Extended European Search Report mailed on Feb. 17, 2022, for EP Application No. 21 189 492.8, filed on Feb. 25, 2014, 6 pages.
Fernandez, R. et al. (2012). "Determining a Performance Envelope for Capture of Kidney Stones Functionalized with Superparamagnetic Particles," Journal of Endourology, 26(9):1227-30.
Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, Bed vol. 55, pp. 157-158.
Final Office Action mailed on Sep. 16, 2016, for U.S. Appl. No. 14/704,828, filed May 5, 2015, 10 pages.
Final Office Action mailed on Jan. 25, 2016, for U.S. Appl. No. 14/337,082, filed Jul. 21, 2014, 9 pages.
Final Office Action mailed on Dec. 28, 2016, for U.S. Appl. No. 14/200,302, filed Mar. 7, 2014, 15 pages.
Final Office Action mailed on Sep. 6, 2017, for U.S. Appl. No. 14/200,302, filed Mar. 7, 2014. 9 pages.
Final Office Action mailed on Mar. 7, 2018, for U.S. Appl. No. 15/098,262, filed Apr. 13, 2016, 10 pages.
Final Office Action mailed on Feb. 26, 2019, for U.S. Appl. No. 15/195,898, filed Jun. 28, 2016, 9 pages.
Final Office Action mailed on Nov. 25, 2020, for U.S. Appl. No. 15/728,297, filed Oct. 9, 2017, 11 pages.
Final Office Action mailed on Sep. 3, 2021, for U.S. Appl. No. 16/149,576, filed Oct. 2, 2018, 14 pages.
Final Office Action mailed on Oct. 26, 2021, for U.S. Appl. No. 16/419,363, filed May 22, 2019, 7 pages.
Final Office Action mailed on Oct. 28, 2021, for U.S. Appl. No. 16/528,878, filed Aug. 1, 2019, 8 pages.
Final Office Action mailed on Feb. 7, 2022, for U.S. Appl. No. 16/008,976, filed Jun. 14, 2018, 20 pages.
Final Office Action mailed on May 2, 2022, for U.S. Appl. No. 15/728,297, filed Oct. 9, 2017, 13 pages.
Final Office Action mailed on Mar. 16, 2023, for U.S. Appl. No. 16/008,976, filed Jun. 14, 2018, 21 pages.
International Search Report mailed on Jul. 30, 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report mailed on May 4, 2015, for PCT Application No. PCT/US2015/012319, filed on Jan. 21, 2015, 2 pages.
International Search Report mailed on Jul. 18, 2014, for PCT Application No. PCT/US2014/018307, filed on Feb. 25, 2014, 4 pages.

(56) References Cited

OTHER PUBLICATIONS

International Search Report mailed on Jul. 15, 2016, for PCT Application No. PCT/US2016/027385, filed on Apr. 13, 2016, 2 pages.
International Search Report mailed on Aug. 22, 2016, for PCT Application No. PCT/US2016/027390, filed on Apr. 13, 2016, 4 pages.
International Search Report mailed on Apr. 3, 2017, for PCT Application No. PCT/US2017/012628, filed on Jan. 6, 2017, 2 pages.
International Search Report mailed on Apr. 9, 2009, for PCT Application No. PCT/US2008/084991, filed on Nov. 26, 2008, 3 pages.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, P246, National Harbor, MD, Apr. 2010.
Milki, A.A. et al. (1998). "Vaginal ultrasound probe coverage leakage: implications for patient care, fertility and sterility, American Society for Reproductive Medicine," Fertil. Steril. 69:409-411.
Non-Final Office Action mailed on May 25, 2016, for U.S. Appl. No. 14/200,302, filed Mar. 7, 2014, 12 pages.
Non-Final Office Action mailed on May 21, 2013, for U.S. Appl. No. 13/132,185, filed Aug. 17, 2011, 18 pages.
Non-Final Office Action mailed on Jul. 21, 2016, for U.S. Appl. No. 14/337,082, filed Jul. 21, 2014, 9 pages.
Non-Final Office Action mailed on Jul. 13, 2015, for U.S. Appl. No. 14/337,082, filed Jul. 21, 2014, 10 pages.
Non-Final Office Action mailed on Jan. 25, 2016, for U.S. Appl. No. 14/704,828, filed May 5, 2015, 9 pages.
Non-Final Office Action mailed on Jul. 14, 2015, for U.S. Appl. No. 14/704,828, filed May 5, 2015, 10 pages.
Non-Final Office Action mailed on Oct. 24, 2013, for U.S. Appl. No. 14/019,370, filed Sep. 5, 2013, 7 pages.
Non-Final Office Action mailed on Oct. 22, 2015, for U.S. Appl. No. 14/019,404, filed Sep. 5, 2013, 6 pages.
Non-Final Office Action mailed on May 22, 2017, for U.S. Appl. No. 14/200,302, filed Mar. 7, 2014, 14 pages.
Non-Final Office Action mailed on May 3, 2017, for U.S. Appl. No. 14/704,828, filed May 5, 2015, 8 pages.
Non-Final Office Action mailed on Jul. 24, 2017, for U.S. Appl. No. 15/098,262, filed Apr. 13, 2016, 9 pages.
Non-Final Office Action mailed on Jun. 29, 2018, for U.S. Appl. No. 15/195,898, filed Jun. 28, 2016, 9 pages.
Non-Final Office Action mailed on Sep. 17, 2019, for U.S. Appl. No. 15/728,297, filed Oct. 9, 2017, 8 pages.
Non-Final Office Action mailed on Mar. 3, 2020, for U.S. Appl. No. 15/728,302, filed Oct. 9, 2017, 14 pages.
Non-Final Office Action mailed on Mar. 6, 2020, for U.S. Appl. No. 15/926,578, filed Mar. 20, 2018, 9 pages.
Non-Final Office Action mailed on Dec. 22, 2020, for U.S. Appl. No. 16/149,576, filed Oct. 2, 2018, 10 pages.
Non-Final Office Action mailed on May 12, 2021, for U.S. Appl. No. 16/008,976, filed Jun. 14, 2018, 15 pages.
Non-Final Office Action mailed on Apr. 29, 2021, for U.S. Appl. No. 16/419,363, filed May 22, 2019, 9 pages.
Non-Final Office Action mailed on Apr. 15, 2021, for U.S. Appl. No. 16/528,878, filed Aug. 1, 2019, 6 pages.
Non-Final Office Action mailed on Sep. 15, 2021, for U.S. Appl. No. 15/728,297, filed Oct. 9, 2017, 11 pages.
Non-Final Office Action mailed on Aug. 5, 2022, for U.S. Appl. No. 16/008,976, filed Jun. 14, 2018, 18 pages.
Non-Final Office Action mailed on Oct. 12, 2022, for U.S. Appl. No. 16/746,448, filed Jan. 17, 2020, 16 pages.
Non-Final Office Action mailed on Oct. 28, 2022, for U.S. Appl. No. 17/161,185, filed Jan. 28, 2021, 9 pages.
Notice of Allowance mailed on Feb. 14, 2014, for U.S. Appl. No. 14/019,370, filed Sep. 5, 2013, 7 pages.
Notice of Allowance mailed on Mar. 14, 2014, for U.S. Appl No. 13/132,185, filed Aug. 17, 2011, 7 pages.
Notice of Allowance mailed on Mar. 14, 2016, for U.S. Appl. No. 14/019,404, filed Sep. 5, 2013, 7 pages.
Notice of Allowance mailed on May 3, 2017, for U.S. Appl. No. 14/337,082, filed Jul. 21, 2014, 7 pages.
Notice of Allowance mailed on Aug. 25, 2017, for U.S. Appl. No. 14/337,082, filed Jul. 21, 2014, 7 pages.
Notice of Allowance mailed on Nov. 22, 2017, for U.S. Appl. No. 14/200,302, filed Mar. 7, 2014, 5 pages.
Notice of Allowance mailed on Jan. 19, 2018, for U.S. Appl. No. 14/704,828, filed May 5, 2015, 7 pages.
Notice of Allowance mailed on Aug. 24, 2018, for U.S. Appl. No. 15/098,262, filed Apr. 13, 2016, 9 pages.
Notice of Allowance mailed on Sep. 11, 2019, for U.S. Appl. No. 15/195,898, filed Jun. 28, 2016, 9 pages.
Notice of Allowance mailed on Nov. 26, 2019, for U.S. Appl. No. 15/195,898, filed Jun. 28, 2016, 6 pages.
Notice of Allowance mailed on Sep. 29, 2020, for U.S. Appl. No. 15/728,302, filed Oct. 9, 2017, 8 pages.
Notice of Allowance mailed on Feb. 5, 2021, for U.S. Appl. No. 15/926,578, filed Mar. 20, 2018, 9 pages.
Notice of Allowance mailed on Feb. 14, 2022, for U.S. Appl. No. 16/149,576, filed Oct. 2, 2018, 9 pages.
Notice of Allowance mailed on Apr. 7, 2022, for U.S. Appl. No. 16/528,878, filed Aug. 1, 2019, 6 pages.
Notice of Allowance mailed on Apr. 20, 2022, for U.S. Appl. No. 16/419,363, filed May 22, 2019, 6 pages.
Notice of Allowance mailed on Oct. 19, 2022, for U.S. Appl. No. 15/728,297, filed Oct. 9, 2017, 8 pages.
Notice of Allowance mailed on Apr. 3, 2023, for U.S. Appl. No. 16/746,448, filed Jan. 17, 2020, 12 pages.
Odwin, C.S. et al. (1990). "Prove covers and disinfectants for transvaginal transducers," JDMS 6:130-135.
Park, S. et al. (2007). "Trocar-less instrumentation for laparoscopy magnetic positioning of intra-abdominal camera and retractor," Surgical Technique 245:379-384.
Raman, J. (2009). "Complete Transvaginal NOTES Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Minimally Invasive Robotic Association (MIRA) Conference on Robotic Surgery, Innsbruck, Austria, Dec. 2005.
Scott, D.J. et al. (2007). "Completely transvaginal Notes cholecystectomy using magnetically anchored instruments," Surg. Endosc. 21:2308-2316.
Scott, D. et al. (2008). "Optimizing Magnetically Anchored Camera, Light Source, Graspers, and Cautery Dissector for Transvaginal Notes Cholecystectomy," Surgical Endoscopy 22:S244.
Scott, D. et al. (2008). "Randomized Comparison of Laparoscopic, Flexible Endoscopic, and Wired and Wireless Magnetic Notes Cameras on Ex-Vivo and In-Vivo Surgical Performance," Gastrointestinal Endoscopy, vol. 67: AB115.
Scott, D. et al. (2008). "Transvaginal Single Access "Pure" Notes Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.

(56) References Cited

OTHER PUBLICATIONS

Scott, D. et al. (2007). "Short-Term Survival Outcomes Following Transvaginal Notes Cholecystectomy Using Magnetically Anchored Instruments," Gastrointestinal Endoscopy, vol. 65: AB109.
Supplemental Notice of Allowability mailed on Dec. 18, 2020, for U.S. Appl. No. 15/728,302, filed Oct. 9, 2017, 3 pages.
Swain, C. et al. (2008). "Linear Stapler Formation of Ileo-Rectal, Entero-Enteral and Gastrojejunal Anastomoses During Dual and Single Access "Pure" Notes Procedures: Methods, Magnets and Stapler Modifications," Gastrointestinal Endoscopy, vol. 67: AB119.
Swain, P. et al. (2008). "Wireless Endosurgery for Notes," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-858.
Tang, S. (2008). "Live Video Manipulator for Endoscopy and Notes," Gastrointestinal Endoscopy 68:559-564.
Tillander, H. (1951). "Magnetic guidance of a catheter with articulated steel tip," Acta Radiologica pp. 62-64.
Wikipedia (2015). "Stainless Steel," retrieved from https://en.wikipedia.org/wiki/Stainless_steel, 13 Ipages.
Written Opinion of the International Searching Authority mailed on Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010.
Written Opinion of the International Searching Authority mailed on Jul. 18, 2014, for PCT Application No. PCT/US2014/018307, filed on Feb. 25, 2014, 5 pages.
Written Opinion of the International Searching Authority mailed on May 4, 2015, for PCT Application No. PCT/US2015/012319, filed on Jan. 21, 2015, 5 pages.
Written Opinion of the International Searching Authority mailed on Jul. 15, 2016, for PCT Application No. PCT/US2016/027385, filed on Apr. 13, 2016, 11 pages.
Written Opinion of the International Searching Authority mailed on Aug. 22, 2016, for PCT Application No. PCT/US2016/027390, filed on Apr. 13, 2016, 9 pages.
Written Opinion of the International Searching Authority mailed on Apr. 3, 2017, for PCT Application No. PCT/US2017/012628, filed on Jan. 6, 2017, 7 pages.
Written Opinion of the International Searching Authority mailed on Apr. 9, 2009, for PCT Application No. PCT/US2008/084991, filed on Nov. 26, 2008, 12 pages.
Zeltser, I.S et al. (2007). "Single trocar laparoscopic nephrectomy using magnetic anchoring and guidance system in the porcine model," J. of Urology 178:1-4.
U.S. Appl. No. 61/113,495, filed Nov. 25, 2008, by Fernandez et al.
EP Application No. 24 208 902.7, Extended European Search Report mailed Feb. 21, 2025, Applicant Levita Magnetics International Corp., 9 pages.
U.S. Appl. No. 17/161,185, Corrected Notice of Allowability mailed Jul. 12, 2023, Inventor Rodriguez-Navarro, Alberto et al., 4 pages.
U.S. Appl. No. 16/008,976, Corrected Notice of Allowability mailed Dec. 12, 2024, Inventor Rodriguez-Navarro, Alberto et al., 2 pages.
U.S. Appl. No. 16/008,976, Final Office Action mailed May 31, 2024, Inventor Rodriguez-Navarro, Alberto et al., 12 pages.
U.S. Appl. No. 16/008,976, Non-Final Office Action mailed Oct. 16, 2023, Inventor Rodriguez-Navarro, Alberto et al., 23 pages.
U.S. Appl. No. 17/332,876, Non-Final Office Action mailed Feb. 16, 2024, Inventor Rodriguez-Navarro, Alberto, 10 pages.
U.S. Appl. No. 17/836,867, Non-Final Office Action mailed Jul. 18, 2024, Inventor Rodriguez-Navarro, Alberto et al., 10 pages.
U.S. Appl. No. 18/220,192, Non-Final Office Action mailed Sep. 13, 2024, Inventor Rodriguez-Navarro, Alberto et al., 11 pages.
U.S. Appl. No. 17/881,452, Non-Final Office Action mailed Jun. 13, 2025, Inventor Deutch, Todd, 8 pages.
U.S. Appl. No. 17/161,185, Notice of Allowance mailed Apr. 10, 2023, Inventor Rodriguez-Navarro, Alberto et al., 9 pages.
U.S. Appl. No. 18/346,089, Notice of Allowance mailed Aug. 14, 2024, Inventor Rodriguez-Navarro, Alberto et al., 14 pages.
U.S. Appl. No. 17/332,876, Notice of Allowance mailed Sep. 5, 2024, Inventor Rodriguez-Navarro, Alberto, 7 pages.
U.S. Appl. No. 16/008,976, Notice of Allowance mailed Nov. 29, 2024, Inventor Rodriguez-Navarro, Alberto et al., 8 pages.
U.S. Appl. No. 17/836,867, Notice of Allowance mailed Feb. 26, 2025, Inventor Rodriguez-Navarro, Alberto et al., 8 pages.
U.S. Appl. No. 18/220,192, Notice of Allowance mailed Mar. 26, 2025, Inventor Rodriguez-Navarro, Alberto et al., 9 pages.

* cited by examiner

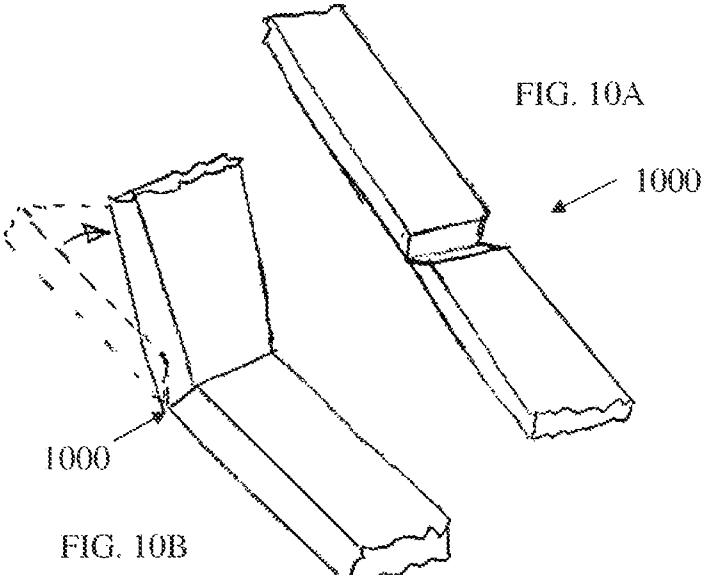
FIG. 10A
FIG. 10B
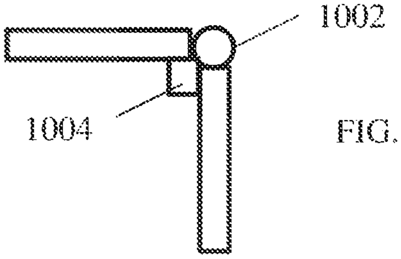
FIG. 10C

RETRACTOR SYSTEMS, DEVICES, AND METHODS FOR USE

CROSS-REFERENCE TO RELATED APPLICATIONS

This application is a continuation of U.S. patent application Ser. No. 15/728,297, filed on Oct. 9, 2017, which is a continuation of International Patent Application No. PCT/US2016/027385, filed on Apr. 13, 2016, which claims priority to U.S. Provisional Application No. 62/146,924, filed on Apr. 13, 2015, the content of each of which is hereby incorporated by reference in its entirety.

FIELD

This invention relates generally to minimally invasive surgery, and more specifically to a new and useful retractor system, device, and method for use.

BACKGROUND

Moving organs within a patient is often required to perform internal surgery. For instance, moving one organ may provide access and/or visualization of another organ undergoing surgical treatment, or it may be necessary to move and manipulate an organ to surgically treat that organ. Additionally, to minimize trauma during minimally invasive surgery, it is often desirable to operate through as few incisions as possible, while maintaining access to the organs being moved and/or treated. Typically, such minimally invasive surgery involves inserting tools through a trocar that provides access into a patient (e.g., through the abdominal wall and into the abdominal cavity, or through another wall of the patient) into a surgical site.

Displacing internal organs from a surgical site during minimally invasive surgery is typically performed with a rod-like retractor with various bends, hooks, and/or grasping mechanisms to manipulate organs. Since a trocar port is reserved to provide access for surgical tools, these retractors must be delivered to the surgical site through separate incisions, which increases patient pain, recovery time, and scarring. Additionally, once delivered, the retractors have limited maneuverability due to their single entry point into the patient. The retractors may be removed and reinserted through a new incision, but this repositioning further increases patient trauma. Furthermore, internal organs are fragile and tend to be heavy and have slippery surfaces, and many current retractors tend to inflict damage on internal organs during organ retraction. Due at least in part to these inadequacies, current retractor systems, devices, and methods are less than ideal for retracting internal organs during minimally invasive surgery. It may therefore be useful to find improved ways to support and/or move an internal organ.

BRIEF SUMMARY

Described here are devices, systems, and methods for moving an internal organ of a patient, such as during minimally-invasive surgery. In some variations, a retractor for supporting at least a portion of an internal organ of a patient may comprise a retractor body comprising at least a first magnetic portion. The retractor body may comprise a low-profile configuration and an expansive configuration for engaging at least a portion of the internal organ. In response to an applied magnetic force, the retractor body is configured to exert a force on at least a portion of the internal organ.

In some variations, the retractor body may be biased toward the low-profile configuration or the expansive configuration. In some variations, in response to the applied magnetic force, the retractor body may transition between the low-profile configuration and the expansive configuration.

In some variations, the retractor body may further comprise a plurality of retractor body elements arranged in series. The retractor body in the low-profile configuration may generally be linear. In some of these variations, the retractor body may further comprise a connecting element that connects at least a portion of the plurality of retractor body elements. In some of these variations, the connecting element may be threaded through each of the retractor body elements. In some variations, each retractor body element may be directly coupled to at least one other retractor body element. In some variations, the retractor body in the expansive configuration may be a coil. In some variations, the retractor body in the expansive configuration may be curvilinear and may be configured to suspend at least a portion of the internal organ.

In some variations, the retractor body in the expansive configuration may define a platform. In some variations, the retractor body may comprise a plurality of linkage members that are substantially overlapped with one another in the low-profile configuration, and spread apart from one another in the expansive configuration. In some variations, the retractor may further comprise a membrane that extends between at least two of the linkage members. In some variations, the plurality of linkage members may be arranged in a zig-zag. In some variations, the plurality of linkage members may be arranged in a cross.

In some variations, the retractor body in the expansive configuration may define a cradle (e.g., concave surface) for receiving at least a portion of the internal organ between overlapping portions of the retractor body (e.g., sandwiching or at least partially encompassing the internal organ between portions of the retractor body). The cradle may comprise a first cradle portion configured to engage at least a portion of the internal organ and a second cradle portion. A magnetic portion may be disposed on the second cradle portion. In some variations, the second cradle portion may be opposite the first cradle portion. In some variations, the second cradle portion may be configured to engage an internal wall of the patient. In some variations, the retractor body may further comprise a flexible sheet that is curved when the retractor body is in the expansive configuration. In some variations, the retractor body may further comprise a linkage that is collapsed when the retractor body is in the low-profile configuration and is expanded when the retractor body is in the expansive configuration.

In some variations, the retractor body may further comprise a first elongated body member comprising a first end configured to engage the internal organ. In some variations, the first elongated body member may be substantially rigid. In some variations, the first elongated body member may comprise a second end on which the magnetic portion may be disposed. In some variations, the retractor body may further comprise a second elongated body member coupled to the first elongated body member. In some of these variations, the second elongated body member may comprise a second magnetic portion disposed on a first end of the second elongated body member, and a third magnetic portion disposed on a second end of the second elongated body member. In some of these variations, the first magnetic portion may have a first polarity and the second and third magnetic portions may have a second polarity opposite the first polarity. In some variations, the second elongated body member may be substantially rigid. In some variations, the second elongated body member may be flexible. In some variations, the retractor body may further comprise a membrane coupled to at least one of the first and second elongated body members. In some of these variations, the membrane may comprise openings.

In some variations, the retractor body may be at least partially made of a magnetic material. In some variations, the first magnetic portion may comprise at least one magnetic mass coupled to the retractor body. In some variations, in the expansive configuration the retractor body may define a substantially planar surface. The retractor body may be configured to exert a force on at least a portion of the internal organ in a direction substantially normal to the substantially planar surface. In some variations, in the expansive configuration the retractor body may define a substantially planar surface. The retractor body may be configured to exert a force on at least a portion of the internal organ in a direction not normal to the substantially planar surface.

In some variations, a system for supporting and/or moving at least a portion of an internal organ of a patient may comprise a retractor comprising at least one magnetic portion and a magnetic control component. The retractor may operate between a first low-profile configuration for passing through an incision into a surgical site within the patient and a second expansive configuration for engaging at least a portion of the internal organ. The magnetic control component may be placed over the surgical site external to the patient and induce a magnetic field to draw at least a portion of the retractor body toward the magnetic control component. In some variations, the retractor in the first configuration may be sized and configured to be passed through a laparoscopic trocar. In some variations, the retractor in the second configuration may engage with the internal organ to enable displacement of the internal organ from the surgical site. In some variations, the retractor in the second configuration may be generally planar. In some variations, the retractor in the second configuration may form a platform. In some variations, the retractor may comprise a membrane. In some variations, the retractor may comprise a plurality of linkage members. In some variations, the retractor in the second configuration may form a cradle. In some variations, the retractor may comprise a plurality of magnetic portions. In some variations, the retractor in the second configuration may suspend at least a portion of the internal organ. In some variations, the retractor may be biased toward the second configuration.

In some variations, a method of support and/or moving at least a portion of an internal organ of a patient may comprise passing a retractor in a first low-profile configuration through an incision into a surgical site within the patient. The retractor may comprise at least one magnetic portion. The retractor within the patient may be transitioned to a second expansive configuration. The internal organ may be engaged with the retractor. A magnetic control component may be placed over the surgical site external to the patient. At least a portion of the retractor may be drawn toward the magnetic control component by inducing a magnetic field that interacts with the magnetic portion.

In some variations, transitioning the retractor to the second configuration may comprise manipulating at least one magnetic portion with the magnetic field. In some variations, transitioning the retractor to the second configuration may comprise releasing a restraint on the retractor and allowing a bias in the retractor to transition the retractor to the second configuration. In some variations, engaging the internal organ with the retractor may comprise supporting an underside of the internal organ with the retractor. In some variations, drawing at least a portion of the internal organ toward the magnetic control component may comprise attracting a second side of the retractor. In some variations, drawing at least a portion of the internal organ toward the magnetic control component may comprise tilting at least a portion of the internal organ with the retractor. In some of these variations, tilting at least a portion of the internal organ may comprise drawing a first portion of the retractor engaged with the internal organ toward the magnetic control component and repelling a second portion of the retractor not engaged with the internal organ away from the magnetic control component. In some variations, tilting at least a portion of the internal organ may comprise drawing a first portion of the retractor engaged with the internal organ toward the magnetic control component and engaging a second portion of the retractor with an internal wall of the patient. In some variations, the method may further comprise transitioning the retractor from the second configuration to the first configuration. In some of these variations, transitioning the retractor from the second configuration to the first configuration may comprise administering a restraint on the retractor to confine the retractor in the first configuration. In some variations, at least a portion of the internal organ may be pulled toward the magnetic control component by the retractor.

In some variations, a method of moving and/or supporting at least a portion of an internal organ within a cavity of a patient may comprise engaging at least a portion of the internal organ with a retractor. The retractor may comprise a first end comprising a magnetic portion and a second end. A magnetic field may be applied to the retractor using a magnetic control component located external to the patient. The first end of the retractor may move at least the portion of the internal organ. The second end of the retractor may be in contact with an interior wall of the cavity.

In some variations, a retractor for supporting and/or moving at least a portion of an internal organ of a patient may comprise a cradle comprising a first side and a second side for receiving at least a portion of the internal organ. The second side may extend longer than the first side. The first side may comprise a magnetic portion.

In some variations, a method for supporting and/or moving at least a portion of an internal organ may comprise inserting a retractor comprising a magnetic portion into a body cavity of the patient. The retractor may comprise a low-profile configuration and an expansive configuration. A magnetic force may be applied to the magnetic portion of the retractor to cause the retractor to engage the internal organ.

In some variations, the method may comprise moving the internal organ using the retractor. The direction of movement of the internal organ may vary as the internal organ is moved. In some variations, the direction of movement of the internal organ is orthogonal to a surface of the retractor in the expansive configuration. In some variations, the direction of movement of the internal organ may comprise a component parallel to a surface of the retractor in the expansive configuration and a component perpendicular to the surface of the retractor in the expansive configuration. The component parallel to the surface of the retractor may be non-zero.

In some variations, a retractor may comprise a retractor body configured to transition between a low-profile configuration and an expansive configuration for engaging at least a portion of the tissue. The retractor body may comprise a first magnetic portion, and the retractor body may be configured to move and/or support at least a portion of the tissue in response to an applied magnetic force.

In some variations, the low-profile configuration may comprise a first surface area and the expansive configuration comprises a second surface area. The second surface area may be larger than the first surface area. In some variations, the retractor body may be biased toward the low-profile configuration or the expansive configuration. In some variations, the retractor body may transition between the low-profile configuration and the expansive configuration in response to the applied magnetic force. In some variations, the retractor body may comprise a first portion and a second portion. The first portion may overlap the second portion in the expansive configuration. In some variations, the retractor body may comprise a second magnetic portion. In some variations, the first magnetic portion and the second magnetic portion may have different polarities. In some variations, the retractor body may comprise a linkage comprising a first linkage member and a second linkage member. In some variations, the transition between the low-profile configuration and the expansive configuration may rotate the first linkage member relative to the second linkage member. In some variations, the second linkage member may comprise a flexible material. In some variations, the retractor body may comprise a membrane.

In some variations, a system for supporting and/or moving at least a portion of an internal organ of a patient may comprise a retractor comprising a plurality of magnetic portions. The retractor may operate between a first low-profile configuration for passing through an incision into a surgical site within the patient and a second expansive configuration for engaging at least a portion of the internal organ. A plurality of magnetic control components may be placed over the surgical site external to the patient and induce a corresponding magnetic field to draw at least a portion of the retractor toward the magnetic control component. In some variations, at least some of the plurality of magnetic control components may be controlled independently. In some variations, each of the plurality of magnetic control components may apply the magnetic field to a respective portion of the retractor.

BRIEF DESCRIPTION OF THE DRAWINGS

FIGS. 10A and 10B are perspective views of a straight configuration and a bent configuration, respectively, of one variation of a hinge joint in one variation of a retractor. FIG. 10C is aside view schematic representation of a hinge joint in one variation of a retractor.

DETAILED DESCRIPTION

Disclosed herein are retractor systems, devices, and methods for use during minimally invasive surgery. The retractor devices and systems described herein may be used to retract or otherwise support and/or move internal organs of a patient during minimally-invasive procedures, including but not limited to laparoscopic surgery or other suitable surgical procedures. In particular, retractors described herein may be inserted into a patient and retract tissue to displace it from a surgical site inside the patient, and/or otherwise engage tissue to increase surgical access to that tissue. Further, the retractors described herein may be configured to be maintained in position without requiring a handle or grasper.

In general, retractor systems described here may comprise a retractor and a magnetic control component. In some variations, the retractor may have a first configuration and a second configuration. The retractor in the first configuration may be low-profile such that it is sized and configured to be passed through an incision into a body cavity (e.g., the abdominal cavity) near a surgical site within a patient. After the retractor is passed into the patient, the retractor may be located away from the incision, thereby permitting other tools or devices to access the surgical site through the same incision and lowering the total number of incisions that are needed for the surgical procedure. After the retractor is within the body cavity and away from the incision site, the retractor may change from the first configuration to the second configuration. The retractor in the second configuration may be expansive such that it is sized and configured to engage tissue (e.g., an internal organ) of a patient. The retractors described herein may comprise one or more magnetic portions.

A magnetic control component of the retractor system may be sized and configured to be located external to the patient (e.g., over or near the surgical site). The magnetic control component may be configured to generate a magnetic field that draws at least a portion of the retractor toward the magnetic control component, thereby moving the engaged internal organ (e.g., retracting or otherwise displacing the organ). The magnetic control component may additionally or alternatively be configured to maintain the position of the retractor and the internal organ during a surgical procedure.

Figure 1A:
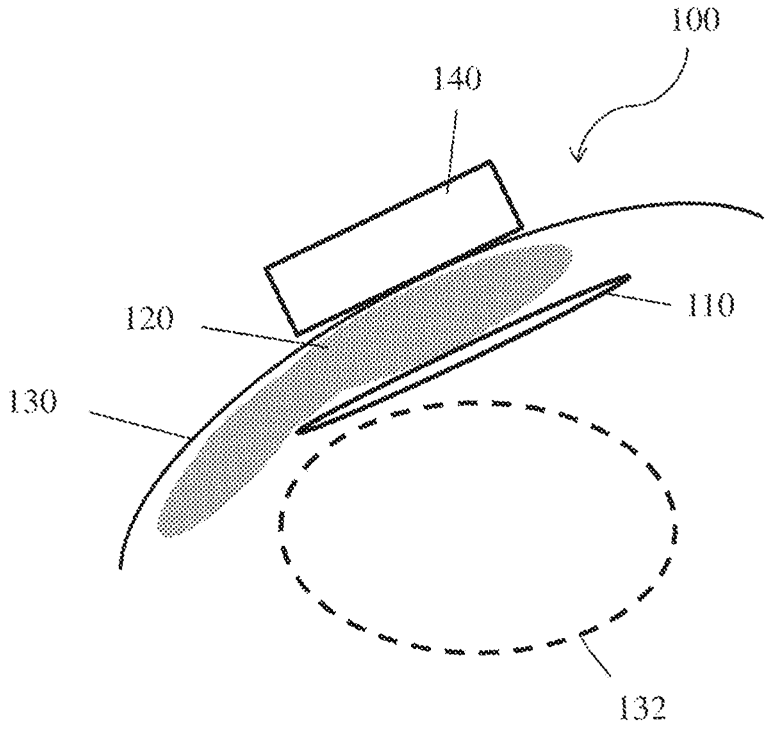
FIGS. 1A-1D are schematic representations of an exemplary implementation of a magnetic retractor system.

As shown, for example, in the general schematic of FIG. 1A, a retractor system (100) may comprise a retractor (110) and magnetic control component (140). The retractor (110) may engage an internal organ or other tissue (120). The external magnetic control component (140) may be positioned outside patient wall (130) and induce a magnetic field configured to attract the retractor (110) and tissue (120) toward the magnetic control component (140) or other external magnet, thereby improving access to surgical site (132) for other systems and/or devices. The retractor (110) and magnetic control component (140) may maintain the position of the tissue (120) in a desired position, such as to maintain surgical site (132) access during a surgical procedure. The retractor devices and systems described herein may be used to retract any suitable tissue, organ, and/or structure, such as but not limited to a patient's lung, intestine, stomach, liver, other internal tissue, or any combination thereof.

I. Devices

Retractor

Generally, retractors described herein may be configured to engage tissue (e.g., an internal organ) of a patient and be manipulated through an applied magnetic field (e.g., from an external magnet such as one or more magnetic control components described below) to retract or otherwise move the tissue, and/or maintain the position of the tissue in order to maintain better access to a surgical site. The retractor may include a retractor body and at least one portion that is responsive to a magnetic field (described here as a "magnetic portion"), such that the retractor may be manipulated by an external magnet. In some variations, manipulation of the retractor engaged with tissue may exert a force and/or move the tissue.

Figure 1B:
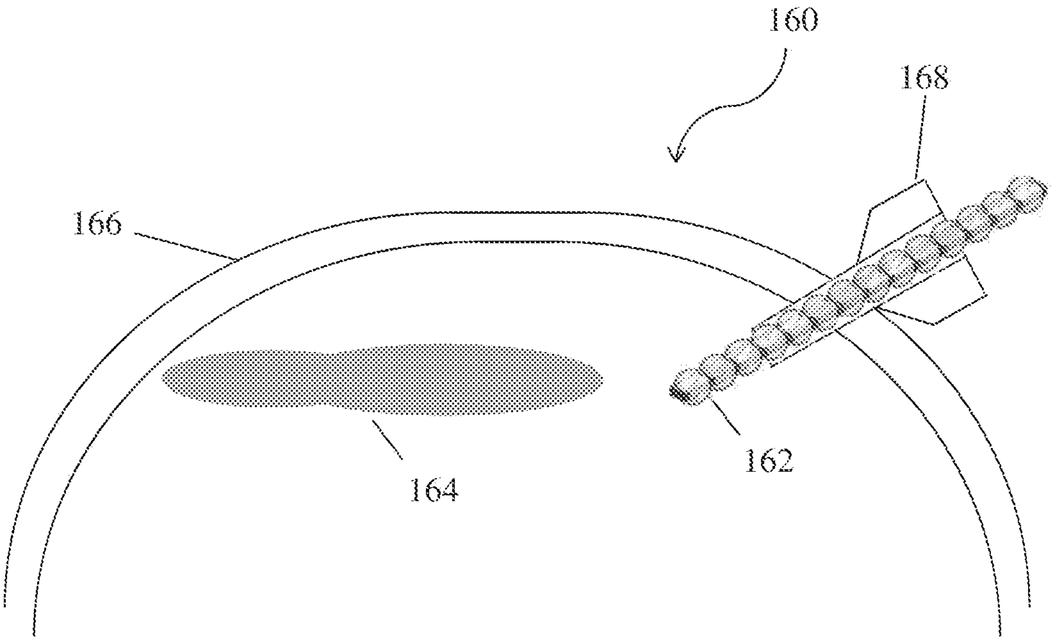
Figure 1C:
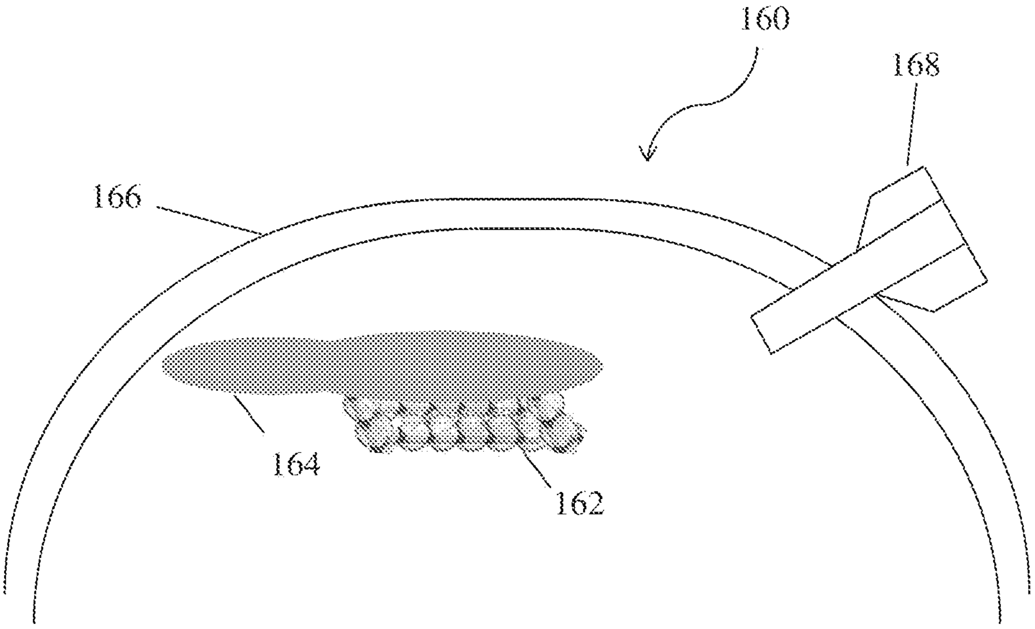
Figure 1D:
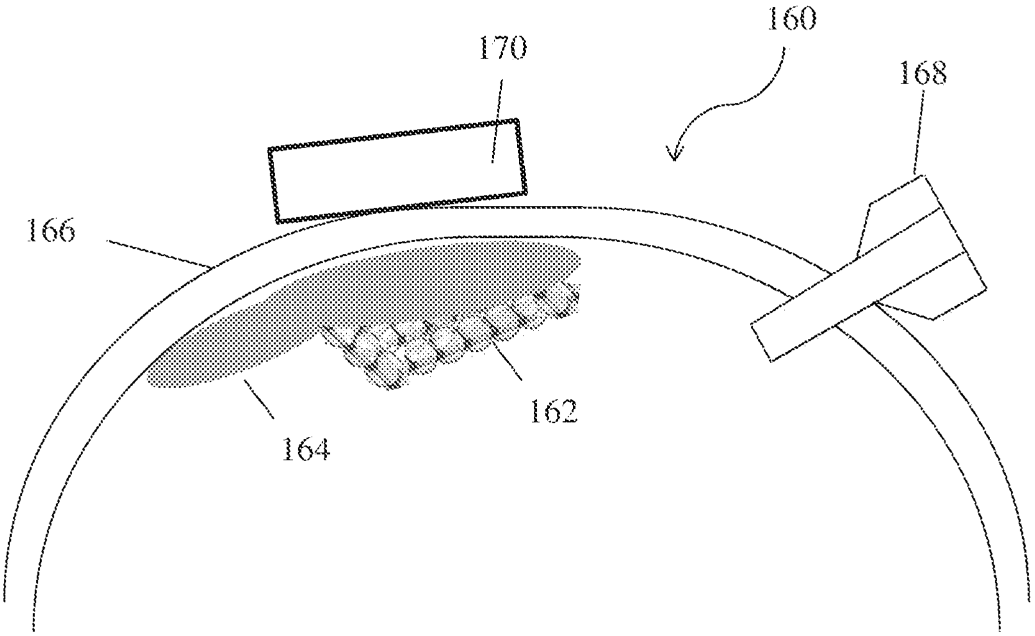

In some variations, the first configuration may be a low-profile configuration in which the retractor may be inserted through a surgical incision and/or a trocar toward a surgical site within the patient. As shown in FIG. 1B, a retractor (162) may be inserted in a low-profile configuration through a patient wall (166) of a patient (160) within a trocar (168) toward tissue (164). In some variations, the retractor (162) may be inserted through the trocar (168) and/or manipulated within a body cavity by a grasper tool (not shown). After the retractor (162) is passed into the patient, the retractor (162) may permit other tools or devices to access the trocar (168), thereby lowering the total number of incisions that are needed for the surgical procedure. In some variations, the second configuration may be an expansive configuration in which the retractor (162) may engage at least a portion of tissue (164) (e.g., an internal organ) of the patient. In some variations, an applied magnetic force may transition the retractor (162) from the low-profile configuration to the expansive configuration. As shown in FIG. 1C, the retractor (162) in the second expansive configuration may engage and/or support at least a portion of tissue (164). In FIG. 1D, a control element (170) may be provided external to the patient wall (166) to apply a magnetic force such that the retractor (162) exerts a force on at least a portion of the tissue (164). For example. FIG. 1D depicts the tissue (164) moved against an internal side of the patient wall (166) with the tissue (164) between the retractor (162) and the patient wall (166). As described in more detail below, the retractor may include rounded and/or smooth edges and features, such that the retractor generally engages the internal organ substantially atraumatically to reduce the likelihood of tissue damage.

In some variations, the retractor may transition or move between a first configuration and a second configuration. For instance, the retractor may be biased from a first low-profile configuration to a second expansive configuration. In variations in which the first configuration is a low-profile configuration and the second configuration is an expansive configuration, the retractor may be held in the first, compact low-profile configuration for insertion into a patient, but may be reconfigured into the second, larger-profile expansive configuration for a surgical procedure.

In some variations, the retractor may be constrained in the first configuration by any suitable element, such as a trocar, an additional external sleeve, a guidewire, or the like. For example, the size and configuration of a trocar may restrict the retractor to the first configuration while it is in the trocar, but allow the retractor in the first configuration to pass through the trocar. Upon exiting the trocar and entering the surgical site of the patient, the constriction of the retractor may be relieved and the bias in the retractor may cause it to move into the second configuration. In other instances, the retractor may transition from a first configuration to a second configuration by the application of a magnetic field, as described in more detail below.

In some variations, one or more magnetic portions of the retractor may respond to a magnetic field (e.g., a magnetic field produced by an external magnet) to support and/or move (e.g., retract, reposition) tissue (e.g., an internal organ) engaged by the retractor. For example, in some variations, the retractor may engage at least a portion of an internal organ or other tissue such that the internal organ is situated proximate an internal side of the patient wall, between the retractor and an external magnet external to the patient (e.g. on an external side of the patient wall). In these variations, the attraction between the external magnet and the one or more magnetic portions of the retractor may result in the displacement of at least a portion of the retractor and the tissue (e.g., an internal organ), so as to retract the tissue to increase access to a surgical site.

In some variations, the retractor body may comprise a metal (e.g., stainless steel), plastic, silicone, and/or another suitable biocompatible material. Such material may be, for example, molded or machined to form one or more components of the retractor body, and may be chosen to have particular magnetic properties, as described in more detail below. Additional manufacturing details in other variations are described below.

In some variations, one or more magnetic portions of the retractor may include a separate mass made of a magnetic material ("a magnetic mass") coupled to the retractor body through at least one of an adhesive (e.g., epoxy), mechanical coupling (e.g., press-fit, settings, threads, pockets), molding, or otherwise embedded within the retractor body, or any suitable means. In other variations, the retractor body may additionally or alternatively comprise a magnetic material. In some variations, a magnetic material as used herein may be a permanent magnet made of materials such as Alnico alloys, ferrite (ceramic), rare earth (e.g., NdFeB (Neodymium-Iron-Boron) or SmCo (Samarium-Cobalt)), or iron-chromium-cobalt. In other variations, magnetic material as used herein may be a mass of ferrimagnetic or ferromagnetic material (e.g., iron, cobalt, nickel) that is attracted by a magnetic field but does not independently generate a magnetic field.

A set of exemplary retractors are described in detail below where the retractor may transition from a generally compact shape into an expansive shape that may generally include a coil, cradle, lever, platform, and/or sling. As depicted in the drawing figures and described below, the retractors described herein are not particularly limited in shape.

Retractor—Coiled

In some variations, a retractor may comprise a linkage for transitioning between a low-profile configuration for insertion into a patient and an expansive configuration having a coil shape to move and/or support tissue. FIGS. 2A-5B are generally directed to retractors that may transition from a first linear configuration to a second coiled configuration. The coiled retractors described here may be inserted into a body cavity through small openings in a first linear configuration and then expanded into a suitable shape and size to manipulate tissue within the body cavity. The configuration of the retractor is such that tissue damage is minimized to improve treatment outcomes.

In some variations, as described above, a first configuration of the retractor may be generally linear. In some of these variations, the retractor may provide a larger supportive surface area in a second configuration relative to the first configuration, such as a configuration approximating a planar surface, saddle shape, or the like. For instance, a retractor in the first configuration may be delivered into a patient through an incision in a patient wall and/or a trocar. For example, the retractor in a linear configuration may be passed over a guidewire through the trocar and released from the guidewire inside the patient. As another example, an elongated grasper tool may carry the retractor having a linear configuration through a trocar and may release the retractor inside the patient. A retractor in the second configuration may support or otherwise engage an internal organ or other tissue. After engagement with the tissue, the retractor in the second configuration may, under the influence of a magnetic field generated by an external magnet, be attracted to the external magnet and thereby retract or otherwise move the engaged tissue. After moving the tissue, the external magnet may additionally or alternatively stabilize and maintain the position of the retractor and engaged tissue (e.g., against an internal wall of the patient).

In some variations, a retractor may comprise a plurality of retractor body elements configured to move relative to each other between a generally linear configuration (low-profile) and an expansive configuration. In the expansive configuration, the retractor body elements may form, for example, a coil, spiral, sinusoidal, snaking, zig-zag, or other curvilinear shape, which may provide sufficient surface area for tissue engagement and retraction.

In some variations, the retractor may comprise a connecting element, joints, or other forms of connection interspersed between or otherwise connecting at least a portion of the retractor body elements. The joints or other forms of connection may be biased towards a predetermined configuration and/or have a limited range of motion or other characteristics, which may cause the retractor to preferentially bend or otherwise transition between a linear configuration and an expansive configuration with sufficient surface area for tissue retraction, while substantially preventing the retractor from entering other configurations (e.g., a spherical configuration or irregular configuration or the like that would not provide sufficient surface area for tissue retraction).

Figure 4A:
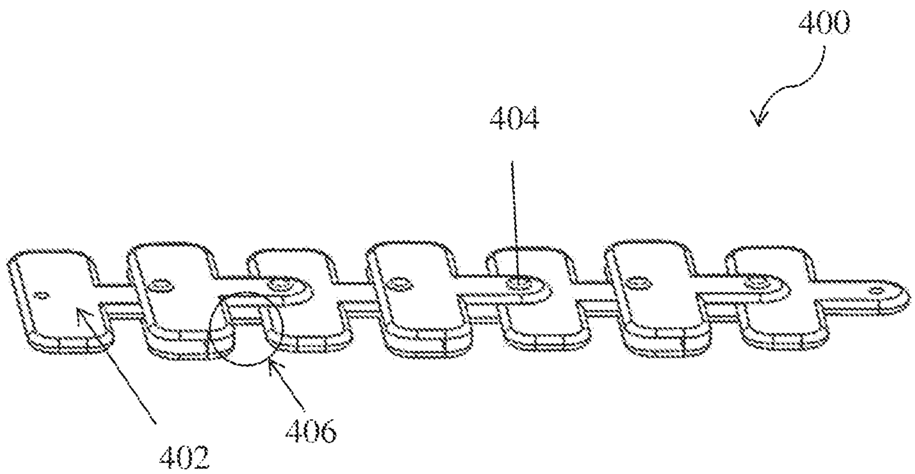
FIGS. 4A and 4B are perspective views of a first low-profile configuration and a second expansive configuration, respectively, of one variation of a retractor.
Figure 4B:
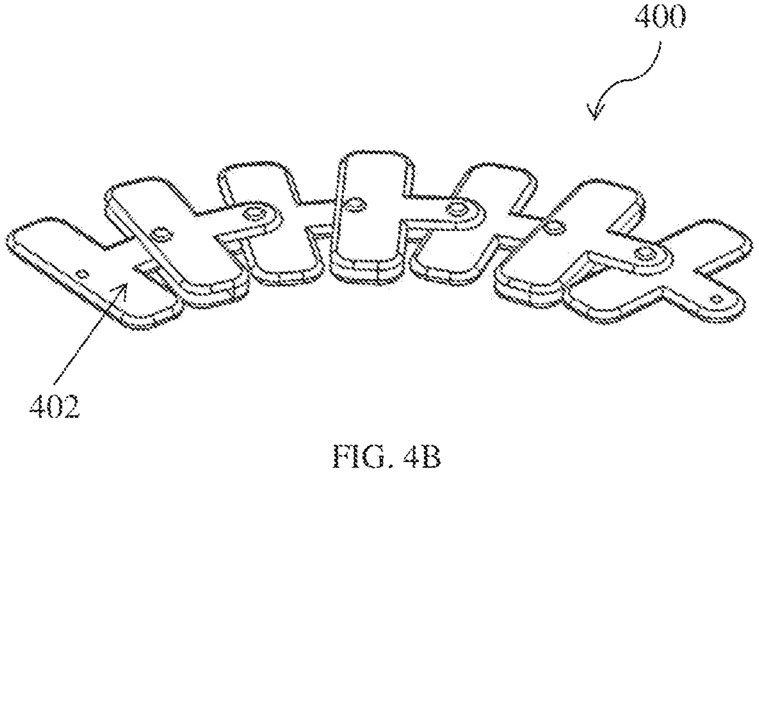

In one variation of a retractor having an expansive coiled configuration as shown in FIGS. 4A-4B, the retractor (400) may comprise a plurality of retractor body elements (402) that may be connected in series with pin joints (404) that substantially limit movement of the retractor body elements (402) within one plane. In some variations, as discussed in further detail below, the retractor may include one or more magnetic masses (of one or more magnetic materials) that may be coupled to at least some of the plurality of retractor body elements, connecting element, and/or other portions of the retractor. In some variations, at least some of the plurality of retractor body elements, connecting element, and/or other portions of the retractor may comprise a magnetic material.

In some variations, one or more of the retractor body elements may comprise rounded and/or smooth edges and features. Additionally or alternatively, at least a portion of the retractor body elements may be coated with a material for biocompatibility and/or for making the retractor atraumatic to blunt or smooth the edges of the retractor and to decrease the application of potentially damaging forces on the internal tissues of the patient. For example, the retractor body elements may be individually dip-coated, sprayed, or otherwise covered with a soft polymer (e.g., silicone) or other soft material that provides a substantially atraumatic cushion around each retractor body element. As another example, a group of retractor body elements (e.g., pairs or groups of three, four, or any suitable number) or the entire retractor may be covered in a soft polymer or other soft material.

Figure 2A:
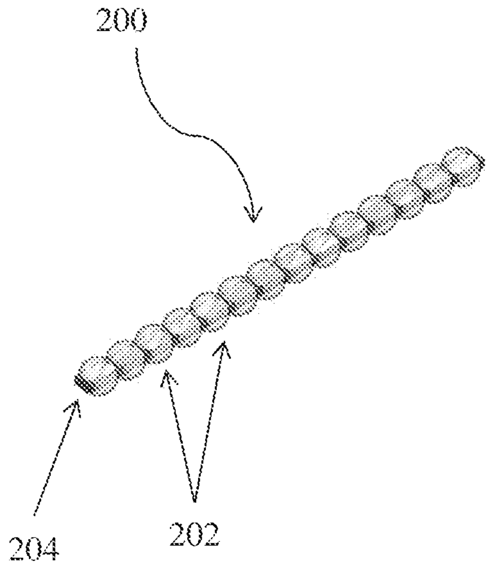
FIGS. 2A and 2B are perspective views of a first low-profile configuration and a second expansive configuration, respectively, of one variation of a retractor.
Figure 2B:
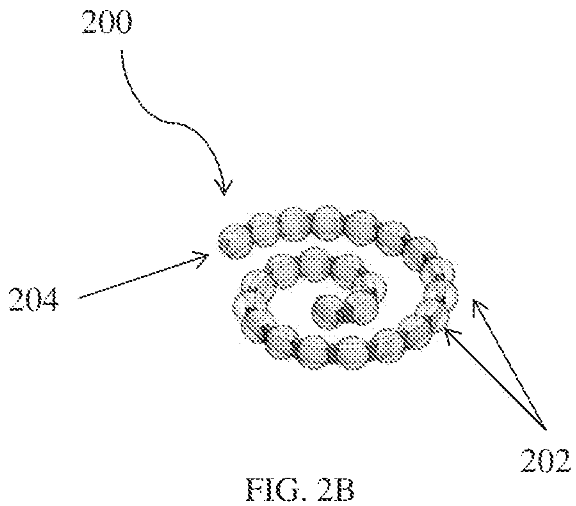

In another variation of a retractor having an expansive coiled configuration as shown in FIGS. 2A-2B, the retractor (200) may comprise a plurality of retractor body elements (202) where the retractor body elements (202) may be connected with one or more connecting elements (204). The retractor body elements (202) may be configured to transition between a generally linear configuration (shown in FIG. 2A) that allows the retractor to be inserted into the patient through a constrained space such as an incision and/or trocar, and an expansive coiled configuration (shown in FIG. 2B) that may provide a larger surface area for engaging and supporting tissue to be moved. At least a portion of the retractor (200) may comprise a magnetic material, such that the retractor (200) may move under the influence of an external magnet (e.g., magnetic control component). As such, when the retractor (200) is supporting tissue (e.g., supporting a portion of an underside of an internal organ), the tissue may be moved.

The retractor body elements (202) may comprise rounded or smooth edges and/or features, such that the retractor (200) may be configured to engage the tissue (e.g., internal organ) substantially atraumatically to reduce the likelihood of tissue damage. For instance, as shown in FIGS. 2A and 2B, the retractor body elements (202) may be generally spherical, but in other variations, the retractor body elements (202) may have any shape, including but not limited to cuboidal, cylindrical, and toroidal shapes. The connecting element (204) may interconnect or link the retractor body elements (202) in series by threading through a lumen of each retractor body element (202). The connecting element (204) may be flexible and elongated to allow the retractor body elements (202) to transition between the low-profile and expansive configurations. For example, the connecting element (204) may include a thread, wire, link, or other suitable elongated element.

In some variations, at least a portion of the connecting element (204) may comprise a magnetic material and/or be coupled to a magnetic mass made of a magnetic material. Additionally or alternatively, at least a portion of the retractor body elements (202) may comprise a magnetic material and/or be coupled to a magnetic mass made of a magnetic material.

The shape and coupling of connecting elements (204) to retractor body elements (202) may determine the shape of the second expansive configuration. In some variations, the connecting element (204) may at least partially influence the geometry of the second configuration of the retractor (200). For example, the connecting element (204) in FIGS. 2A and 2B may comprise a rectangular cross-section, which may favor deformation within a single plane. As another example, the connecting element (204) may have weakened points along its length where bending is more likely to occur, such that the retractor (200) preferentially deforms into a coil-like configuration. Although the connecting element (204) is shown in FIG. 2B as preferentially bending into a coiled configuration, it should be appreciated that in other variations, the connecting element (204) may cause the retractor (200) to preferentially deform into other shapes, such as a zig-zag or sinusoidal shape.

In some variations, the retractor body elements (202) and/or connecting element (204) of a retractor (200) may be initially provided in a first configuration but biased toward its second expansive configuration when unrestrained. In some variations, the connecting elements (204) may comprise a lumen such that, the retractor body elements (202) and connecting elements (204) may be disposed over a guidewire within a trocar. Initially, the retractor (200) may pass through the trocar from outside the body in a substantially linear configuration. As the retractor (200) exits the trocar and into a body cavity of a patient, the retractor (200) may undergo a transition from the first configuration to the second configuration due to a natural bias of the retractor (200) towards the second configuration. For instance, the connecting element (204) may be biased toward a coiled, sinusoidal, zig-zag, or other curvilinear shape to urge the retractor body elements (202) toward the second configuration of the retractor (200) once the retractor (200) is no longer constrained (e.g., the guidewire and/or lumen no longer constrain the retractor (200)). In some variations, the connecting element (204) may comprise a spring or shape memory alloy that transitions the retractor (200) into the second configuration once placed inside the patient.

In some variations, the retractor body elements (202) may be configured to transition between a generally linear configuration and an expansive configuration under application of an external force (e.g., a magnetic field, such as from an external magnet). In one variation, the retractor (200) may have a natural bias towards the generally linear configuration shown in FIG. 2A. However, an external magnet placed outside the body may generate a magnetic field inside the body that acts on one or more of the retractor body elements (202) to cause the retractor (200) to transition into an expansive planar configuration, such as illustrated in FIG. 2B. For example, attractive force of the magnetic field may act on one or more of the retractor body elements (202) to cause motion of each of the retractor body elements (202) toward the external magnet. However, because of the preferential bending of the connecting element (214) connecting the retractor body element (212), the motion may result in the retractor body elements assuming a configuration wherein the retractor body elements are arranged close together in an expansive planar configuration.

Conversely, if the magnetic field is removed and/or altered, the retractor body elements (202) may no longer be attracted toward the planar expansive configuration, and then may relax towards the linear configuration of FIG. 2A. In this manner, a user may control a configuration of the retractor (200) non-invasively from outside the body without direct physical manipulation of the retractor (200).

FIGS. 3A-3B and 4A-4B illustrate other variations of a retractor having a first generally linear configuration and a second expansive configuration, and may function in a similar manner to the retractors described above with respect to FIGS. 2A-2B. Turning to these variations, FIGS. 3A-3B and 4A-4B depict a retractor (300, 400) including a plurality of retractor body elements (302, 402) that may be directly connected to one another in series through joints (304, 404) or other connectors to form a series of retractor body elements (302, 402). Like in the retractor described above in FIGS. 2A-2B, the retractor body elements (302, 402) may be configured to transition between a first generally linear configuration (shown in FIGS. 3A, 4A) that allows the retractor to be inserted into a patient through an incision and/or trocar, and a second expansive coiled configuration (shown in FIGS. 3B, 4B) that provides a larger surface area for supporting tissue to be moved. Similar to the variation depicted in FIGS. 2A and 2B, at least a portion of the retractors (300, 400) may be made of a magnetic material, such that the retractor (300, 400) may move under the influence of an external magnet. As such, when the retractor (300, 400) is supporting tissue (e.g., supporting an underside of an internal organ), the tissue may be moved as well.

Figure 3A:
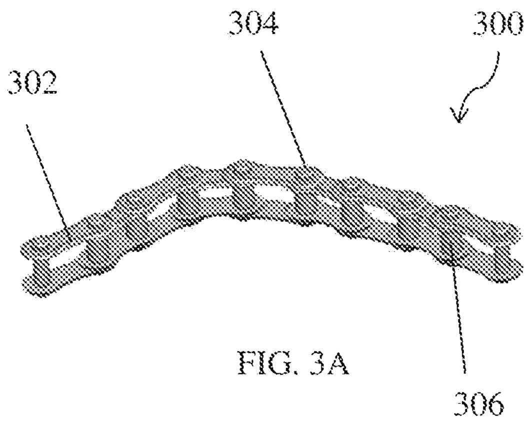
FIGS. 3A and 3B are perspective views of a first low-profile configuration and a second expansive configuration, respectively, of one variation of a retractor.
Figure 3B:
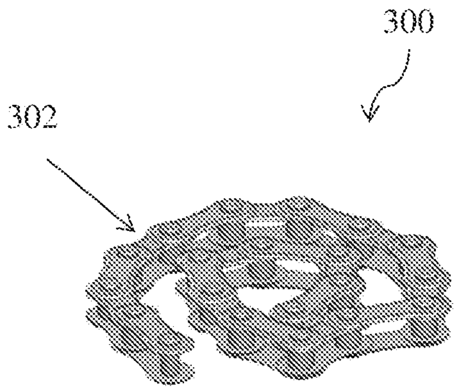

It should be appreciated that the retractor body elements (302, 402) may have any suitable geometry that allows for rotation of retractor body elements (302, 402) about the joints (304, 404) in a plane. For example, as shown in FIGS. 3A and 3B, each retractor body element (302) may be a link comprising two substantially rectangular bars, parallel to and offset from one another with a spacer (306). Each rectangular bar may be connected to at least one other rectangular bar of an adjacent link through a pin joint (304). The retractor body element (302) is not limited to a rectangular bar and may form other geometric shapes.

As another example, as shown in FIGS. 4A and 4B, each retractor body element (402) may be a link generally having a "T" shape. Each link may be connected to at least one adjacent link through a joint (404) in such way that results in spaces (406) being formed between the links for permitting a particular range of motion among the links. The retractor body elements (402) may form other shapes as well that allow a desired range of motion, such as a triangle, ellipse, etc.

In some variations, the shape of retractor body elements (302, 402) and/or nature of joints (304, 404) may at least partially influence the geometry of the second configuration. The joints (304, 404) may, for example, comprise pin joints, each of which may limit relative movement of the retractor body elements to rotation around a single axis, thereby restricting relative movement of the retractor body elements (302, 402) to movement within a single plane. Furthermore, the geometry of the retractor body elements may restrict the extent to which the retractor may coil. For example, as shown in FIG. 4B, physical interference between adjacent retractor body elements (402) may limit how tightly the retractor (40) may be able to coil.

In some variations, the retractor body elements (302, 402) may be configured to transition between a generally linear configuration and an expansive configuration under application of an external force (e.g., a magnetic field from an external magnet). In some variations, the retractors (300, 400) may have a natural bias towards the generally linear configuration shown in FIGS. 3A and 4A. However, an external magnet placed outside the body may generate a magnetic field inside the body that acts on one or more of the retractor body elements (302, 402) to cause the retractor (300, 400) to transition into an expansive planar configuration, such as illustrated in FIGS. 3B and 4B. For example, the attractive force of the magnetic field may act on one or more of the retractor body elements to cause motion of each of the retractor body elements to assume a configuration where the retractor body elements are arranged closer together in an expansive planar configuration. More specifically, each of the retractor body elements (302, 402) may be attracted toward an external magnet, but because of the retractor body elements (302, 402) are limited to rotation in a plane, the attraction toward the external magnet may result in the retractor body elements assuming an expansive planar configuration.

Conversely, if the magnetic field is removed and/or altered, the retractor body elements (302, 402) may no longer be attracted toward the planar expansive configuration, and then may relax towards the linear configuration of FIGS. 3A and 3B. In this manner, a user may control a configuration of the retractor (300, 400) non-invasively from outside the body without physical manipulation of the retractor (300, 400).

While the retractor body elements described above with respect to FIGS. 2A-4B may be interconnected such that their relative range of motion is constrained substantially to a single plane, it should be appreciated that in other variations, the retractor may be configured to have a wider range of motion. In some variations, retractor body elements may have multiple degrees-of-freedom. For example, a connecting element connecting adjacent retractor body elements may be configured to bend in more than one plane (e.g., the connecting element may have a circular cross-section that is equally bendable in multiple directions). In other variations, the retractor body elements may be directly connected via joints allowing for rotation about more than one axis (e.g., a ball-in-socket joint) or allowing the retractor body elements to translate relative to each other.

Figure 5A:
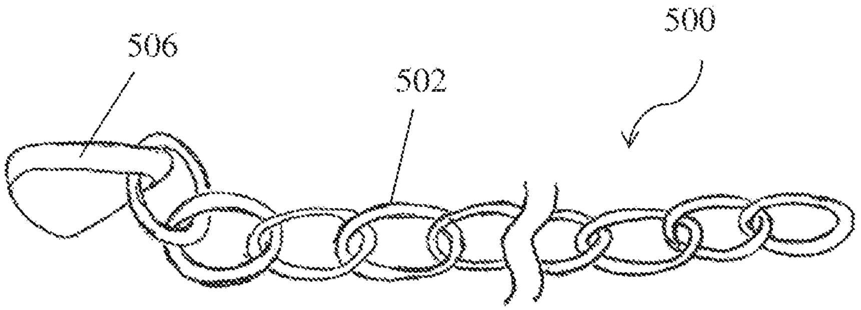
FIGS. 5A and 5B are perspective views of a first low-profile configuration and a second expansive configuration, respectively, of one variation of a retractor.
Figure 5B:
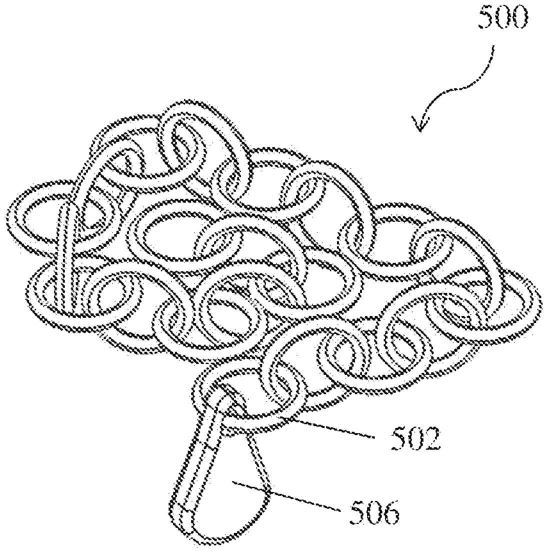

In another variation of a retractor, a second expansive configuration of a retractor (500) may take a generally amorphous form. As shown in FIGS. 5A and 5B, in another variation of the retractors described herein, the retractor (500) comprises a plurality of retractor body elements (502) that may be directly connected to one another by linking to one another to form a serial chain. The retractor body elements (502) may be configured to transition between a first generally linear configuration (shown in FIG. 5A) and a second non-linear configuration (shown in FIG. 5B). For example, the retractor body elements (502) may comprise a ferromagnetic material such that when the retractor (500) is delivered into a body cavity, a user may gather the retractor body elements (502) together into a bunched mass (such as with a grasper tool extending into the body cavity) and apply a magnetic field to the retractor (500) to maintain the retractor body elements (502) as a bunched mass and/or move the bunched mass.

As another example, one or more retractor body elements (502) may comprise a permanent magnet, such that after the retractor (500) is delivered into a body cavity, the retractor body elements (502) may be attracted to each other and self-aggregate into a bunched, amorphous mass. In some variations, the retractor body elements (502) may have any suitable geometry that allows the retractor body elements (502) to rotate and/or translate relative to one another in multiple directions. For example, each retractor body element (502) may comprise a ring, and each ring may be looped with at least one other adjacent ring.

In some variations, a transition between different retractor configurations may be provided without applying a magnetic force to the retractor (500). For instance, the retractor (500) may comprise a transitioning mechanism to transition the retractor (500) from the second configuration shown in FIG. 5B to the first configuration shown in FIG. 5A. This may enable removal of the retractor (500) from an internal surgical site (e.g., after completion of a surgical procedure) or facilitate repositioning of the retractor (500) inside the patient. For example, as shown in FIGS. 5A and 5B, the transitioning mechanism (506) may comprise a tab or pendant coupled to a retractor body element (502). In some variations in which the retractor body elements (502) are made of a ferromagnetic material, when the transitioning mechanism (506) is pulled in the absence of an external magnet, the retractor (500) may be extended so as to transition from the bunched second configuration shown in FIG. 5B to the linear first configuration shown in FIG. 5A.

Additionally or alternatively, an end of the chain of retractor body elements (502) or other segment of the chain may be pulled to extend the retractor (500) and cause the retractor (500) to transition into the linear first configuration or an approximation of the linear first configuration. In some variations, when the transitioning mechanism (506) or other segment of the chain is pulled through a trocar or other restraining sleeve, the physical constriction of the trocar or sleeve may cause a coiled or bunched retractor to straighten out into the linear first configuration. Once transitioned to the linear first configuration, the retractor (500) may be removed from the patient through an incision and/or trocar. In some variations, the transitioning mechanism and/or other part of the retractor may be manipulated with a secondary tool such as a grasper or a laparoscopic tool passing through the trocar or another incision.

Retractor—Cradle

In some variations, a retractor may have a first configuration in which the retractor is low-profile and a second configuration in which the retractor forms a cradle-like, generally concave shape for receiving and supporting at least a portion of tissue (e.g., an internal organ). For example, as described in further detail below, a retractor in its first configuration may be substantially flat and planar, rolled into a cylinder, or folded. The retractor in the first configuration may be inserted into the patient through an incision and/or a trocar. The retractor in a second expansive configuration may allow the retractor to cradle an expansive surface area of the tissue (e.g., an internal organ). In the second configuration, the retractor may define a first cradle portion that contacts or otherwise engages a first portion of the tissue, and a second cradle portion that contacts or otherwise engages a second portion of the tissue and may comprise a magnetic material. In particular, the retractor may define a first cradle side that contacts or otherwise engages a first side of the tissue, and a second cradle side that includes a magnetic material.

Figure 6A:
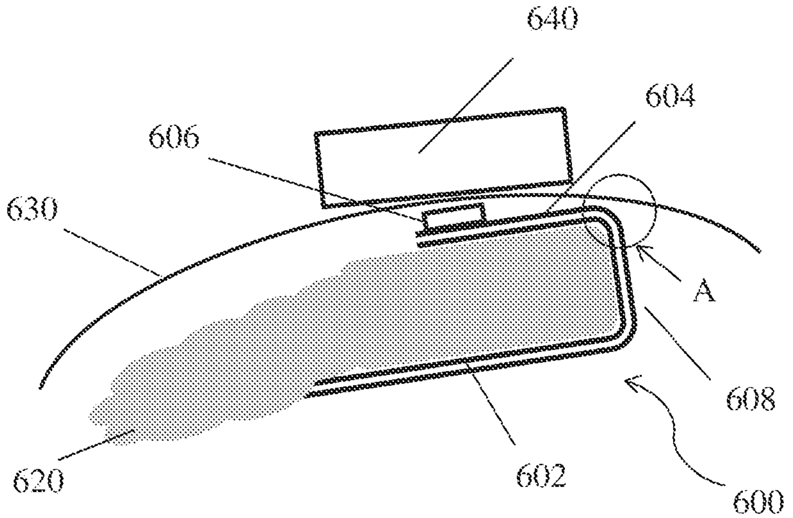
FIG. 6A is a schematic representation of one variation of a retractor system as further depicted in FIGS. 6B-6D.
Figure 6B:
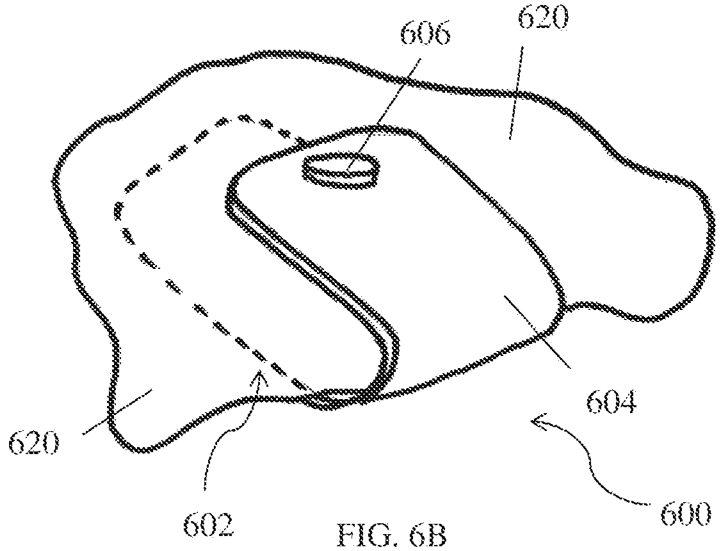
FIG. 6B is a perspective view of the retractor engaging tissue.
Figure 6C:
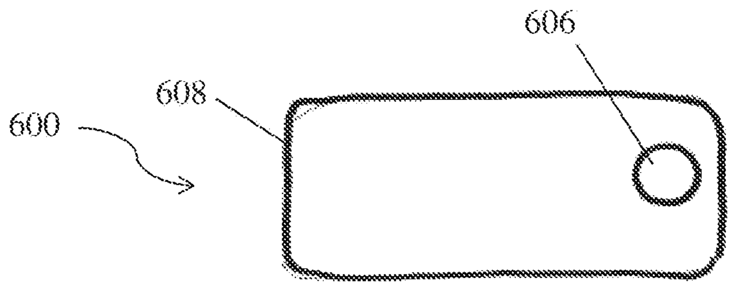
FIG. 6C is a top view of a first low-profile configuration of the retractor.
Figure 6D:
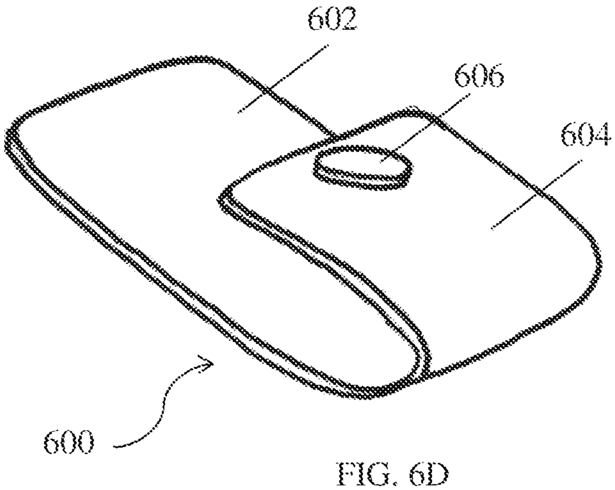
FIG. 6D is a perspective view of a second expansive configuration of the retractor.
Figure 6E:
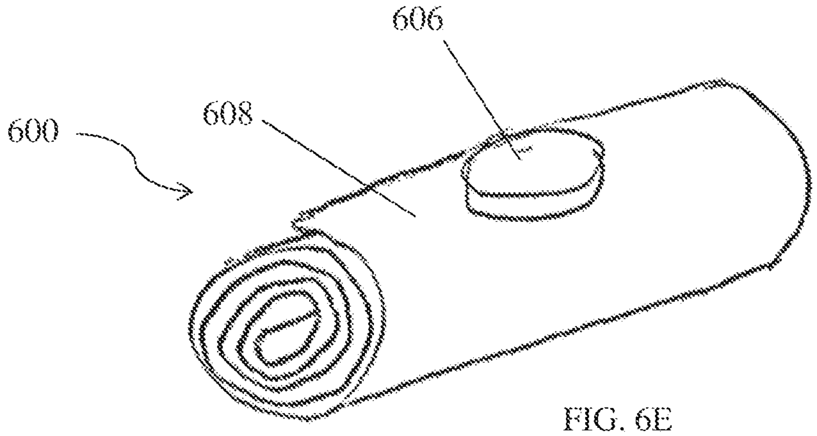
FIG. 6E is a perspective view of a low-profile configuration of one variation of a retractor.

As shown in FIGS. 6A-6E, a retractor (600) for moving and/or supporting tissue (e.g., an internal organ) may comprise a flexible retractor body (608) comprising a first side (602) and a second side (604) that may transition between a substantially planar first configuration (shown in FIG. 6C) and a cradling second configuration (shown in FIGS. 6B and 6D), and a magnetic portion (606) disposed on the retractor body (608). The retractor (600) may further comprise a rolled cylinder configuration (shown in FIG. 6E), which may facilitate insertion into a patient. As shown in FIGS. 6A, 6B, and 6D, the cradling configuration may have a substantially "U"-shaped cross-section, but in other variations the cradling configuration may have any suitable curved shape for receiving tissue, such as a saddle shape, "C" shape. "J" shape, and so forth. In the second configuration, as shown in FIG. 6D, the retractor body (608) may define a first cradle side (602) and a second cradle side (604). The dimensions of the first and second cradle portions may be approximately equal to each other or may differ in dimensions of length, height, width, and thickness. For example, as depicted in FIG. 6D, the second cradle side (604) may be shorter than the first cradle side (602). As shown in FIG. 6B, the first cradle side (602) may engage a first side of an internal organ (620) such that the retractor (600) supports the internal organ (620) in a cradling manner. The second cradle side (604) may be opposite the first cradle side (602).

At least one magnetic portion (606) may be disposed on the retractor body (608) such that when the retractor (600) is in a cradling configuration, the magnetic portion (606) may be positioned on either the first cradle side (602) or the second cradle side (604). As shown in FIGS. 6A and 6B, at least one magnetic portion (606) may be disposed on the second cradle side (604) such that the magnetic portion (606) may be closer to the wall (630) of the patient. Although the figures depict the magnetic portion (606) as a mass of magnetic material provided on an outer surface of the retractor body (608), the magnetic portion (606) may be provided on the inner surface of the retractor body (608), and/or the retractor body (608) may comprise a magnetic material.

FIG. 6A is a cross-sectional side view of a retractor (600) in a second configuration cradling an organ (620). For example, the first cradle side (602) may contact a portion of an underside of the organ (620), while the second cradle side (604) with magnetic portion (606) may be disposed closer to the patient wall (630) and an external magnet (640) outside the patient. Once the retractor (600) has engaged the internal organ (620) as shown, the magnetic portion (606) of the retractor (600) may be drawn toward the external magnet (640) and thereby support, retract or otherwise move the internal organ (620).

As illustrated in FIG. 6A, the magnetic portion (606) of the retractor (600) may be positioned between the external magnet (640) and the organ (620), which may help to maintain the position of the at least partially held organ (620). In particular, the magnetic portion (606) may be positioned closer to the patient wall (630) and external magnet (640) to receive the attractive magnetic force to help maintain the position of the retracted organ (620). In this configuration, the magnetic portion (606) may be a force-bearing element of the retractor (600) that "pulls" the weight of the organ (620) up toward the patient wall (630). This configuration may be more stable than an alternate configuration in which the magnetic portion (606) is positioned under the organ such that the retractor (600) "pushes" the organ (620) toward the patient wall (630).

In some variations, the geometry of the retractor body (608) in the cradling expansive configuration may be configured such that the retractor body (608) maintains a suitable cradling orientation while moving the internal organ (620). For example, with reference to FIG. 6A, the dimensions of cradle sides (602) and (604) may be configured such that at least a portion of the retractor body (608) at a contact area (A) contacts the interior wall (630) of the patient. The contact area (A) may help prevent the retractor (600) from over-rotating in a counter-clockwise direction (as drawn in FIG. 6A) to a degree that would cause complete disengagement of the retractor body (608) from internal organ (620) (e.g., an orientation in which internal organ (620) would slip out of the cradle). In particular, the length of the first cradle side (602), the second cradle side (604), and location of the magnetic portion (606) may be such to help prevent the retractor (600) from entirely disengaging from internal organ (620) (e.g., in view of the size and weight of the internal organ (620)). In some instances, the retractor (600) may engage a portion of tissue (620) (e.g., half of the organ (620) is engaged by the cradle (600)).

In some variations, the retractor body (608) may bias the retractor (600) toward its cradling configuration. For example, the bias may be formed with one or more shape memory wires, fibers, mechanical mechanisms, and/or other substances embedded to or coupled to the retractor body (608). In variations in which the retractor body (608) has an unrolled, substantially planar first configuration (FIG. 6C), the retractor body (608) may be biased to at least partially curl into a cradling configuration (FIGS. 6B and 6D). In variations in which the retractor body (608) has a rolled, cylindrical first configuration (FIG. 6E), the retractor body (608) may be biased to at least partially unroll.

Figure 7A:
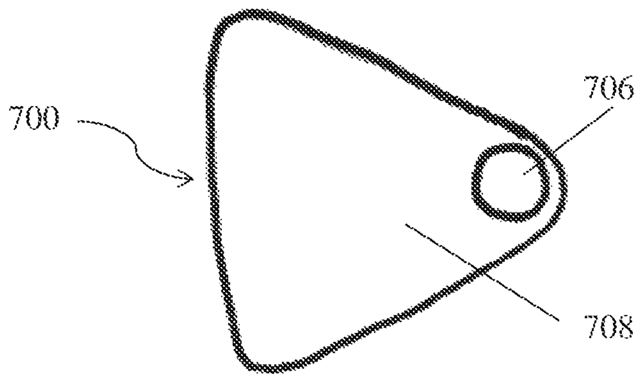
FIGS. 7A and 7B are perspective views of a first low-profile configuration and a second expansive configuration, respectively, of one variation of a retractor.
Figure 7B:
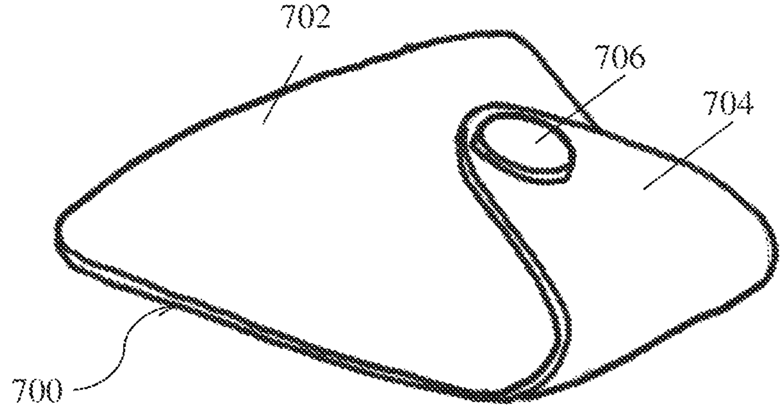
Figure 8A:
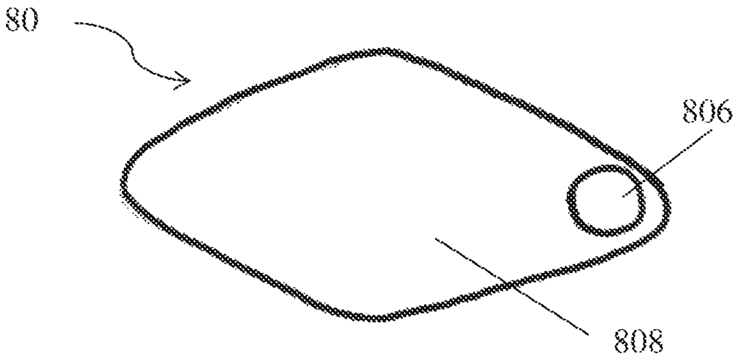
FIGS. 8A and 8B are perspective views of a first low-profile configuration and a second expansive configuration, respectively, of one variation of a retractor.
Figure 8B:
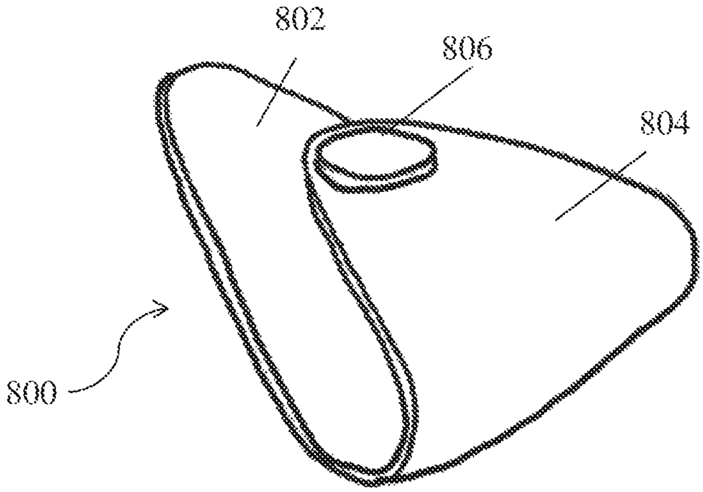

In some variations, the retractor body (608) may comprise a flexible sheet. In other variations, the retractor may comprise a flexible scaffold and a supportive membrane coupled to the scaffold and configured to support an internal organ or other tissue in a manner similar to that described above. Although FIGS. 6A-6E depict a retractor body (608) having a generally rectangular shape when unrolled or flattened (FIG. 6C), it should be appreciated that the retractor body (608) may have other shapes. For example, as shown in FIGS. 7A and 7B, respectively, the retractor (700) may comprise a magnetic portion (706) and a retractor body (708). The retractor body (708) may have a generally triangular shape when unrolled (FIG. 7A), and may form a cradle with a wider first cradle portion (702) and a narrower second cradle portion (704) (FIG. 7B). As another example, as shown in FIGS. 8A and 8B, respectively, the retractor (800) may comprise a magnetic portion (806) and a retractor body (808). The retractor body (808) may have a generally diamond shape when unrolled (FIG. 8A), and may form a cradle with a generally triangular first cradle portion (802) and a generally triangular second cradle portion (804) (FIG. 8B). In other variations, the retractor body may have an unrolled shape that is generally circular, elliptical, a polygon of any number of sides, symmetric, asymmetric, irregular, or any suitable shape.

Figure 9A:
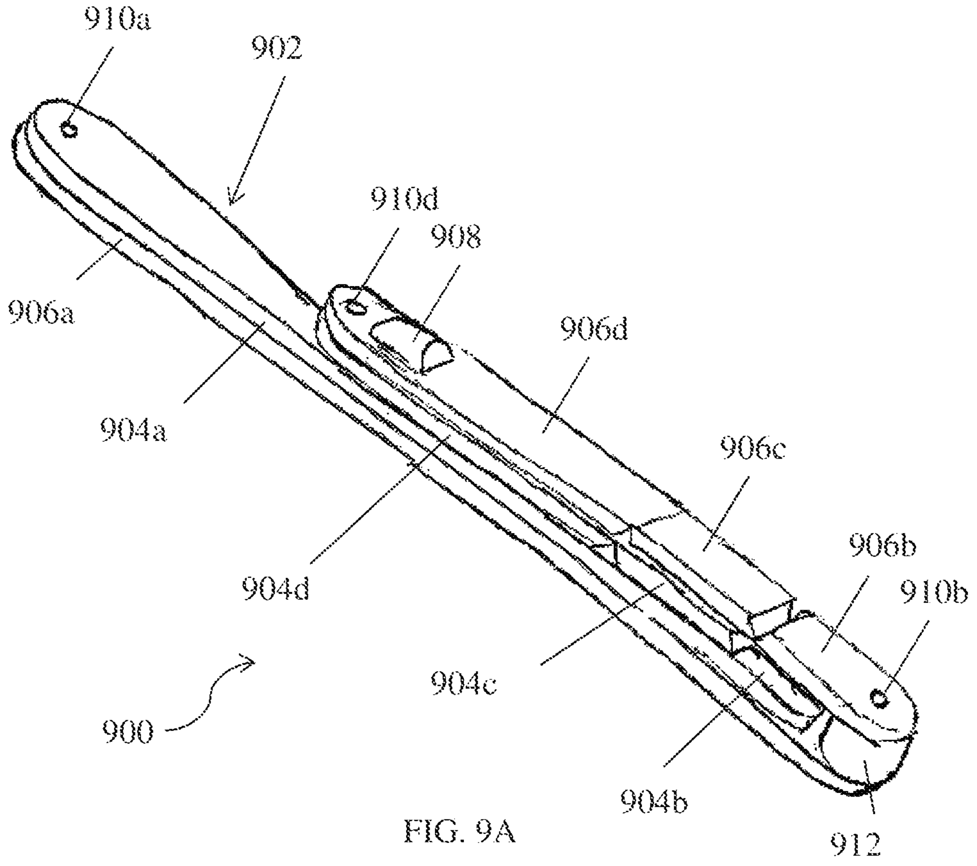
FIGS. 9A and 9B are perspective views of a first low-profile configuration and a second expansive configuration, respectively, of one variation of a retractor.
Figure 9B:
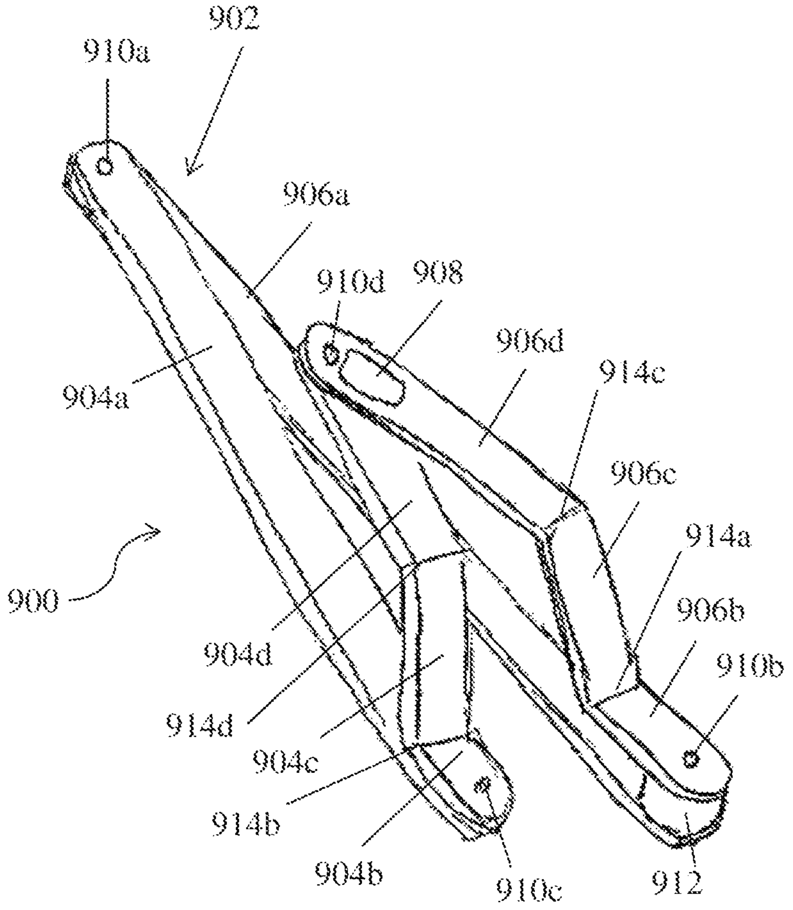

In some variations, a retractor may comprise a retractor body comprising a rotatable linkage for transitioning between a first low-profile configuration and a second expansive configuration by rotation of one or more joints and/or hinges. As shown in FIGS. 9A and 9B, in one variation of the retractors described herein, the retractor (900) may transition between a collapsed, low-profile configuration (shown in FIG. 9A) and an expansive cradle configuration (shown in FIG. 98). The retractor (900) may further comprise a magnetic portion (908). The linkage (902) shown may be covered by a membrane (not shown). In the low-profile configuration, the linkage (902) may be substantially collapsed and allow the retractor (900) to be delivered into a patient through an incision and/or trocar. In the expansive configuration, the linkage (902) may be expanded to form a cradle that may support at least a portion of tissue (e.g., an internal organ). Like the variations described above with reference, to FIGS. 6A-8B, the retractor (900) in the cradling configuration may define a first cradle portion and a second cradle portion. The first cradle portion may engage a first side of an internal organ (not shown), and the second cradle portion may engage a second side of the internal organ. The second cradle portion may further comprise the magnetic portion (908). Although magnetic portion (908) is depicted in FIGS. 9A and 9B as having a magnetic mass coupled to the linkage (902), the linkage (902) may additionally or alternatively be at least partially made of a magnetic material.

As shown in FIG. 9A, the retractor (900) may include a linkage (902) with a plurality of linkage members (904*a*-904*d* and 906*a*-906*d*). At least some of the linkage members (904*a*-904*d* and 906*a*-906*d*) may nest together and overlap with each other when the retractor (900) is in the low-profile configuration. For example, at least some of the linkage members, such as linkage members (906*a*) and (906*b*), may be offset by a spacer (912) that provides a space between linkage members (906*a*) and (906*b*). When the retractor (900) is in the low-profile configuration, linkage members (904*a*). (904*b*), (904*c*), and (904*d*) (the "left side" members, as shown in the perspective of FIG. 98) may nest with linkage members (906*a*), (906*b*), (906*c*), and (906*d*) (the "right side" members, as shown in the perspective of FIG. 9B) such that the left-side members are substantially parallel with the right-side members and the retractor (900) is in the low-profile, folded configuration of FIG. 9A for insertion through an incision and/or trocar into the patient.

In some variations, at least some of the linkage members may pivot relative to each other within a first range of motion. For example, as shown in FIG. 9B, pin joint (910*a*) may couple linkage members (904*b*) and (906*a*), pin joint (910*a*) may couple linkage members (906*a*) and (906*b*), pin joint (910*b*) may couple linkage members (904*a*) and (904*b*), and pin joint (910*d*) may couple members (904*d*) and (906*d*) so as to enable the linkage (902) to collapse and expand in a first plane (e.g., to bring members (906*a*) and (904*a*) closer together or farther away from one another).

In some variations, at least some of the linkage members may pivot relative to each other within a second range of motion. For example, as shown in FIG. 9B, hinge joint (914*a*) may couple linkage members (906*b*) and (906*c*), hinge joint (914*b*) may couple linkage members (904*b*) and (904*c*), hinge joint (914*c*) may couple linkage members (906*c*) and (906*d*), and hinge joint (914*d*) may couple linkage members (904*c*) and (904*d*), such that the retractor (900) may collapse and expand generally in a second plane different than the first plane (e.g., to bring members (904*d*) and (906*d*) closer to and farther from linkage members (906*a*) and (906*b*)).

In some variations, at least some of the joints may have a biasing element that biases the retractor body toward the second expansive cradle configuration. For example, hinge joint (914*d*) and/or hinge joint (914*c*) may comprise a spring (e.g., torsion spring) or a shape memory material to urge the retractor body toward the second configuration. In other variations, as shown in FIGS. 10A and 10B, some or all of the hinge joints may be a living hinge (1000) having chamfers that provide built-in stops for limiting the extent to which the linkage members may pivot. The hinge (1000) may permit adjacent linkage members to lie flat (FIG. 10A) and swing relative to one another up to a particular maximum bent angle (FIG. 10B). In some variations, as shown in FIG. 10C, some or all of the hinge joints may include a hinge (1002) and a stopper (1004) or other mechanism for limiting the direction and/or extent of pivoting linkage members.

Although FIGS. 9A and 9B depict a retractor body comprising a linkage with eight members, in other variations, the linkage may include a different number of members with fewer or more members (e.g., three, four, five, six, seven, nine, ten, etc.).

Retractor—Lever

In some variations, a retractor may comprise a pivotable linkage configured to act as a lever. In a low-profile configuration, the retractor may be inserted through an incision and/or a trocar, and in an expansive configuration, the retractor may form a lever for receiving and pivotably supporting at least a portion of tissue (e.g., an internal organ). As described in further detail below, the retractor may include at least one magnetic portion such that in response to an applied magnetic force (e.g., an external magnet located outside the body), at least a portion of the retractor in its lever configuration may tilt to lift the internal organ.

In some variations, as described for example below with reference to FIGS. 11A-11B, an external magnet (1140) may cause the retractor (1100) to tilt to lift at least a portion of an internal organ (1120) by simultaneously magnetically repelling one portion (1108) of the retractor (1100) and magnetically attracting another portion (1110) of the retractor (1100). For instance, as shown in FIG. 11B, an external magnet (1140) may cause the retractor to tilt the retractor body (1104) against a contact area (B) located on the internal wall (1130) of the patient to provide a pivot point for the retractor (1100). The retractor (1100) may tilt to lift at least a portion of the tissue as one portion of the retractor (1100) is magnetically attracted by the external magnet (1140) and the retractor (1100) pivots about a pivot point against a body cavity wall (1130) to manipulate the tissue. In some variations, the magnetic portion (1108, 1110) may comprise a magnetic mass that is made of a magnetic material and coupled to the retractor (1100). In some variations, the at least a portion of the retractor body (1104) may comprise a magnetic material.

Figure 11A:
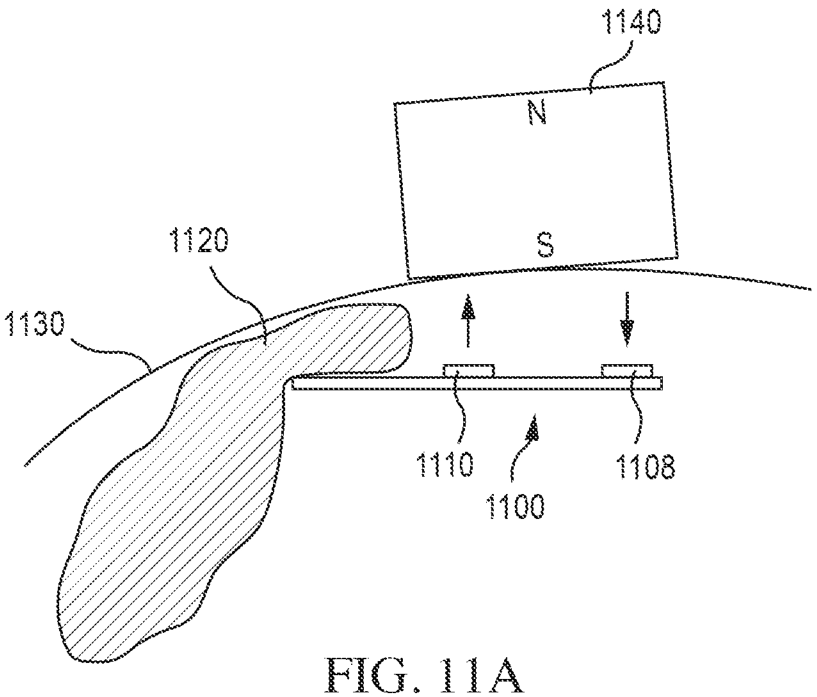
FIGS. 11A-11B are schematic representations of one variation of a retractor system.
Figure 11B:
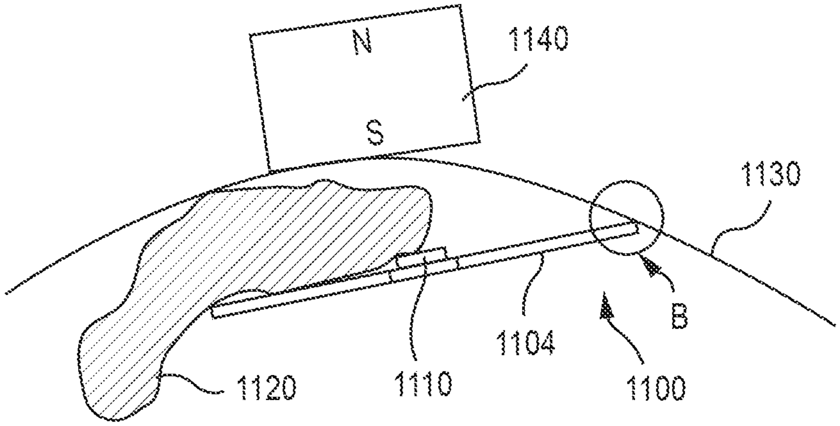
Figure 11C:
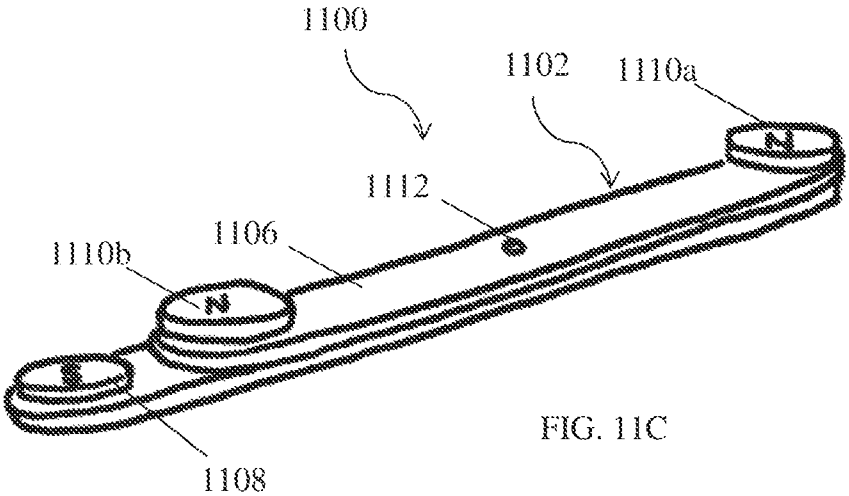
FIGS. 11C and 11D are perspective views of a first low-profile configuration and a second expansive configuration, respectively, of the retractor depicted in FIGS. 11A-11B.
Figure 11D:
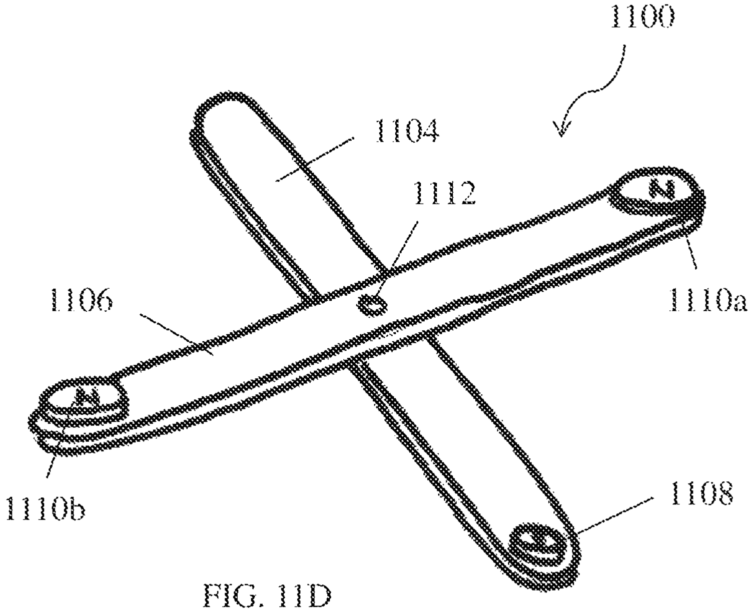

As shown in FIGS. 11C and 11D, the retractor (1100) may comprise a retractor body that includes a linkage (1102) that may transition between a low-profile configuration (shown in FIGS. 11C) and an expansive configuration (shown in FIG. 11D). The retractor (1100) may further comprise a plurality of magnetic portions (1108), (1110*a*), and (1110*b*) coupled to the linkage (1102). In particular, as shown in FIG. 11D, the linkage (1102) may include a first linkage member (1104) and a second linkage member (1106). First linkage member (1104) and second linkage member (1106) may be coupled by a pin joint (1112) and may enable the linkage (1102) to transition between a low-profile collapsed configuration and an expansive, cross-shaped linkage configuration. Magnetic portion (1108) may be disposed on a first end of the first linkage member (1104) and have a first polarity. Magnetic portions (1110*a*) and (110*b*) may be disposed on opposing ends of the second member (1106), respectively, and have a second polarity opposite from the first polarity. For example, magnetic portion (1108) may be configured to have a south pole facing in a first direction, while magnetic portions (1110*a*) and (1110*b*) may be configured to have a north pole facing in a first direction, or vice versa.

Figure 11E:
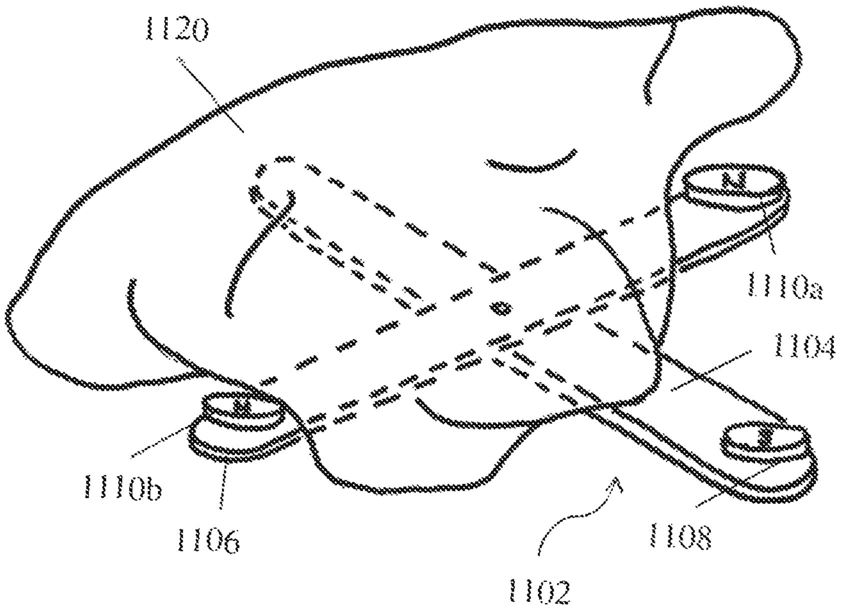
FIG. 11E is a perspective view of the retractor shown in FIG. 11D engaging tissue.

As shown in FIG. 11E, in its lever configuration, the linkage (1102) may engage tissue (1120) (e.g., an internal organ) by supporting an underside of the tissue (1120) with at least a portion of linkage members (1104) and/or (1106). In particular, an end of linkage member (1104) opposite the magnetic portion (1108) may be positioned under the tissue (1120), while the end of linkage member (1104) with magnetic portion (1108) may be unengaged with the tissue (1120). In some variations, the ends of linkage member (1106) and magnetic portions (1110*a*, 1110*b*) may, but need not, support the tissue (1120).

As shown in FIG. 11A, an external magnet (1140) may be positioned proximate the retractor (1100) such that magnetic portion (1108) is repelled from the patient wall (1130) while magnetic portion (1110) is attracted toward the wall (1130). The retractor (1100) in the lever configuration as shown in FIG. 11D may tilt around a pivot axis (1112) located on linkage members (1104, 1106) in response to an applied magnetic force generated by external magnet (1140), thereby pivoting and lifting the internal organ (1120). As such, the external magnet (1140) may have a polarity configured to repel magnetic portion (1108) and configured to attract magnetic portion (1110). In some variations, at least some of the magnetic portions (1108, 1110), may include a ferromagnetic material that does not have a particular polarity, but may still be attracted to external magnet (1140) such that the retractor (1100) tilts to lift the internal organ (1120). It should be appreciated that although the figures show magnetic portions (1108, 1110) as magnetic masses coupled to a linkage member, in other variations, the linkage members may comprise a magnetic material, such as those magnetic materials described above.

In some variations, the retractor (1100) may be additionally or alternatively configured to brace against the internal wall (1130) of the patient when tilting to lift the tissue (1120). For example, as shown in FIG. 11B, linkage member (1104) may contact the patient wall (1130) at contact area (B). External magnet (1140) may attract the magnetic portion (1110), and/or other magnetic portions of the retractor (1100), to pivot the retractor (1100) around contact area (B). In these variations, pivoting of linkage member (1104) about contact area (B) may provide the traction to enable the retractor (1100) to tilt to lift the tissue (1120). Although FIG. 11B shows magnetic portion (1110) as magnetic masses coupled to the linkage members, in other variations, the linkage members (1104, 1106) may comprise a magnetic material, such as those magnetic materials described above.

Similar to the variations described above, the retractor (1100) may be biased toward its low-profile configuration or its expansive configuration, such as with a spring or shape memory materials. In some variations, the retractor may be biased toward its low-profile configuration for ease of insertion and removal from a body cavity. In these variations, the retractor may be held in the expansive configuration by, for example, a pin (not shown) in linkage member (1106) that may engage with a corresponding detent or hole (not shown) in linkage member (1104). The retractor (1100) may move from an expansive configuration to a low-profile configuration when the pin is removed.

In some variations, the retractor may include a transitioning mechanism that assists in transitioning the retractor from the expansive configuration to the collapsed configuration, such as to prepare the retractor for removal from the patient or to make it easier for the retractor to be repositioned in the patient. For example, a transitioning mechanism may include a suture or string extending between first linkage member (1104) and second linkage member (1106), such that grasping, hooking, or otherwise laterally pulling the transitioning mechanism (not shown) with a grasper tool may cause the linkage members (1104) and (1106) to close and transition toward the collapsed, low-profile configuration. Such a transitioning mechanism may be similar, for example, to that depicted in FIGS. 17A and 17B and described in further detail below. Such a transitioning mechanism may be useful, for example, in variations in which the retractor is biased toward an expansive configuration.

In other variations, the retractor (1100) may include fewer or more magnetic portions, such as one, two, three, four, five, six, or more magnetic portions. The location of each of the plurality of magnetic portions may affect how different portions of the retractor are attracted to and/or repelled by a magnetic field, and therefore the degree of tilt generated for lifting and supporting the issue (e.g., internal organ). Similarly, although FIGS. 11A-11E depict a retractor linkage with two linkage members, in other variations, the linkage may include fewer or more members, such as one, two, three, four, five, six, or more linkage members.

In some variations, a retractor may comprise a linkage comprising a flexible member. Attraction of the flexible member to one or more external magnets may improve the maneuverability of the retractor, and thus the maneuverability of the tissue held by the retractor. For example, FIC. 12A depicts one variation of a retractor (1200) having one linkage member (1202), a flexible member (1208) coupled to the linkage member (1202) at a pivot point (1206), and a plurality of magnetic portions (1204), (1210*a*), and (1210*b*).

Figure 12A:
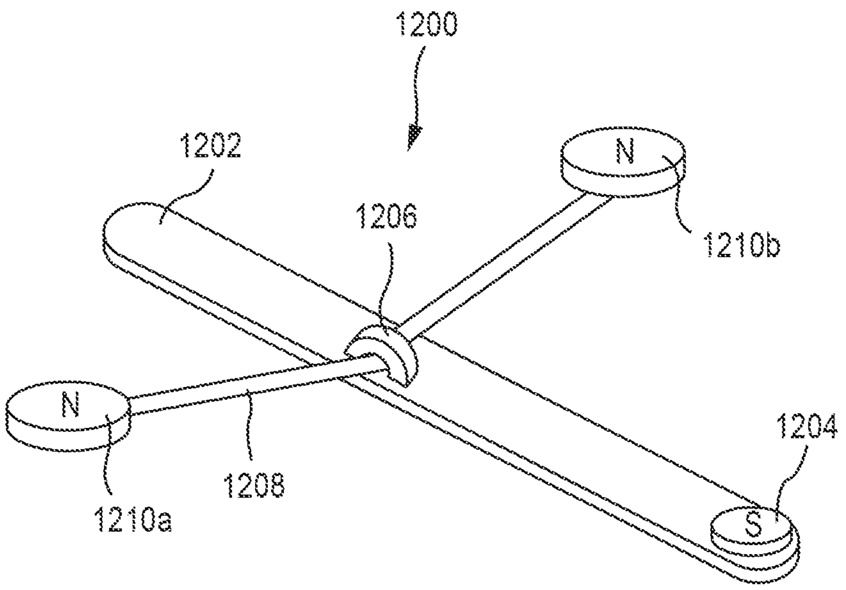
FIG. 12A is a perspective view of one variation of a retractor in an expansive configuration.
Figure 12B:
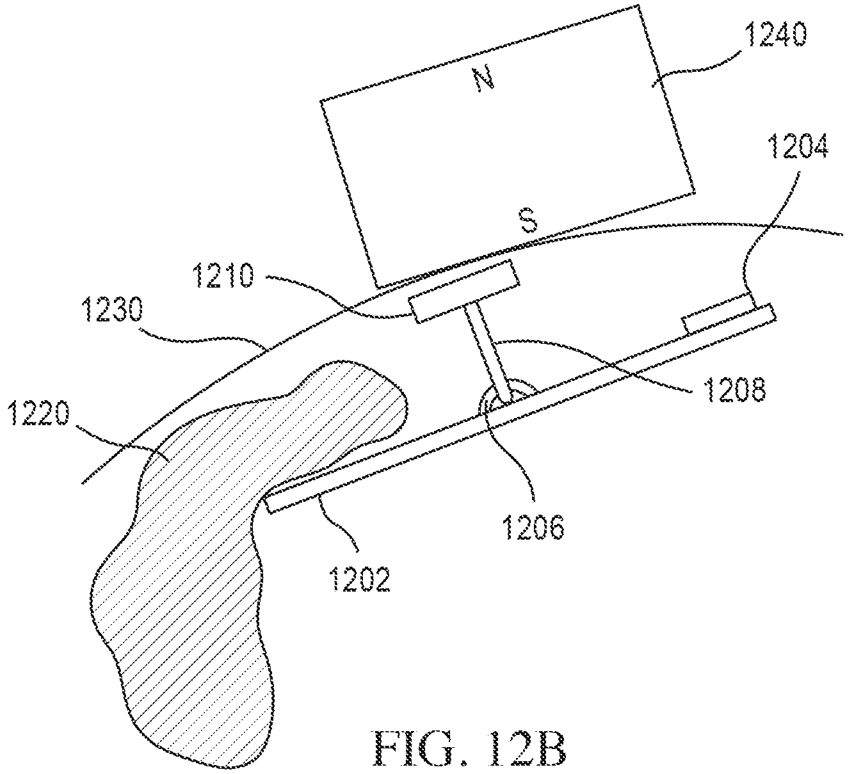
FIG. 12B is an illustrated depiction of one variation of a retractor engaging tissue.

The flexible member (1208) may be a non-rigid or semi-rigid elongated member that connects magnetic portions (1210*a*) and (1210*b*), such as a suture. In some variations, the combination of multiple external magnets may move the magnetic portions (1204). (1210*a*), and (1210*b*), thereby controlling the location of the pivot point (1206) and/or strength of the moment force applied to the retractor (1200). For instance, as shown in FIG. 12B, a set of external magnets (1240) (only one shown in FIG. 12B) may be placed above each of the magnetic portions (1210*a*, 1210*b*), and the two external magnets (1240) may be used to move magnetic portions (1210*a*) and (1210*b*) farther apart to raise the pivot point (1206) relative to the patient wall (1230) or closer together to lower the pivot point (1206). Additionally, a third external magnet (not shown) may be placed above magnetic portion (1204) to increase or decrease the moment applied to the retractor (1200). In this manner, multiple external magnets may individually control movement of different magnetic portions of the linkage, thereby enabling modulation of the pivot point location, degree of tilt, strength of moment applied to the retractor, and other characteristics.

Figure 12C:
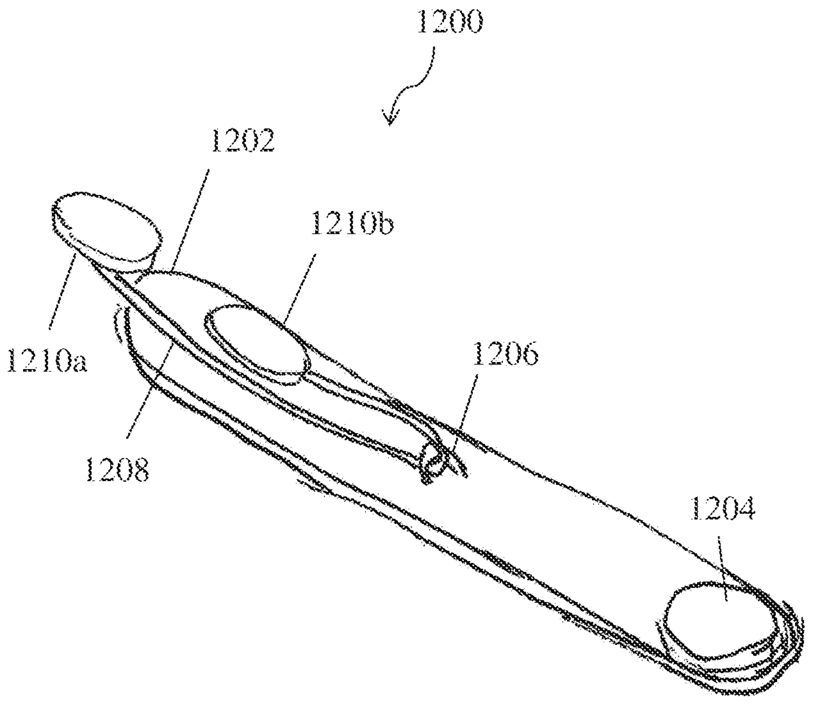
FIG. 12C is a perspective view of one variation of a retractor in a low-profile configuration.

In some variations, the flexible member (1208) may collapse to a low-profile configuration, as shown in FIG. 12C. In the low-profile configuration, the flexible member (1208) may be positioned along the linkage member (1202). Magnetic portions (1204), 01210*a*), and (1210*b*) may operate substantially similarly to magnetic portions (1108). (1110*a*), and (1110*b*), respectively, described above with reference to FIGS. 11A-11E. Flexible member (1208) may provide a pivot axis around which linkage member (1204) may tilt to support and/or move at least a portion of tissue (1220). For example, one or more magnetic portions (1204), (1210*a*), and (1210*b*) may be attracted to respective external magnets (1240) so as to attract the magnetic portions (1204), (1210*a*), and (1210*b*) towards the patient wall (1230). Movement of one or more of the external magnets (1240) may attract the corresponding magnetic portions (1204), (1210*a*), and (1210*b*) to provide a desired tilt of the retractor (1200).

Figure 13:
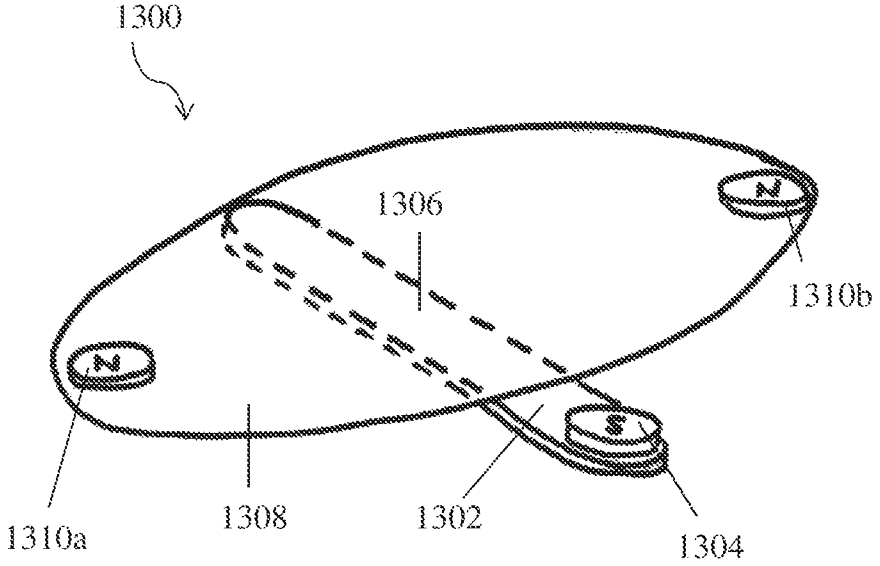
FIG. 13 is a perspective view of one variation of a retractor in an expansive configuration.

In some variations, a retractor may comprise a retractor body comprising a linkage coupled to a membrane. FIG. 13 depicts another variation of a retractor (1300) having a retractor body comprising one linkage member (1302), a membrane (1308) coupled to the linkage member (1302) at a pivot point (1306) and/or one or more other suitable locations along the linkage member (1302) (e.g., coupled along the length of linkage member (1302)). The linkage member (1302) may further comprise a magnetic portion (1304). The membrane (1308) may further comprise a plurality of magnetic portions (1310*a*) and (1310*b*). Magnetic portions (1310*a*) and (1310*b*) may be coupled to the membrane (1308) such that they may be manipulated to expand membrane (1308) and/or act as anchoring points for the membrane (1308). The membrane (1308) may be flexible, stretchable, and/or define folding features (e.g., pleats) such that the retractor (1300) may transition between a low-profile configuration, and an expansive configuration having additional surface area to support the tissue. When expanded, the membrane (1308) may operate substantially similarly to the linkage members described above with reference to FIGS. 11A-11E, but may provide additional atraumatic support to the tissue.

In some variations, the membrane (1308) may include a flexible material such as silicone, while in other variations the membrane (1308) may include a woven material such as polyester and/or a plastic film such as polycarbonate. The membrane (1308) may be coupled to the linkage member (1302) with a suture, epoxy, or in any suitable manner. Magnetic portions (1304), (1310*a*), and (1310*b*) may operate substantially similarly to the magnetic portions described above with reference to FIGS. 11A-11E. Although FIG. 13 depicts the magnetic portions (1304), (1310*a*), and (1310*b*) as magnetic masses coupled to the linkage member (1302) and/or membrane (1308), in other variations the linkage member (1302), membrane (1308), and/or other portions of the retractor (1300) may comprise a magnetic material.

Figure 14:
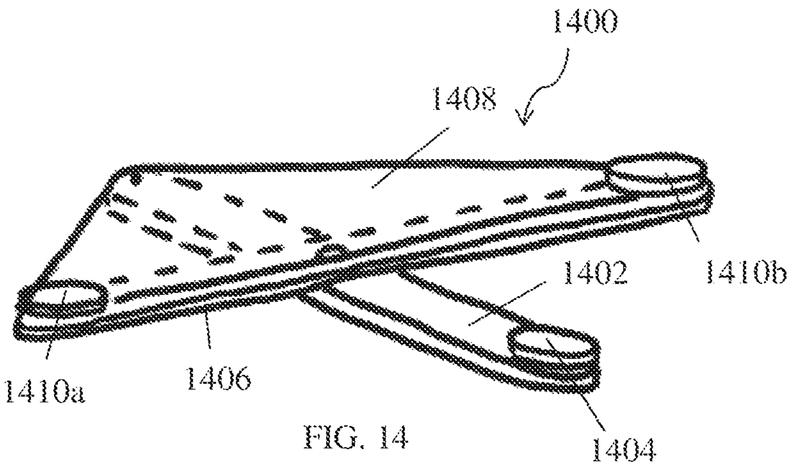
FIG. 14 is a perspective view of one variation of a retractor in an expansive configuration.

In some variations, a retractor may comprise a retractor body having a plurality of linkage members coupled to a membrane. As shown in FIG. 14, the retractor (1400) may comprise a linkage (1402, 1406) substantially similar to that described above with reference to FIGS. 11A-11E. A first linkage member (1402) may comprise a first magnetic portion (1404) and a second linkage member (1406) may comprise a second magnetic portion (1410*a*) and a third magnetic portion (1410*b*). The retractor (1400) may further comprise a membrane (1408) coupled to the one or more of the first and second linkage members (1402) and (1406) and/or magnetic portions (1410*a*, 1410*b*). When expanded, at least a portion of the retractor (1400) may tilt in a manner substantially similar to linkage (1102) described above, and the membrane (1408) may provide additional atraumatic support to the tissue during support and/or movement of the tissue.

In some variations, the membrane (1408) may be elastic or otherwise expandable such that the membrane (1408) may transition from a constricted or folded state to an expansive state corresponding to the low-profile and expansive configuration of the retractor (1400), respectively, while still being coupled to the linkage (1402). In some variations, the membrane (1408) may additionally or alternatively include a scaffold (e.g., a rigid or semi-rigid border) that helps the membrane (1408) maintain its expanded configuration when the retractor (1400) is expanded. In some variations, the membrane (1400) may be similar to that described below. Although FIG. 14 depicts the magnetic portions (1404, 14010*a*, 14010*b*) as magnetic masses coupled to the retractor (1400), in other variations the retractor (1400) may comprise a magnetic material.

Figure 15:
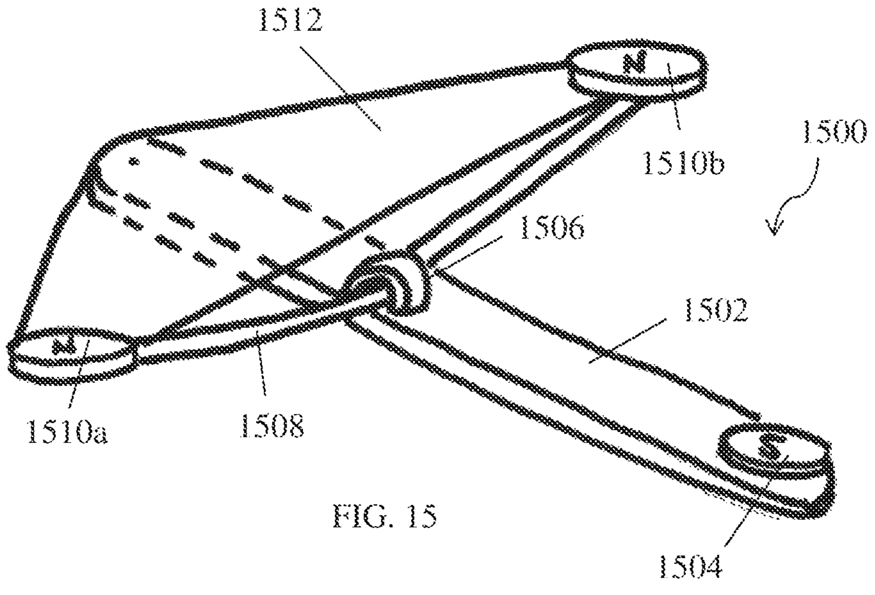
FIG. 15 is a perspective view of one variation of a retractor in an expansive configuration.

In some variations, a retractor may comprise a semi-flexible linkage coupled to a membrane. As shown in FIG. 15, the retractor (1500) may comprise a linkage (1502, 1508) substantially similar to that described above with reference to FIG. 12A. A first linkage member (1502) may comprise a first magnetic portion (1504) and a second linkage member (1508) may comprise a second magnetic portion (1510*a*) and a third magnetic portion (1510*b*). The retractor (1500) may further comprise a membrane (1512) coupled to at least one of first linkage member (1502), second linkage member (1508), and/or one of the magnetic portions (1510*a*, 1510*b*). When expanded, at least a portion of the retractor (1500) may tilt in a manner substantially similar to the retractor (1200) of FIG. 12A, and the membrane (1512) may provide additional atraumatic support to the tissue during support and/or movement of the tissue. In some variations, the membrane (1512) may be similar to that described below.

Retractor—Platform

In some variations, a retractor may comprise a linkage and membrane configured to form a platform for supporting tissue. For example, the retractor in an expansive configuration may form a platform to support the underside or other suitable surface of tissue. In the low-profile configuration, the retractor may be inserted through an incision and/or a trocar into the patient. In the expansive configuration, the surface area of the retractor may increase to support tissue.

In some variations, the retractor may include a linkage and a membrane coupled thereto, where the membrane may expand in surface area to provide additional support for tissue. In some variations, the retractor may include at least one magnetic portion such that in response to a magnetic field (e.g., a magnetic field generated by an external magnet), at least a portion of the retractor supports, retracts or otherwise moves the tissue supported by the membrane. In some variations, the magnetic portion may comprise a magnetic mass comprising a magnetic material. In some variations, the retractor may comprise a magnetic portion at least partially comprising a magnetic material.

In some variations, the membrane may be flexible, stretchable, and/or define folding features (e.g., pleats) such that the membrane may collapse and expand in correspondence with the low-profile and expansive configurations of the retractor. When expanded, the membrane may provide additional surface area for supporting an internal organ. In some variations, the membrane may include a flexible material such as silicone, while in other variations the membrane may include a woven material such as polyester fabric. The membrane may be coupled to the linkage member with a suture, epoxy, or in any suitable manner.

In some variations, a retractor may be biased toward an expansive configuration. In these variations, the retractor may be held in a low-profile configuration for insertion, repositioning, or removal by, for example, a trocar during insertion into a patient, a grasper device, a sleeve, or the like. In some variations, it may be possible to adjust the retractor from an expansive configuration to a low-profile configuration by pulling the retractor back through an incision and/or trocar. As the retractor is pulled through a trocar, the rigidity of the trocar cannula may exert pressure on the anchor elements to cause them to rotate towards each other and toward the low-profile configuration. Once in the collapsed, low-profile configuration, the retractor may be able to be removed from the patient. Additionally or alternative, a retractor may comprise a transition mechanism to transition the retractor from the expansive configuration to the low-profile configuration, such as a suture or string attached to two or more linkage members.

Figure 16A:
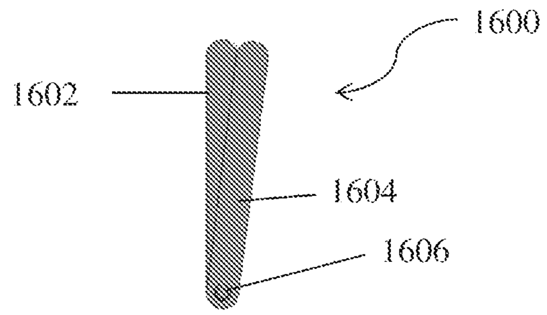
FIGS. 16A and 16B are side views of a first low-profile configuration and a second expansive configuration, respectively, of one variation of a retractor.
Figure 16B:
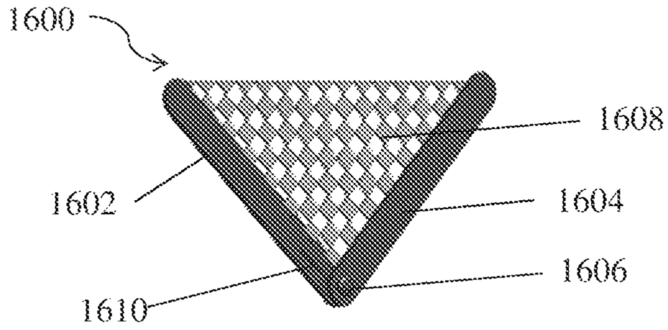
Figure 16C:
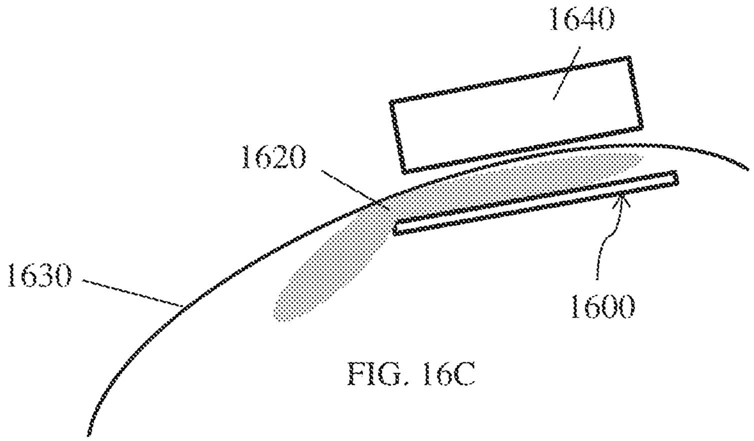
FIG. 16C is a schematic representation of one variation of a retractor system.

In one variation, as shown in FIGS. 16A and 16B, a retractor (1600) may transition between a low-profile, collapsed configuration (shown in FIG. 16A) and an expansive fan configuration (shown in FIG. 16B). The retractor (1600) may comprise a membrane (1608) coupled to a first linkage member (1602) and a second linkage member (1604). At least a portion of the linkage members (1602, 1604) and/or membrane (1608) may comprise a magnetic material (e.g., a magnetic mass may be coupled to the linkage members (1602, 1604) and/or membrane (1608), or the linkage members (1602, 1604) and/or membrane (1608) may comprise a magnetic material). The first linkage member (1602) and second linkage member (1604) may be coupled by a joint (1606). The linkage (1602, 1604) may enable the retractor (1600) to transition between a low-profile, substantially linear configuration configured to pass through an incision and/or trocar, and an expansive fan configuration that may expand the membrane (1608) to support tissue. FIG. 16C illustrates an external magnet control (1640) provided outside a patient wall (1630) where the magnet control (1640) may manipulate one or more magnetic portions of the retractor (1600) as the retractor (1600) supports the underside or other suitable surface of tissue (1620), so as to support and move (e.g., elevate or retract) the supported tissue (1620). As shown in FIG. 16C, the retractor (16000) may support a portion of the tissue (1620), but in other variations, the retractor (1600) may support the entire tissue (1620) (e.g., internal organ).

In some variations, the retractor (1600) may include a biasing element (1610) that biases a retractor body comprising a linkage toward its expansive fan configuration. For example, biasing element (1610) may comprise a torsion spring coupled to joint (1606) that urges apart first linkage member (1602) and second linkage member (1604). As another example, the biasing element (1610) may comprise a compression spring coupled to the first linkage member (1602) and second linkage member (1604) at a location distal to the joint (1606), so as to urge apart the first linkage member (1602) and the second linkage member (1604).

Although FIGS. 16A-16C depict a retractor (1600) having two linkage members and one membrane, it should be appreciated that in other variations, the retractor may include fewer or more linkage members, and/or multiple membranes. For example, a retractor may include one, two, three, four, five, six, or more linkage members. Additionally or alternatively, a retractor may include two, three, four, five, or more membranes. The one or more linkage members and/or one or more membranes may be combined in any suitable manner to form a platform for supporting tissue. In some variations, multiple membranes may be layered on one another (e.g., to form a bi-layered or tri-layered membrane), such as to increase a collective supportive strength of the retractor or to decrease the permeability of the membranes. In other variations, multiple membranes may additionally or alternatively be arranged adjacent to one another, such as to increase the overall surface area or customize the supportive surface area for a particular organ or kind of tissue.

Figure 17A:
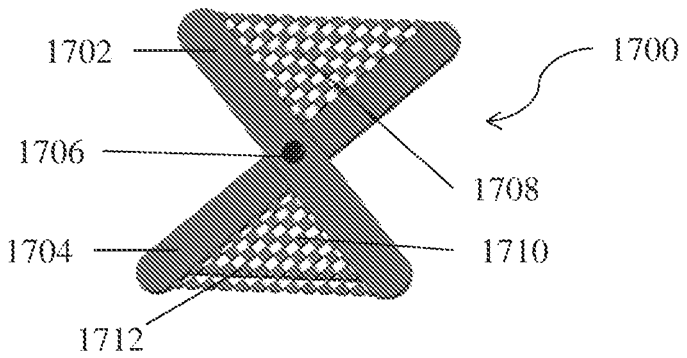
FIGS. 17A and 17B are first side and second side views of one variation of a retractor in an expansive configuration.
Figure 17B:
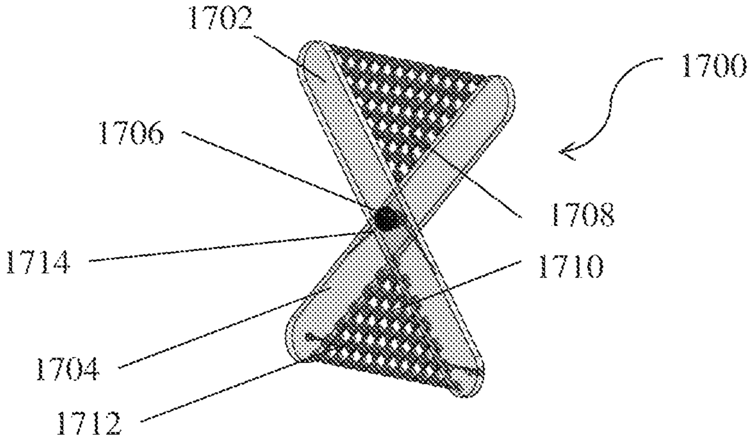

In some variations, a retractor may comprise an "X"-shaped linkage coupled to a membrane. For example, as shown in FIGS. 17A-17B, a retractor (1700) may comprise linkage members (1702, 1704) coupled to at least one membrane (1708, 1710). At least a portion of the linkage (1702, 1704) and/or membrane (1708, 1710) may include a magnetic material (e.g., a magnetic mass may be coupled to the retractor and/or membrane, or the retractor and/or membrane may comprise a magnetic material). The linkage may include a first linkage member (1702) and a second linkage member (1704) coupled to a joint (1706), such as a pin joint, that enables the retractor (1700) to transition between a low-profile, substantially linear configuration that allows the retractor (1700) to pass through an incision and/or trocar, and an expansive "X"-shaped configuration that may expand one or more membranes (1708, 1710) for supporting tissue.

In some variations, the linkages (1702, 1704) may be arranged to provide an expansive "T"-shaped configuration, or arranged at any suitable angle relative to each other. The retractor (1700) may include a first membrane (1708) and a second membrane (1710) coupled to the first linkage member (1702) and/or second linkage member (1704) to form a platform in the expansive configuration. For example, as shown in FIGS. 17A and 17B, the first membrane (1708) and second membrane (1710) may be arranged opposite one another. In some variations, the retractor (1700) may include a biasing element (1714) to bias the retractor (1700) toward its expansive "X"-shaped configuration, similar to biasing element (1610) described above.

In some variations, the retractor (1710) may include at least one transitioning mechanism (1712) to transition the retractor (1700) from the expansive "X"-shaped configuration to the low-profile configuration. For example, as shown in FIGS. 17A and 17B, the transitioning mechanism (1712)

may comprise a suture or string coupled on a first end to a first linkage member (1702) and coupled on a second end to a second linkage member (1704). The transitioning mechanism (1712) may be grasped, hooked, or otherwise laterally pulled (e.g., with a device extending through an incision or trocar), thereby generating a force that urges first linkage member (1702) and second linkage member (1704) to rotate toward each other to the low-profile configuration. As another example, the membrane (1708, 1710) may be forced to close (e.g., by pulling the membrane laterally out of the plane of the retractor) with a grasper or other device, thereby pulling the linkage members (1702, 1704), which may be attached to the membrane (1708, 1710), toward each other to a low-profile configuration.

Figure 18:
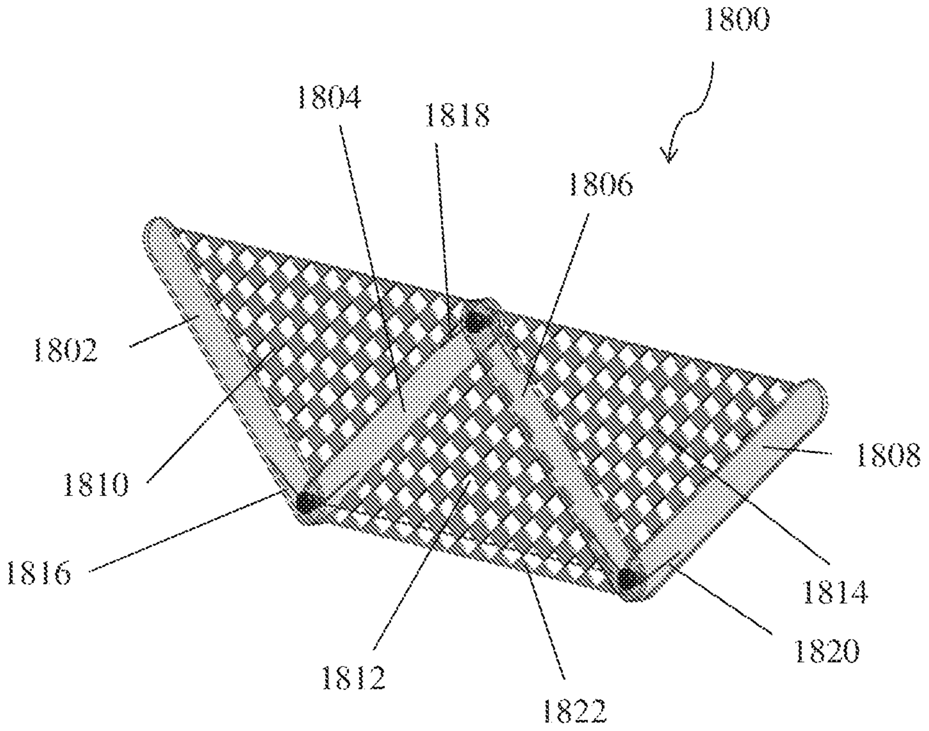
FIG. 18 is a perspective view of one variation of a retractor in an expansive configuration.

In some variations, a retractor may comprise a "W"-shaped linkage coupled to at least one membrane. As shown in FIG. 18, the retractor (1800) may comprise a retractor body comprising a linkage that may transition between a low-profile configuration and an expansive "zig-zag"-shaped or "W"-shaped configuration. The retractor (1800) may further comprise at least one membrane (1808, 1810, 1812) coupled to the linkage (1802, 1804, 1806, 1808). At least a portion of the linkage (1802, 1804, 1806, 1808) and/or membrane (1810, 1812, 1814) may comprise a magnetic material (e.g., a magnetic mass may be coupled to the linkage and/or membrane, or the linkage and/or membrane may comprise a magnetic material). The linkage may include a first linkage member (1802), a second linkage member (1804), a third linkage member (1806), and a fourth linkage member (1808) connected with one or more joints (not labeled), such as a pin joint. The linkage may enable the retractor (1800) to transition between a low-profile, substantially linear configuration that allows the retractor (1800) to pass through an incision and/or trocar, and an expansive "W"-shaped configuration that expands the one or more membranes for supporting tissue (e.g., an internal organ).

In other variations, the number of linkage members may be more or less than shown in FIG. 18 with a similar end-to-end arrangement in series to form any suitable zig-zag shape. The retractor (1800) may comprise a first membrane (1810), a second membrane (1812), and a third membrane (1814) each coupled to at least one of the linkage members to form a platform when the retractor (1800) is expanded. For example, as shown in FIG. 18, the membranes (1810, 1812, 1814) may collectively form a trapezoidal shape spanning the "W"-shape of the linkage members (1802, 1804, 1806, 1808) when the retractor (1800) is expanded. In some variations, the retractor (1800) may include one or more biasing elements (1816), (1818), and/or (1820) to bias the retractor (1800) toward its "W"-shaped configuration, similar to the biasing elements described above. In some variations, the retractor (1800) may include one or more transitioning mechanisms (1822) to transition the retractor (1800) from the expansive "W"-shaped configuration to the low-profile configuration, similar to the transitioning mechanisms described above. For example, the transitioning mechanism (1822) may comprise a suture or sting coupled to non-adjacent ends of linkage members. The transitioning mechanism (1822) may be grasped, hooked, or otherwise laterally pulled (e.g., with a device extending through an incision or trocar), thereby generating a fore that urges linkage members to rotate toward each other to the low-profile configuration. As another example, the membrane (1812) may be forced to close (e.g., by pulling the membrane (1822) laterally out of the plane of the retractor (1800)) with a grasper or other device, thereby pulling the linkage members (1804, 1803), which may be attached to the membrane (1812), toward each other to a low-profile configuration. In some variations, the retractor (1800) may be biased towards the expansive configuration and comprise the transitioning mechanism (1822).

Figure 19:
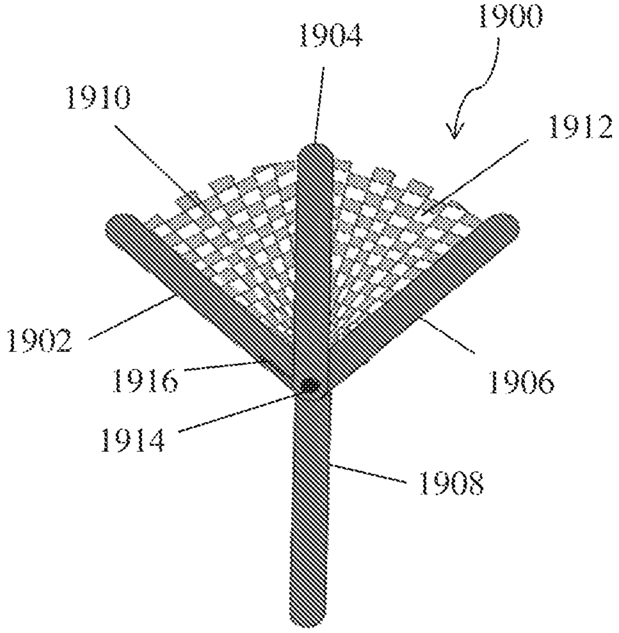
FIG. 19 is a front view of one variation of a retractor in an expansive configuration.

In some variations, a retractor may comprise a fan-shaped linkage coupled to at least one membrane. As shown in FIG. 19, the retractor (1900) may comprise a linkage to transition between a low-profile configuration and an expansive fan configuration. At least a portion of the linkage and/or membrane may comprise a magnetic material (e.g., a magnetic mass may be coupled to the linkage and/or membrane, or the retractor (1900) and/or membrane may comprise a magnetic material). The retractor (1900) may comprise a retractor body comprising a linkage comprising a first linkage member (1902), a second linkage member (1904), a third linkage member (1906), and fourth linkage member (1908), at least some of which are connected at a shared joint (1914), such as a pin joint. The linkage may enable the retractor (1900) to transition between a low-profile substantially linear configuration that allows the retractor to pass through an incision and/or trocar, and an expansive fan configuration that expands the one or more membranes for supporting tissue (e.g., an internal organ).

In other variations, the linkage may include a different number of linkage members than depicted in FIG. 19, where at least a portion of them are similarly arranged in parallel (e.g., at least three linkage members share a common joint) so as to form a platform when the retractor (1900) is expanded. The retractor (1900) may comprise a first membrane (1910) and a second membrane (1912), each spanning the space between two adjacent linkage members. As shown in FIG. 19, the space between some adjacent linkage members may lack a membrane (e.g., the space between first linkage member (1902) and fourth linkage member (1908).

In some variations, the retractor (1900) may include one or more biasing elements (1916) such as a torsion spring and/or compression spring to bias the retractor (1900) toward its expansive fan configuration, similar to the biasing elements described above. In some variations, the retractor (1900) may comprise one or more transitioning mechanisms to transition the retractor from the expansive fan configuration to the low-profile configuration, similar to the transitioning mechanisms described above.

Figure 20A:
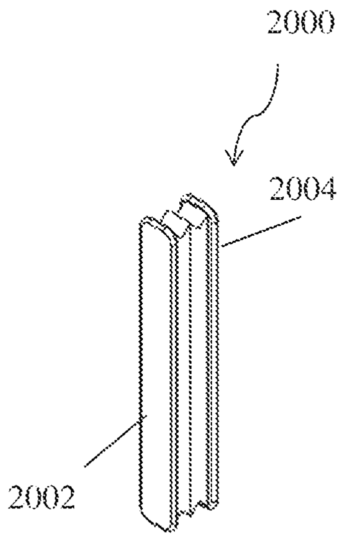
FIG. 20A is a perspective view of one variation of a retractor in a low-profile configuration.
Figure 20B:
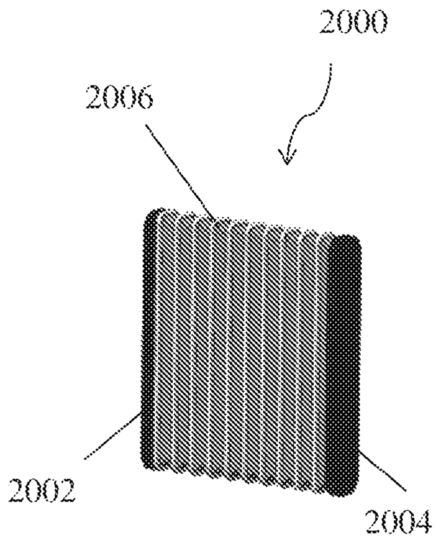
FIGS. 20B and 20C are different perspective views of the retractor of FIG. 20A in an expansive configuration.
Figure 20C:
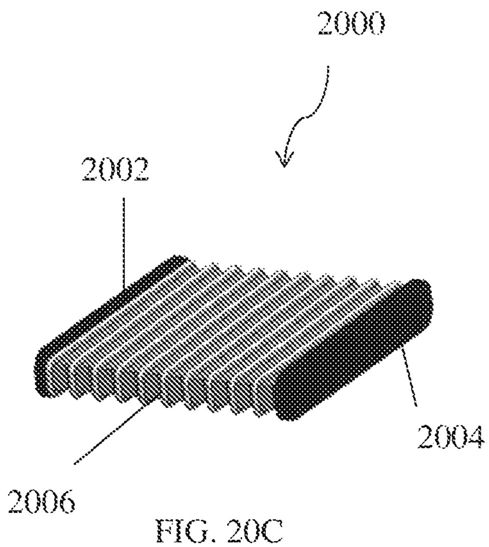

In some variations, a retractor may comprise an accordion-shaped membrane coupled between retractor body members. As shown in FIGS. 20A-20C, a retractor (2000) may comprises a retractor body comprising at least two retractor body members (2002) and (2004) configured to transition between a low-profile collapsed configuration (shown in FIG. 20A) and an expansive platform configuration (shown in FIGS. 20B and 20C). In some variations, the retractor body members (2002, 2004) may be substantially linear. At least one membrane (2006) may be coupled at opposing ends to the retractor body members (2002, 2004). At least a portion of the retractor body and/or membrane (2006) may comprise a magnetic material (e.g., a magnetic mass may be coupled to the retractor body members (2002, 2004) and/or membrane (2006), or the retractor body members (2002, 2004) and/or membrane (2006) may comprise a magnetic material). The retractor body members (2002, 2004) may be arranged substantially parallel to one another and connected to the ends of the membrane (2006), and may enable the retractor (1900) to transition between a low-profile, substantially linear configuration that allows the retractor (1900) to pass through an incision and/or trocar and an expansive platform configuration in which the one or more membranes is expanded for supporting tissue (e.g., an internal organ). The membrane (2006) may be expandable in an accordion-like manner. In the low-profile configuration, the membrane (2006) may be folded to bring the opposing retractor body members (2002, 2004) closer together. In an expansive configuration, the membrane (2006) may expand to unfold the membrane (2006) and separate the retractor body members (2002, 2004) from each other.

In some variations, the retractor (2000) may be biased towards the low-profile configuration, and a force may be applied to move the retractor (2000) to the expansive configuration. For example, in some of these variations, the membrane (2006) may include guidewire cores that enable the retractor (2000) to be expanded or inflated. As another example, the membrane (2006) may additionally or alternatively be expandable by manipulating magnetic material of the retractor (2000) with one or more mechanical devices such as a grasper. To maintain the expansive configuration, for example, the retractor (2000) may comprise a mechanical linkage (not shown) located between the retractor body elements (2002, 2004). The mechanical linkage may function as a one-way ratcheting mechanism to allow the retractor (2000) to move towards an expanded configuration but that may limit movement towards a low-profile configuration unless released. For example, the mechanical linkage may comprise an over-center toggle that actuates into a locked position until a grasper or other tool unlocks the mechanical linkage.

In some variations, the retractor (2000) may be biased toward the expansive configuration. In some variations, the retractor body members (2002, 2004) may comprise magnets with polarities causing them to repel each other to expand the membrane (2006). A delivery sleeve provided over the retractor (2000) or the retractor (2000) provided within a trocar may temporarily restrict the retractor (2000) to the low-profile configuration during delivery. Exiting the trocar and/or removal of the delivery sleeve from the retractor (2000) may relieve the restriction on the retractor (2000) and may allow the retractor (2000) to transition from a low-profile configuration to an expansive configuration. In some variations, the retractor (2000) may further comprise a transitioning mechanism (not shown) to transition the retractor (2000) from the expansive configuration to the low-profile configuration for a retractor (2000) biased towards the expansive configuration. For example, the retractor (2000) may further include strings or sutures, coupled to the retractor body members (2002, 2004), to facilitate such a transition when pulled laterally, such as for removal of the retractor (2000) from the surgical site of the patient or repositioning of the retractor (2000) within the patient.

Figure 21A:
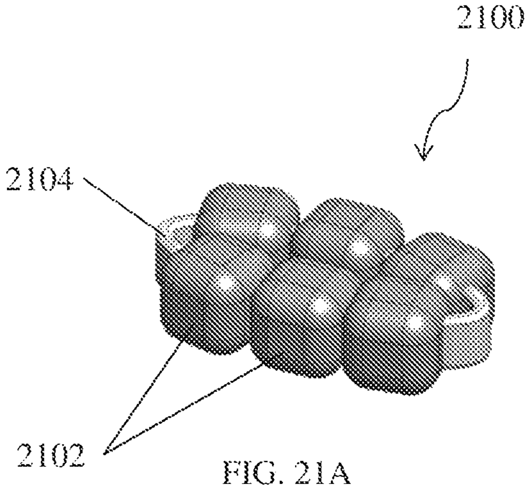
FIGS. 21A and 21B are perspective views of a first low-profile configuration and a second expansive configuration, respectively, of one variation of a retractor.
Figure 21B:
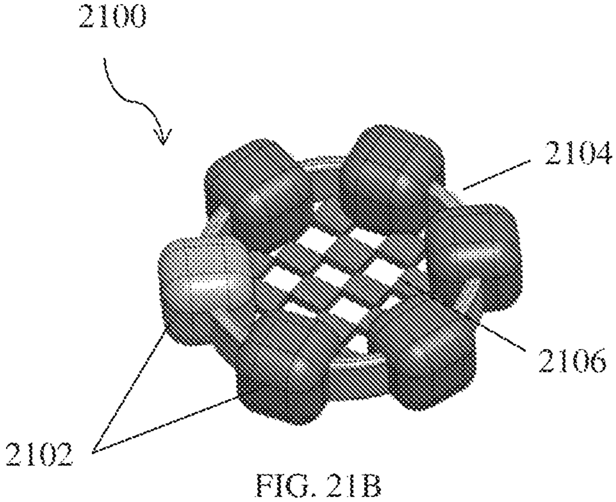

In some variations, a retractor may comprise a retractor body and membrane where the retractor body is provided along a periphery of the membrane. For example. FIGS. 21A and 21B depict a retractor (2100) comprising a retractor body including a plurality of retractor body elements (2102). In a low-profile configuration, the retractor body elements (2102) may be in contact or close together with each other and with the membrane (2106) in a collapsed state. In an expansive configuration (FIG. 21B), the membrane (2106) may be stretched out between retractor body elements (2102). The retractor body elements (2102) and/or membrane (2106) may be coupled to each other by one or more connecting elements (2104). In some variations, the retractor body elements (2102) may be directly connected to one another.

In some variations, at least some of the retractor body elements (2102), connecting element (2104), and/or membrane (2106) may comprise a magnetic portion. In some variations, at least some of the magnetic portion may be a separate magnetic mass made of a magnetic material coupled to a retractor body element, connecting element, and/or membrane, while additionally or alternatively, a portion of the retractor (e.g., at least one retractor body element) may be made of a magnetic material.

The retractor body elements (2102) may be configured to transition between a low-profile, substantially linear configuration (shown in FIG. 21A) that allows the retractor to pass through an incision and/or trocar and an expansive platform configuration (shown in FIG. 21B) to support tissue (e.g., an internal organ). The platform shape may be, for example, a substantially planar shape, a saddle shape, or other curved expansive surface.

Like the variation depicted in FIGS. 2A and 2B, the retractor body elements (2102) may include rounded, atraumatic features to reduce the likelihood of tissue damage. The connecting elements (2104) may interconnect or link the retractor body elements (2102) in series by threading through a lumen of each retractor body element (2102). In some variations, the connecting element (2104), similar to the connecting element (204) described above with reference to FIGS. 2A and 2B, may at least partially influence the geometry of the expansive configuration of the retractor (2100) (e.g., the connecting element (2104) may be substantially restricted to uni-directional or uni-planar deformation). Additionally or alternatively, similar to the retractors described above with reference to FIGS. 2A-5B, the retractor (2100) may be biased toward the low-profile, collapsed configuration and/or expansive configuration.

Figure 22A:
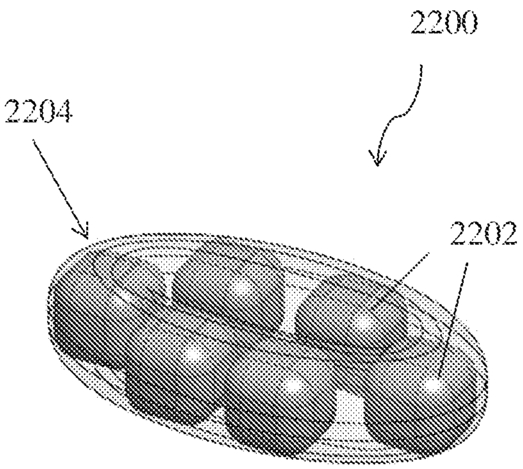
FIGS. 22A and 22B are perspective views of a first low-profile configuration and a second expansive configuration, respectively, of one variation of a retractor.

In some variations, a retractor may comprise a plurality of retractor body elements and a membrane surrounding the retractor body elements. FIGS. 22A and 228 show an example of a retractor (2200) that may comprise a plurality of retractor body elements (2202) and one or more membranes (2204) substantially surrounding at least a portion of the retractor body elements (2202). The retractor (2200) may be configured to transition between a low-profile, substantially linear configuration (shown in FIG. 22A) that is configured to allow the retractor to pass through an incision and/or trocar and an expansive platform configuration (shown in FIG. 22B) configured to support tissue (e.g., an internal organ). In some variations, the retractor body elements (2202) may be coupled to the membrane (2204) at predetermined locations to maintain a desired alignment (e.g., spacing) between the retractor body elements (2202) in the low-profile and expansive configurations. For example, the retractor body elements (2202) may be glued to an inner surface of the membrane (2204). As another example, retractor body elements 2202) may be coupled to a core wire or core cable to maintain a desired alignment.

Figure 22B:
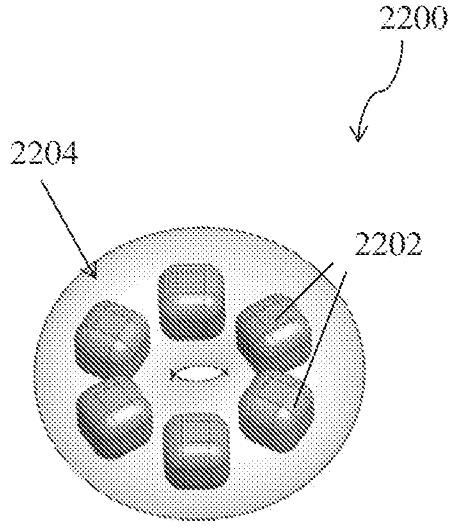

The membrane (2204) may comprise a compressible toroidal sleeve surrounding at least a portion of the retractor body (2202) (as shown in FIG. 22B). The membrane (2204) may comprise a flexible, substantially atraumatic material, such as silicone. In some variations, the membrane (2204) may be elastic and may be inflated to provide a supportive surface. For example, the membrane (2204) may be inflated with one or more liquids (e.g., saline, a ferromagnetic fluid) and/or gasses. Such inflation media may be delivered into the membrane (2204) after the retractor (2200) is delivered to the surgical site. Removal of the fluid may transition the retractor from an expanded configuration to a low-profile configuration in order to facilitate removal from the surgical site. In some variations, inflation and deflation of the membrane (2204) may be carried out through a tube (not shown)

inserted through a trocar and coupled to the membrane (2204) to deliver and remove fluid and/or gasses. In order to allow other instruments to use the trocar when the tube is not in use, an end of the tube may be capped and fully inserted into the body cavity when not in use, and later retrieved for inflation or deflation.

At least a portion of the retractor (2200) may comprise a magnetic material. In some variations, a magnetic mass may be coupled to a retractor body element (2202) and/or membrane (2204). Additionally or alternatively, a portion of the retractor (2200) (e.g., at least one retractor body element, or a fluid within the membrane (2204)) may comprise a magnetic material (e.g., the fluid may be a ferromagnetic fluid). Alternatively, one or more magnetic elements may be embedded within the membrane sleeve. Although FIGS. 22A and 22B depict a variation of the retractor (2200) in which the membrane (2204) surrounds a plurality of retractor body elements (2202) in a toroidal sleeve, in other variations, the membrane (2204) and/or the retractor (2200) may have any suitable shape.

Figure 23A:
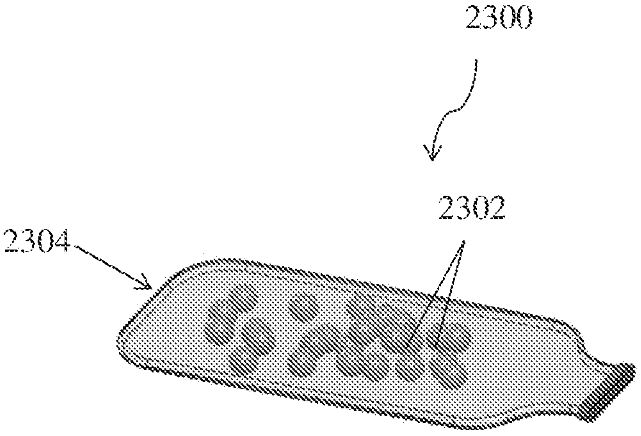
FIGS. 23A and 23B are perspective views of a first low-profile configuration and a second expansive configuration, respectively, of one variation of a retractor.
Figure 23B:
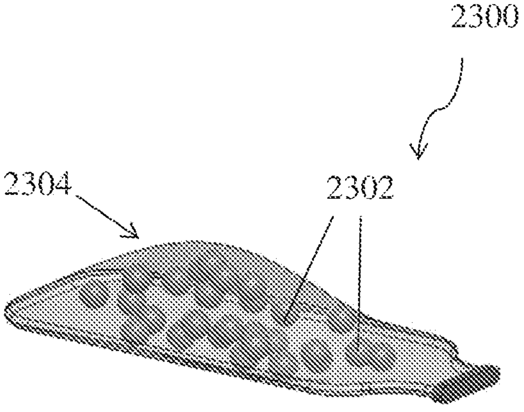

In some variations, a retractor may comprise freely movable retractor body elements within a pouch-like membrane. For example, as shown in FIGS. 23A and 23B, a retractor (2300) may comprise a plurality of retractor body elements (2302) and one or more membranes (2304) in the form of a pouch substantially surrounding the retractor body elements (2302). The retractor body elements (2302) may comprise a magnetic material such that an external magnet may be used to manipulate the retractor body elements (2302) to expand the pouch in order to provide a platform to support an internal organ. At least some of the magnetic elements may be freely movable in all directions within the pouch (2304), or may be at least partially restricted in motion such as being confined to a track or compartment within the pouch (2304). In some variations, the pouch (2304) may be flexible and conform to the shape of the tissue (e.g., an internal organ).

The retractor (2300) may comprise a low-profile, collapsed configuration (shown in FIG. 23A) and an expansive configuration (shown in FIG. 231B). In some variations, the retractor (2300) in its low-profile configuration may be reduced in size by folding or rolling the membrane (2304) into a smaller configuration, and may be configured to unfold or unroll after being inserted into the patient. In some variations, the membrane (2304) may be naturally biased to unfold or unroll when unconstrained (e.g., released from a trocar or delivery sleeve), or in other variations, the membrane (2304) may be unfolded or unrolled by manipulating it with a grasper. Similar to the membrane sleeve (2204) described above with reference to FIGS. 22A and 22B, in some variations, the pouch (2304) may additionally or alternatively include a fluid that enables inflation of the pouch (2304) to expand the retractor (2300). In some variations the fluid may comprise a ferromagnetic fluid.

Figure 24A:
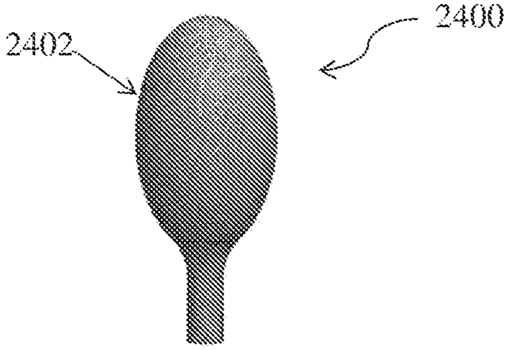
FIGS. 24A and 24B are perspective views of a first low-profile configuration and a second expansive configuration, respectively, of one variation of a retractor.
Figure 24B:
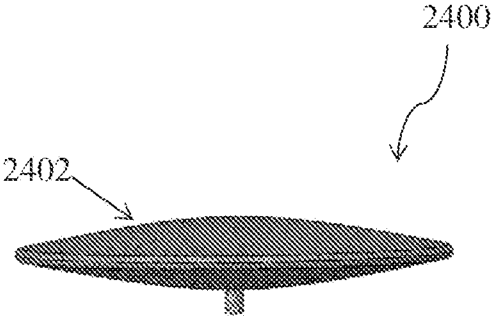

In some variations, a retractor may comprise a membrane configured to transition from a low-profile droplet configuration into an expansive flattened disc configuration. As shown in FIGS. 24A and 24B, the retractor (2400) may comprise a membrane (2402) configured to transition between a low-profile configuration (shown in FIG. 24A) and an expansive flattened disc configuration (shown in FIG. 24B) to support tissue (e.g., an internal organ). In some variations, the retractor (2400) may comprise one or more magnetic elements disposed along or inside the membrane (2402). In particular, the membrane (2402) may comprise a mesh component.

In some variations, the retractor (2400) may comprise retractor body elements (not shown) within the membrane (2402). In some instances, an external magnet may be used to manipulate the retractor body elements to expand the membrane (2402) to a desired degree and/or direction in order to provide a platform to support an internal organ. In other instances the membrane (2402) may be expanded via injection of gasses and/or fluid, which may comprise a ferromagnetic fluid. Like the membrane variations described above, the membrane (2402) may be additionally reduced in size by folding or rolling the membrane (2402). In some variations, inflation and deflation of the membrane (2402) may be carried out by a tube (not shown) inserted through a trocar and coupled to the membrane (2402) to deliver and remove fluid and/or gasses. In order to allow other instruments to use the trocar when the tube is not in use, an end of the tube may be capped and fully inserted into the body cavity.

In some variations, a retractor may be configured such that it is non-uniformly responsive to an applied magnetic field, such that a torque can be applied to tissue. That is, for example, the retractor may comprise a retractor body of non-uniform magnetic susceptibility (e.g., due to a non-uniform distribution of magnetic material) such that different portions of the retractor body respond to an applied magnetic field to different degrees. Such a retractor may include at least one magnetic portion that is moved in a first direction in response to an applied magnetic field pattern, and at least another magnetic portion that is moved in a second direction in response to the applied magnetic field pattern (e.g., from an external magnet located outside the body). This may cause the retractor to tilt to lift at least a portion of tissue (e.g., an internal organ) by, for example, simultaneously having one portion of the retractor magnetically repelled by an external magnet and another portion of the retractor magnetically attracted by the external magnet. Thus, although the variations described with reference to FIGS. 16A-24B are primarily described as platforms for lifting tissue, some or all of these variations may additionally and/or alternatively operate in a manner similar to the lever variations described with reference to FIGS. 11A-15 in order to apply torque to tissue. For example, a retractor having an expansive fan, "X"-shaped, "T"-shaped, zig-zag, or other platform configuration may additionally or alternatively pivotably support (i.e., operate as a moment arm for exerting a moment on) all or a portion of tissue (e.g., an internal organ).

Retractor—Sling

In some variations, a retractor may form a sling that may be configured to lift tissue (e.g., an internal organ) and suspend it from an interior wall of a patient. In these variations, a first configuration of the retractor may generally be linear, and a second configuration of the retractor may be generally curvilinear. The first configuration may allow the retractor to be inserted through an incision and/or a trocar, while the second configuration may allow the retractor to engage an underside or other suitable side of tissue and, under the influence of an external magnet, suspend the tissue and thereby retract or otherwise manipulate/move the engaged tissue.

More specifically, generally, retractors configured to form a sling as described herein may pass through an incision and/or laparoscopic trocar into a surgical site within a patient in the substantially linear configuration. In some variations, the retractor may be constrained by a trocar, an external sleeve, a guidewire, or the like. Retractors configured to form a sling may be biased towards a curvilinear configuration such that when unconstrained, the retractor may move into the curvilinear configuration. For example, a user may manipulate the retractor with a grasper through a trocar toward an internal surgical site, maneuver the retractor underneath the tissue (e.g., an internal organ), release the retractor from the grasper, and then withdraw the grasper from the trocar. A magnetic field generated from an external magnet may attract opposing ends of the retractor such that the retractor forms a sling that holds up the tissue closer towards a body cavity wall.

Figure 25A:
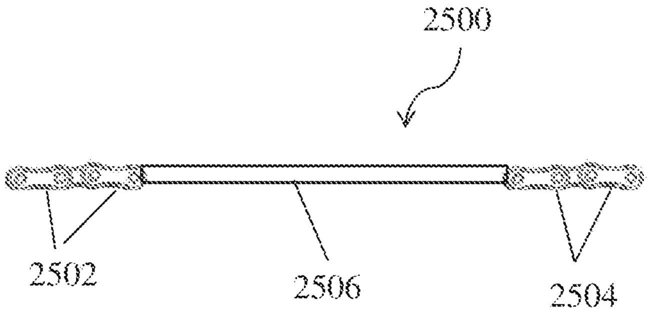
FIGS. 25A and 25B are perspective views of a first low-profile configuration and a second expansive configuration, respectively, of one variation of a retractor.
Figure 25B:
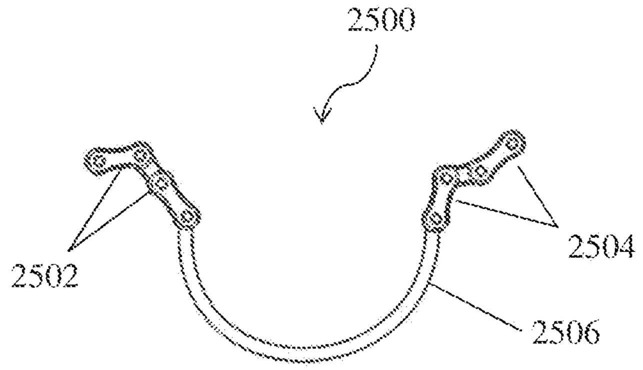

In some variations, a retractor may form a curvilinear sling for engaging tissue. As shown in FIGS. 25A-25B, the retractor (2500) may comprise a first retractor body (2502), a second retractor body (2504), and a connecting element (2506) connecting the first retractor body (2502) and the second retractor body (2504). Each or some of the retractor bodies (2502, 2504) may include a magnetic portion (e.g., a magnetic material may be coupled to at least one retractor body element, or at least one retractor element may be at least partially made of a magnetic material). The retractor (2500) may transition between a substantially linear configuration (shown in FIG. 25A) that allows the retractor to be delivered through an incision and/or trocar, and a curvilinear configuration (shown in FIG. 258).

Figure 25C:
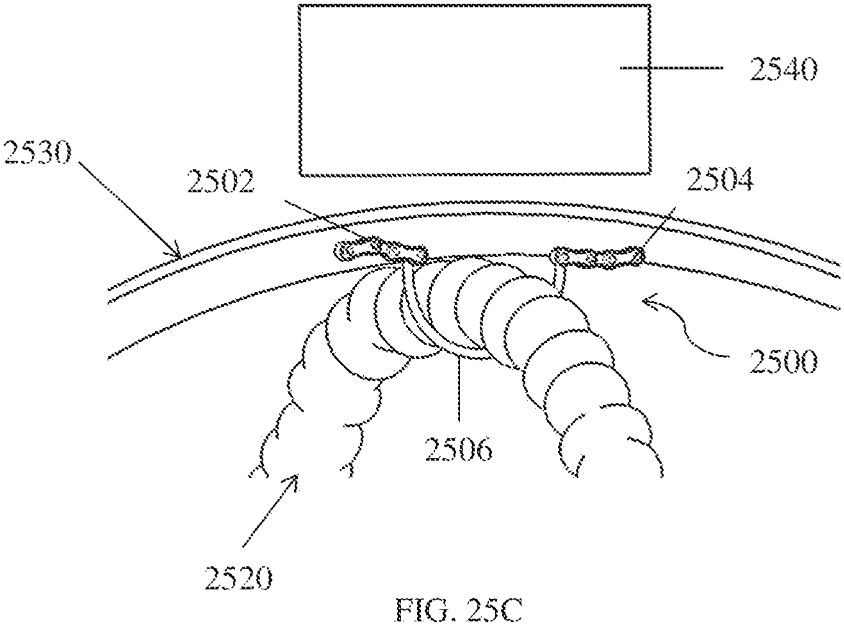
FIG. 25C is a schematic representation of one variation of a retractor system.

As shown in FIG. 25C, in the curvilinear configuration of the retractor (250), the connecting element (2506) forms a sling for suspending at least a portion of tissue (e.g., an internal organ) (2520). In some variations, the retractor (2500) in the substantially linear configuration may be inserted through a trocar and into a body cavity. An end of the retractor (2500) (e.g., first or second retractor body element (2502, 2504)) may be guided under tissue (e.g., an internal organ) by a grasper. The first retractor body element (2502) and second retractor body element (2504) comprising magnetic portions may then be drawn toward the patient wall (2530) in response to an external magnet (2540), thereby retracting the tissue (2520) by suspension. Additionally or alternatively, the grasper may be used to raise the retractor body elements (2502, 2504) towards the patient wall (2530), and a magnetic field generated by an external magnet (2540) may hold the retractor (2500) in place.

In some variations, as shown in FIGS. 25A and 25B, each of the first retractor body (2502) and the second retractor body (2504) may comprise a plurality of interconnected links. Within each retractor body (2502, 2504), the links may be connected by a pin joint or other suitable joint such that adjacent retractor body elements may be configured to rotate relative to one another substantially within a single plane, around a pin joint connection. In other examples, the links may be joined with connections permitting a wider range of motion (e.g., ball-and-socket joints), chained to one another, or connected in any suitable manner. Furthermore, the retractor body elements may be of any geometry that allows for movement relative to one another.

In some variations, as shown in FIGS. 25A through 25C, the terminal retractor body elements may comprise a magnetic material or have magnetic masses disposed on them. The retractor body elements may be configured to be attracted to a magnetic field (e.g., produced by an external magnet (2540)). When the connecting element (2506) is looped underneath a portion of tissue (2520), at least a portion of the tissue (2520) may be suspended by the connecting element (2506) and moved towards the patient wall (2530). In some variations, each of the retractor body elements (2502) and (2504) may comprise a terminal retractor body element and penultimate retractor body element (and may include additional retractor body elements). The penultimate retractor body element on each side of the retractor may be equally ferromagnetic to the terminal retractor body element, or less ferromagnetic than the terminal retractor body element.

In some variations, the connecting element (2506) may be configured to transition the retractor between the substantially linear configuration and the curvilinear configuration. In some variations, the connecting element (2506) may transition between these configurations under manipulation by an external magnet (2540). For example, the retractor elements (2502, 2504) may be attracted to the external magnet (2540), causing them to move toward the external magnet (2540) (as shown for example in FIG. 25C), while the connecting element (2506) may not be attracted to the external magnet (2540), and thus the force of gravity on the connecting element (2506) may cause the retractor body to form a sling configuration.

In some variations, the shape of the retractor in the curvilinear configuration may be adjusted by changing the distance between the retractor body elements. In some instances, each of the retractor body elements (2502, 2504) may be manipulated using separate external magnets, which may help to control the location of each retractor body element when attracted by magnetic fields generated by the external magnets. In some variations, the connecting element (2506) may be biased toward the curvilinear configuration. For example, the connecting element (2506) may be constrained in the linear configuration during delivery by trocar or delivery sleeve, but may transition the retractor into the curvilinear configuration after it is released from the trocar or delivery sleeve. As another example, the connecting element (2506) may be disposed over a guidewire (not shown) that holds the retractor in a substantially linear configuration. Once the retractor is within the patient, the guidewire may be removed, which may allow the retractor to transition into the curvilinear configuration.

In some variations, the connecting element (2506) may comprise sutures, ribbons, woven fibers, and/or other suitably flexible materials. A first end of the connecting element (2506) may couple to the first retractor body (2502) with sutures, epoxy, by tying the first end of the connecting element (2506) to the first retractor body (2502), or in any suitable manner. A second end of the connecting element (2506) may be coupled to the second retractor body (2504) in a similar manner.

In some variations, the retractor may have rounded and/or smooth edges and features, such that the retractor may generally engage the tissue (2520) atraumatically to decrease the likelihood of damage to the tissue (2520). Further, the retractor bodies (2502) and (2504) and/or connecting element (2506) may be embedded in an atraumatic medium (not shown), for example silicone, to blunt or smooth the edges of the retractor. As another example, the retractor bodies (2502, 2504) may individually be dip-coated, sprayed, or otherwise covered with a soft polymer (e.g., silicone) or other soft material to atraumatically cushion each retractor body (2502, 2504). As another example, a plurality of retractor bodies (e.g., pairs or groups of three, four, or any suitable number) or the entire retractor may be covered in a soft polymer or other soft material.

Although FIGS. 25A-25C depict a retractor (2500) comprising two retractor body elements coupled to a first end of the connecting element (2506) and a second retractor body (2504) with two retractor body elements coupled to a second end of the connecting element (2506), it should be appreciated that in other variations, a retractor comprising a sling may include fewer or more retractor body elements and/or connecting elements. Furthermore, the retractor body elements and/or connecting elements may be of any suitable shape.

Figure 26A:
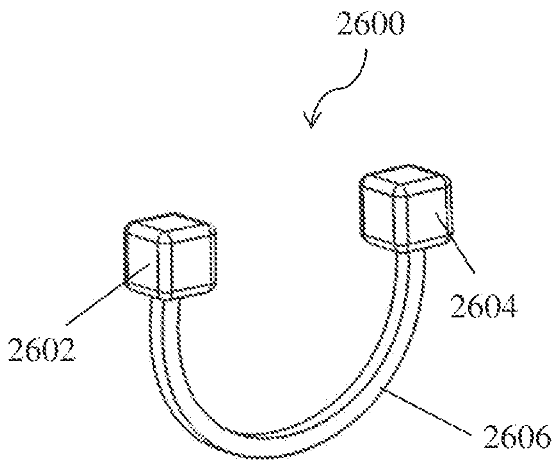
FIG. 26A is a perspective view of one variation of a retractor in an expansive configuration.
Figure 26B:
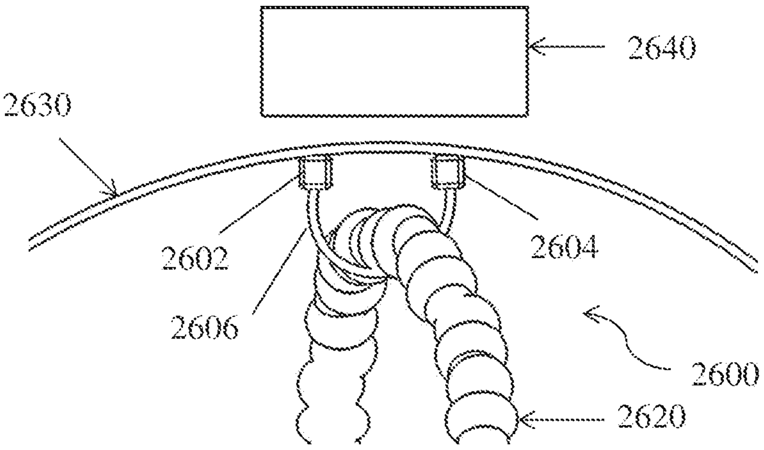
FIG. 26B is an illustrative depiction of one variation of a retractor system.

FIGS. 26A-26B depict another variation of a retractor configured to form a sling. Retractor (2600) may comprise a first retractor body (2602) coupled to a first end of a connecting element (2606) and a second retractor body (2604) coupled to a second end of the connecting element (2606). Generally, the retractor (2600) may operate similarly to retractor (2500) described above with reference to FIGS. 25A-25C. In particular, the retractor (2600) may transition between a low-profile, substantially linear configuration and a curvilinear configuration (shown in FIGS. 26A and 26B) that may support and suspend at least a portion of tissue (e.g., an internal organ) (2620) from the patient wall (2630) in response to a magnetic field. The first retractor body (2602) and the second retractor body (2604) may comprise beads that may generally be cuboidal, spherical, or otherwise have generally atraumatic features to decrease the likelihood of tissue damage.

Figure 27A:
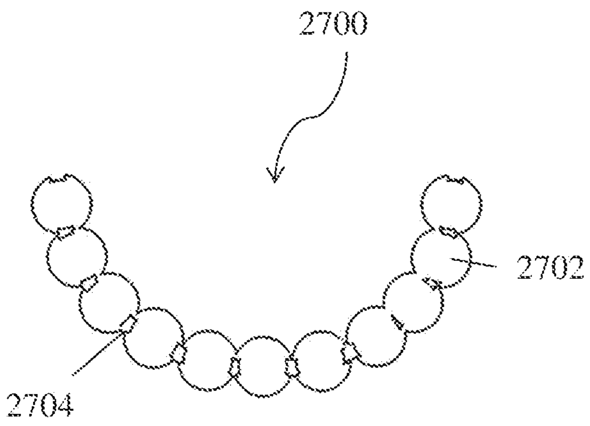
FIG. 27A is a perspective view of one variation of a retractor in an expansive configuration.
Figure 27B:
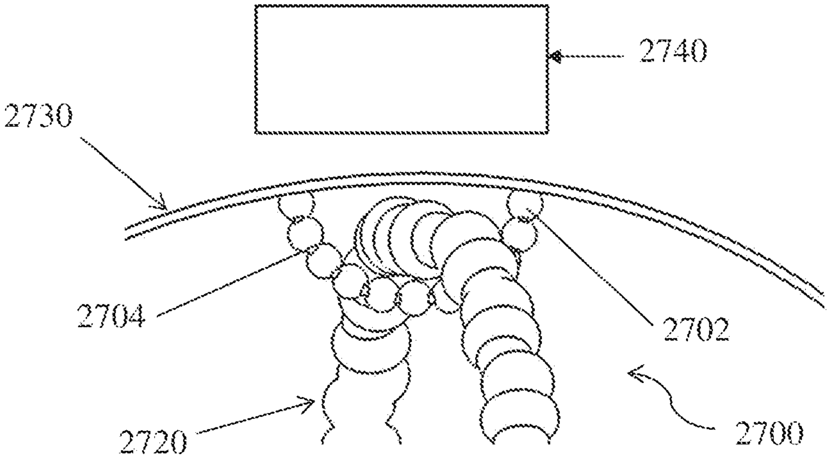
FIG. 27B is an illustrative depiction of one variation of a retractor system.

FIGS. 27A-27B depict yet another variation of a retractor configured to form a sling. Retractor (2700) may comprise a plurality of retractor bodies (2702) disposed in series along the length of a connecting element (2704). Other variations of serial retractor bodies may be similar in construction to those described above with reference to FIGS. 2A-5B, except that the retractor (2700) and its variants may transition between a substantially linear configuration and a curvilinear configuration (shown in FIGS. 27A and 27B). For example, in some variations, some or all of the retractor bodies (2702) (e.g., retractor bodies at first and second ends of the retractor (2700)) may incorporate a magnetic material such that the retractor (2700) may, in its curvilinear configuration, support and suspend at least a portion of tissue such as an internal organ (2720) from the patient wall (2730) in response to a magnetic field. Additionally or alternatively, the connecting element (2704) may be biased toward the linear configuration and/or the curvilinear configuration.

Magnetic Control Component

FIG. 1 illustrates a schematic representation of a retractor system (100) as described herein. As shown in FIG. 1, a retractor system (100) may comprise a retractor (110) and a magnetic control component (140). The magnetic control component (140) may be sized and configured to be placed over the surgical site (132), external to the patient. The magnetic control component (140) may be configured to generate a magnetic field, particularly to apply a magnetic force to the retractor (110) for manipulating the retractor (110). For instance, in some variations, the magnetic control component (140) may generate a magnetic force that transitions the retractor (110) between a low-profile configuration and an expansive configuration. Additionally or alternatively, the magnetic force may induce the retractor (I 10) to engage tissue (e.g., an internal organ) and/or move the retractor (110) and the engaged tissue. In some variations, the magnetic control component (140) may comprise a force modulation device configured to alter a magnitude of the magnetic force applied by the magnet.

In some variations, the magnetic control component (140) may comprise one or more permanent magnets, one or more electromagnets, and/or one or more electro-permanent magnets. The magnetic control component may comprise any number of individual magnets, which in some instances may be formed in an array or other assembly. Examples of magnetic control components and assemblies suitable for use with the systems described here are described in U.S. patent application Ser. No. 14/200,302, filed on Mar. 7, 2014, and titled "Magnetic Control Assemblies and Systems Therefor," the contents of which are hereby incorporated by reference in their entirety.

II. Systems

Also described here are systems for moving an internal organ or other tissue in a patient, in instances such as minimally-invasive surgery. Generally, the systems may comprise a retractor having a low-profile configuration and an expansive configuration. The system may further comprise a magnetic control component as described herein. The retractor may be similar to any of the retractors described in more detail above. In some variations, the retractor may be biased toward the low-profile configuration or biased toward the expansive configuration. In other variations, the retractor may transition between the low-profile and expansive configurations under the operation of a mechanical device and/or under the effect of a magnetic field, as described herein.

The retractor in the low-profile configuration may pass through an incision into a surgical site within a patient. In some variations, the retractor in the low-profile configuration may be sized and configured to be passed through a laparoscopic trocar. The retractor in the expansive configuration may engage tissue (e.g., an internal organ). Such engagement may enable displacement of the internal organ from the surgical site and/or bring the internal organ toward a more easily accessible surgical site. In some variations, as described in further detail herein, the retractor in its expansive configuration may engage tissue by forming a supportive surface that engages an underside and/or other suitable surface of the tissue. For example, the retractor in the expansive configuration may form a platform for contacting an underside of the tissue, or may form a cradle for contacting multiple portions of the tissue.

The system including the magnetic control component may comprise any of the magnetic control components described in more detail herein. The magnetic control component may be placed over the surgical site external to the patient and may generate a magnetic field that draws at least a portion of the retractor toward the magnetic control component. By manipulating the magnetic field and inducing movement of the magnetic portion of the retractor when the retractor is engaged with tissue, a user may lift, tilt (i.e., apply a moment to), and/or otherwise displace the engaged tissue. In some variations, the retractor system may comprise multiple retractors. Furthermore, in some variations, the retractor system may comprise multiple magnetic control components, where at least some of the magnetic control components may be controlled independently of the others. In variations in which some magnetic control components are operated independently, each magnetic control component may be configured to apply a magnetic force to a respective retractor or portion of a retractor, such that multiple retractors or different portions of a retractor may be moved independently.

III. Methods

Also described here are methods for supporting and/or moving tissue (e.g., an internal organ) of a patient, in instances such as minimally-invasive surgery. Generally, the methods described here may include passing a retractor in a first low-profile configuration through an incision into a surgical site within a patient. The retractor may comprise at least one magnetic portion. The retractor within the patient may transition from the first low-profile configuration to a second expansive configuration. The retractor may engage tissue, such as an internal organ. A magnetic control component may be placed over the surgical site external to the patient. At least a portion of the retractor and the internal organ may be drawn toward the magnetic control component by a magnetic field generated by the magnet.

More specifically, the retractor, while in its first low-profile configuration, may be delivered to a surgical site within a patient through a surgical incision and/or a trocar. For example, a user may shuttle the retractor with a grasper through a trocar toward an internal surgical site, release the retractor from the grasper, then withdraw the grasper from the trocar (or continue to use the grasper for other manipulations at or near the surgical site). Once the retractor is passed into the patient, the retractor may be positioned to permit other tools or devices access through the same incision, thereby lowering the total number of incisions that are needed for the surgical procedure. After the retractor is delivered into the patient, the retractor may be transitioned from the first low-profile configuration to the second expansive configuration. The configuration change may be controlled, for example, by moving the location of the magnetic control component and/or modulating the strength or pattern of the magnetic field. As another example, the configuration change may be performed by a mechanical device (e.g., grasper). As yet another example, the retractor may be biased toward the expansive configuration, and release of the grasper from an element constraining it to a low-profile configuration may cause it to naturally assume an expansive configuration.

In the expansive configuration, the retractor may engage tissue (e.g., an internal organ), such as by providing a supportive platform, cradle, sling, or any suitable structure as described herein. In some variations, the retractor may engage the internal organ when the retractor is in the second expansive configuration. In other variations, the retractor may engage or partially engage the internal organ when the retractor is in the first configuration and then transition to the expansive configuration while engaging the tissue.

When the retractor has engaged tissue (e.g., an internal organ), the magnetic control component may be manipulated to draw at least a portion of the retractor and the tissue toward the magnetic control component. Displacement of at least a portion of the tissue may increase accessibility to a surgical site near the tissue and/or on the tissue itself. In some variations, the magnetic control component may attract one or more magnetic portions of the retractor toward the magnetic control component, thereby lifting, suspending, or otherwise positioning at least a portion of the tissue closer to the magnetic control component.

In some variations, the retractor may be positioned and maintained at a predetermined location within the patient. A magnetic control component may then apply a magnetic force to maintain the location of the retractor within the patient. Tissue may be positioned by physically manipulating it (e.g., such that at least a portion of tissue may be contacted and engaged by the retractor to support the tissue), for example, using a grasper tool and/or another retractor. The retractor may in turn exert a force on at least a portion of the tissue to maintain the location of the tissue. In these variations, tissue may be support by the retractor, but not moved by the retractor.

In some variations, the magnetic control component may use magnetic force to tilt the retractor to lift at least a portion of the internal organ. For instance, a first portion of the retractor may move toward the magnetic control component while a second portion of the retractor may move away from the magnetic control component, thereby pivoting the retractor to apply force to at least a portion of the tissue remote to the magnetic portions to increase accessibility to a surgical site.

In some variations, the movement and/or rotation of at least a portion of the tissue may be in the same direction as the movement and/or rotation of the retractor. In other variations, the movement and/or rotation of the retractor may cause at least a portion of the organ to move relative to the retractor, such that a component of its movement is orthogonal to movement of the retractor. In variations in which the retractor forms a non-planar surface (e.g., a saddle shape), the direction of movement of at least a portion of the organ may vary as at least a portion of the organ is increasingly retracted.

In some variations, the methods described here may further comprise maintaining the retractor in a position that keeps the tissue (e.g., an internal organ) in a retracted position, which may help maintain access to a surgical site during a surgical procedure. For instance, the magnetic control component may be used to stabilize the retractor against an internal wall of the patient or against other tissue within the patient. In some variations, a magnetic field provided by the magnetic control component enables the internal organ to be self-maintained in a retracted position without continual attention.

In some variations, the methods described here may further comprise transitioning the retractor from the second expansive configuration to the first low-profile configuration. For example, such a transition may convert the retractor into a low-profile configuration for repositioning the retractor within the patient (e.g., for use in moving a second portion of tissue), or for withdrawing the retractor from the surgical site in the patient. In some variations, the transition from the second expansive configuration to the first low-profile configuration may be performed by a mechanical device (e.g., grasper) to hold the retractor in the first low-profile configuration.

While the inventive devices, systems, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

We claim:

1. A retractor for supporting or moving at least a portion of an internal organ of a patient, the retractor comprising:
- a body comprising:
  - a linkage member; and
  - a flexible member coupled to the linkage member at a pivot axis,
  - wherein a first portion of the body is configured to be repelled by an applied magnetic force and simultaneously a second portion of the body is configured to be attracted by the applied magnetic force, and wherein the first and second portions of the body are independently movable.

2. The retractor of claim 1, wherein the flexible member is non-rigid or semi-rigid.

3. The retractor of claim 1, wherein the flexible member is a suture.

4. The retractor of claim 1, wherein the flexible member is elongated.

5. The retractor of claim 1, wherein the flexible member comprises a first end and a second end, and a first magnetic portion coupled to the first end and a second magnetic portion coupled to the second end.

6. The retractor of claim 5, wherein the first and second magnetic portions have the same polarity.

7. The retractor of claim 1, wherein the retractor comprises a low-profile configuration and an expansive configuration.

8. A system for supporting or moving at least a portion of an internal organ of a patient, the system comprising:

a retractor comprising a linkage member and a flexible member coupled at a pivot axis, and a magnetic control component configured to be placed over a surgical site external to the patient and induce a magnetic field to repel a first portion of the retractor away from the magnetic control component and simultaneously attract a second portion of the retractor toward the magnetic control component, wherein the first and second portions of the retractor are independently movable.

9. The system of claim 8, wherein at least a portion of the flexible member is attracted to the magnetic control component.

10. The system of claim 8, wherein the flexible member is an elongate member.

11. The system of claim 8, wherein the flexible member is non-rigid or semi-rigid.

12. The system of claim 8, wherein the magnetic control component comprises two external magnets with opposite polarities.

13. The system of claim 8, wherein the magnetic control component comprises an external magnet configured to control a strength of the magnetic field applied to the retractor.

14. The system of claim 8, wherein the magnetic control component is configured to modulate one or more of a location of the pivot axis, a degree of tilt of the retractor, and a strength of magnetic force applied to the retractor.

15. A method for supporting or moving at least a portion of an internal organ of a patient, the method comprising:

passing a retractor into a body cavity within the patient, the retractor comprising a linkage member and a flexible member coupled at a pivot axis;

engaging the internal organ with the retractor;

adjusting a position of the pivot axis relative to a wall of the body cavity using a magnetic control component to simultaneously attract a first portion of the retractor toward the magnetic control element and repel a second portion of the retractor away from the magnetic control element so as to adjust a position of the internal organ, wherein the first and second portions of the retractor are independently movable.

16. The method of claim 15, further comprising transitioning the retractor from a low-profile configuration to an expansive configuration within the body cavity of the patient.

17. The method of claim 15, wherein the flexible member comprises a first end and a second end, and a first magnetic portion coupled to the first end and a second magnetic portion coupled to the second end.

18. The method of claim 17, wherein adjusting the position of the pivot axis comprises moving the magnetic control component to move the first and second magnetic portions of the flexible member.

* * * * *